United States Patent
Seehra et al.

(10) Patent No.: US 8,216,997 B2
(45) Date of Patent: Jul. 10, 2012

(54) METHODS FOR INCREASING RED BLOOD CELL LEVELS AND TREATING ANEMIA USING A COMBINATION OF GDF TRAPS AND ERYTHROPOIETIN RECEPTOR ACTIVATORS

(75) Inventors: Jasbir Seehra, Lexington, MA (US); Robert Scott Pearsall, Woburn, MA (US); Ravindra Kumar, Acton, MA (US)

(73) Assignee: Acceleron Pharma, Inc., Cambridge, MA (US)

( * ) Notice: Subject to any disclaimer, the term of this patent is extended or adjusted under 35 U.S.C. 154(b) by 0 days.

(21) Appl. No.: 12/856,420

(22) Filed: Aug. 13, 2010

(65) Prior Publication Data

US 2011/0038831 A1 Feb. 17, 2011

Related U.S. Application Data

(63) Continuation-in-part of application No. 12/583,177, filed on Aug. 13, 2009, now Pat. No. 8,058,229, and a continuation-in-part of application No. PCT/US2009/004659, filed on Aug. 13, 2009.

(60) Provisional application No. 61/305,901, filed on Feb. 18, 2010, provisional application No. 61/189,094, filed on Aug. 14, 2008.

(51) Int. Cl.
*A61K 38/00* (2006.01)
*A61P 7/00* (2006.01)
*A61P 7/06* (2006.01)

(52) U.S. Cl. .......................................... 514/1.1; 514/7.9
(58) Field of Classification Search .................. None
See application file for complete search history.

(56) References Cited

U.S. PATENT DOCUMENTS

| | | | |
|---|---|---|---|
| 4,973,577 A | 11/1990 | Vale, Jr. et al. |
| 5,118,667 A | 6/1992 | Adams et al. |
| 5,658,876 A | 8/1997 | Crowley et al. |
| 5,808,007 A | 9/1998 | Lee et al. |
| 5,824,637 A | 10/1998 | Crowley et al. |
| 5,847,078 A | 12/1998 | Eto et al. |
| 5,885,794 A | 3/1999 | Mathews et al. |
| 6,004,780 A | 12/1999 | Soppet et al. |
| 6,093,547 A | 7/2000 | Jin et al. |
| 6,132,988 A | 10/2000 | Sugino et al. |
| 6,162,896 A | 12/2000 | Mathews et al. |
| 6,451,334 B2 | 9/2002 | Perrine |
| 6,599,876 B2 | 7/2003 | Kojima |
| 6,605,699 B1 | 8/2003 | Ni et al. |
| 6,656,475 B1 | 12/2003 | Lee et al. |
| 6,656,708 B1 | 12/2003 | Yu et al. |
| 6,692,925 B1 | 2/2004 | Miyazono et al. |
| 6,696,260 B1 | 2/2004 | Lee et al. |
| 6,777,205 B1 | 8/2004 | Carcagno et al. |
| 6,835,544 B2 | 12/2004 | Mathews et al. |
| 6,891,082 B2 | 5/2005 | Lee et al. |
| 7,192,717 B2 | 3/2007 | Hill et al. |
| 7,202,210 B2 | 4/2007 | Wolfman et al. |
| 7,261,893 B2 | 8/2007 | Veldman et al. |
| 7,320,789 B2 | 1/2008 | Aghajania et al. |
| 7,560,441 B2 | 7/2009 | Wolfman et al. |
| 7,612,041 B2 | 11/2009 | Knopf et al. |
| 7,988,973 B2 | 8/2011 | Sherman |
| 8,007,809 B2 | 8/2011 | Sherman |
| 2001/0039036 A1 | 11/2001 | Mathews et al. |
| 2003/0083251 A1 | 5/2003 | Westenfelder |
| 2003/0144203 A1 | 7/2003 | Bowen |
| 2004/0132675 A1 | 7/2004 | Kuo et al. |
| 2004/0138129 A1 | 7/2004 | MacLeod |
| 2004/0197828 A1 | 10/2004 | Gaddy |
| 2004/0209805 A1 | 10/2004 | Phillips et al. |
| 2004/0223966 A1 | 11/2004 | Wolfman et al. |
| 2005/0106148 A1 | 5/2005 | Kay et al. |
| 2005/0197292 A1 | 9/2005 | Smithson et al. |
| 2005/0244867 A1 | 11/2005 | Soppet et al. |
| 2005/0257278 A1 | 11/2005 | Lee et al. |
| 2006/0068468 A1 | 3/2006 | Knopf et al. |
| 2006/0210657 A1 | 9/2006 | Chou |
| 2007/0048830 A1 | 3/2007 | Gilbert et al. |
| 2007/0149455 A1 | 6/2007 | Wolfman et al. |
| 2007/0172956 A1 | 7/2007 | Magari et al. |
| 2007/0184052 A1 | 8/2007 | Lin et al. |
| 2007/0249022 A1 | 10/2007 | Knopf et al. |
| 2007/0275895 A1 | 11/2007 | Duan et al. |
| 2007/0292885 A1 | 12/2007 | Bejanin et al. |
| 2008/0021104 A1 | 1/2008 | Tarallo |
| 2008/0075692 A1 | 3/2008 | Perrine |
| 2008/0089897 A1 | 4/2008 | Wolfman |
| 2008/0102065 A1 | 5/2008 | Borges et al. |
| 2008/0139590 A1 | 6/2008 | Qian et al. |
| 2009/0005308 A1 | 1/2009 | Knopf et al. |
| 2009/0017019 A1 | 1/2009 | Shields et al. |

(Continued)

FOREIGN PATENT DOCUMENTS

WO WO-92/20793 A1 11/1992

(Continued)

OTHER PUBLICATIONS

Bowie et al., 1990, Science 247: 1306-1310.*
"Recombinant Human Activin RIIA/Fc Chimera," R&D Systems 340-R2 (Aug. 27, 2003).
"Recombinant Human Activin RIIB/Fc Chimera," R&D Systems 339-RB/CF (Aug. 27, 2003).
Acceleron Pharma Presents Positive Phase 1 Results Demonstrating ACE-011 Increases Markers of Bone Formation, Acceleron Pharma, pp. 1-2, <www.acceleronpharma.com/contents/news/press-releases/detail.jsp/q/news-id/47> Downloaded from the Internet on Feb. 17, 2009.

(Continued)

*Primary Examiner* — Gyan Chandra
(74) *Attorney, Agent, or Firm* — Ropes & Gray LLP

(57) ABSTRACT

In certain aspects, the present invention provides compositions and methods for increasing red blood cell and/or hemoglobin levels in vertebrates, including rodents and primates, and particularly in humans.

20 Claims, 25 Drawing Sheets

U.S. PATENT DOCUMENTS

| | | |
|---|---|---|
| 2009/0047281 A1 | 2/2009 | Sherman |
| 2009/0074768 A1 | 3/2009 | Knopf et al. |
| 2009/0087433 A1 | 4/2009 | Wolfman et al. |
| 2009/0098113 A1 | 4/2009 | Knopf et al. |
| 2009/0099086 A1 | 4/2009 | Knopf et al. |
| 2009/0118188 A1 | 5/2009 | Knopf et al. |
| 2009/0142333 A1 | 6/2009 | Knopf et al. |
| 2009/0148436 A1 | 6/2009 | LaVallie et al. |
| 2009/0163417 A1 | 6/2009 | Sherman |
| 2010/0068215 A1 | 3/2010 | Seehra et al. |
| 2010/0183624 A1 | 7/2010 | Seehra et al. |
| 2010/0272734 A1 | 10/2010 | Berger et al. |

FOREIGN PATENT DOCUMENTS

| | | |
|---|---|---|
| WO | WO 94/15965 | 7/1994 |
| WO | WO-95/10611 A1 | 4/1995 |
| WO | WO-95/29685 A1 | 11/1995 |
| WO | WO 97/23613 | 7/1997 |
| WO | WO-99/06559 A1 | 2/1999 |
| WO | WO 00/18932 | 4/2000 |
| WO | WO-00/43781 A2 | 7/2000 |
| WO | WO-02/10214 A2 | 2/2002 |
| WO | WO-02/43759 A2 | 6/2002 |
| WO | WO-02/085306 A2 | 10/2002 |
| WO | WO 02/094852 | 11/2002 |
| WO | WO-03/006057 A1 | 1/2003 |
| WO | WO-03/053219 A2 | 7/2003 |
| WO | WO-03/072808 A1 | 9/2003 |
| WO | WO-2004/039948 A2 | 5/2004 |
| WO | WO-2004/108157 A2 | 12/2004 |
| WO | WO 2005/003158 | 1/2005 |
| WO | WO-2005/009460 A2 | 2/2005 |
| WO | WO 2005/014650 | 2/2005 |
| WO | WO-2005/028517 A2 | 3/2005 |
| WO | WO 2005/070967 | 8/2005 |
| WO | WO-2005/094871 A2 | 10/2005 |
| WO | WO-2005/097825 A2 | 10/2005 |
| WO | WO-2006/002387 A2 | 1/2006 |
| WO | WO-2006/012627 A2 | 2/2006 |
| WO | WO-2006/039400 A2 | 4/2006 |
| WO | WO-2006/083183 A1 | 8/2006 |
| WO | WO-2006/088972 A2 | 8/2006 |
| WO | WO 2007/038703 | 4/2007 |
| WO | WO-2007/053775 A1 | 5/2007 |
| WO | WO-2007/062188 A2 | 5/2007 |
| WO | WO-2007/067616 A2 | 6/2007 |
| WO | WO-2007/076127 A2 | 7/2007 |
| WO | WO-2008/031061 A2 | 3/2008 |
| WO | WO-2008/060139 A1 | 5/2008 |
| WO | WO 2008/072723 | 6/2008 |
| WO | WO-2008/076437 A2 | 6/2008 |
| WO | WO 2008/094708 | 8/2008 |
| WO | WO-2008/097541 A4 | 8/2008 |
| WO | WO-2008/100384 A2 | 8/2008 |
| WO | WO-2008/109167 A2 | 9/2008 |
| WO | WO-2008/151078 A1 | 12/2008 |
| WO | WO-2009/009059 A1 | 1/2009 |
| WO | WO-2009/019504 A1 | 2/2009 |
| WO | WO-2009/019505 A2 | 2/2009 |
| WO | WO 2009/025651 | 2/2009 |
| WO | WO 2009/137075 | 11/2009 |
| WO | WO-2009/137613 A2 | 11/2009 |
| WO | WO-2009/158015 A2 | 12/2009 |
| WO | WO-2009/158025 A2 | 12/2009 |
| WO | WO-2010/019261 A1 | 2/2010 |
| WO | WO-2010/083034 A1 | 7/2010 |

OTHER PUBLICATIONS

Akel et al, Neutralization of Autocrine Transforming Growth Factor -β in Human Cord Blood CD34$^+$CD38$^-$Lin$^-$ Cells Promotes Stem-Cell-Factor-Mediated Erythropoietin-Independent Early Erythroid Progenitor Development and Reduces Terminal Differentiation. Stem Cells, 21:557-567 (2003).

Akpan, I., et al., "The effects of a soluble activin type IIB receptor on obesity and insulin sensitivity," International Journal of Obesity, 33(11):1265-1273 (2009).

Allendorph, G.P., et al., "Structure of the ternary signaling complex of a TGF-β superfamily member," PNAS, 103(20):7643-7648 (2006).

Banks, G.B., et al., "The Value of Mammalian Models for Duchenne Muscular Dystrophy in Developing Therapeutic Strategies," Current Topics in Developmental Biology, 84:431-453 (2008).

Benny Klimek, Margaret E., et al., "Acute inhibition of myostatin-family proteins preserves skeletal muscle in mouse models of cancer cachexia," Biochemical and Biophysical Research Communications, 391:1548-1554 (2010).

Berenson, J.R., "Multiple Myeloma," Multiple Myeloma: Plasma Cell Disorders: Merck Manual Professional, pp. 1-5, Jul. 2008. http://www.merck.com/mmpe/print/sec11/ch144/ch144e.html Downloaded from the Internet on Sep. 17, 2010.

Bodey, B., et al., "Failure of Cancer Vaccines: The Significant Limitations of this Approach to Immunotherapy," Anticancer Research, 20:2665-2676 (2000).

Bogdanovich, S., et al., "Functional improvement of dystrophic muscle by myostatin blockade," Nature, 420:418-421 (2002).

Broxmeyer, H.E., et al, "Selective and indirect modulation of human multipotential and erythroid hematopoietic progenitor cell proliferation by recombinant human activin and inhibin," Proc. Natl. Acad. Sci. USA, 85:9052-9056 (1988).

Burdette et al., Activin A mediates growth inhibition and cell cycle arrest through Smads in human breast cancer cells. Cancer Research, 65(17):7968-7975; Abstract (2005).

Cadena, S.M., et al., "Administration of a Soluble Activin Type IIB Receptor Promotes Skeletal Muscle Growth Independent of Fiber Type," Journal of Applied Physiology, 109:635-642 (2010).

Centrella et al., "Activin-A Binding and Biochemical Effects in Osteoblast-Enriched Cultures from Fetal-Rat Parietal Bone," Molecular and Cellular Biology, 11(1):250-58 (1991).

Chamberlain, R.S., et al., "Innovations and strategies for the development of anticancer vaccines," Expert Opinion on Pharmacotherapy, 1(4):603-614 (2000).

Chen, Y.G., et al. "Regulation of Cell Proliferation, Apoptosis, and Carcinogenesis by Activin," Exp. Biol. Med., 227(2):75-87 (2002).

Cirillo et al., Hematocrit, blood pressure, and hypertension. The Gubbio Population Study. Hypertension, 20(3):319-326. (1992).

Coerver, et al., "Activin Signaling through Activin Receptor Type II Causes the Cachexia-Like Symptoms in Inhibin-Deficent Mice," 10(5):534-543 (1996).

Collins, C.D., "Multidisciplinary Symposium: Haematological Malignancies," Cancer Imaging 5:S119-S126 (2005).

Colman, P.M., et al., "Effects of amino acid sequence changes on antibody-antigen interactions," Research of Immunology, 145(1):33-36 (1994).

Daluiski et al., "Bone Morphogenetic Protein-3 is a Negative Regulator of Bone Density," Nature Genetics, 27:84-88 (2001).

Deconinck, N., et al., "Pathophysiology of Duchenne Muscular Dystrophy: Current Hypotheses," Pediatr. Neurol., 36:1-7 (2007).

del Re et al., "Reconstitution and Analysis of Soluble Inhibin and Activin Receptor Complexes in a Cell-free System," The Journal of Biological Chemistry, 279(51):53126-53135 (2004).

Donaldson, et al., "Activin and inhibin binding to the soluble extracellular domain of activin receptor II", Endocrinology 140(4):1760-1766 (1999).

Donaldson, et al., "Molecular Cloning and Binding Properties of the Human Type II Activin Receptor", Biochemical and Biophysical Research Communications, 184(1):310-316 (1992).

Fafioffe, et al.,"Activin and inhibin receptor gene expression in the ewe pituitary throughout the oestrous cycle," Journal of Endocrinology, 182:55-68 (2004).

Frigon, N.L., et al, "Regulation of Globin Gene Expression in Human K562 Cells by Recombinant Activin A," Blood, 79(3):765-772 (1992).

Fuller et al., "Activin A Is an Essential Cofactor for Osteoclast Induction," Biochemical and Biophysical Research Communications, 268:2-7 (2000).

Funaba et al., "Expression and Localization of Activin Receptors During Endochondral Bone Development," European Journal of Endocrinology, 144:63-71 (2001).

Gaddy-Kurten et al., "Inhibin Suppresses and Activin Stimulates Osteoblastogenesis and Osteoclastogenesis in Murine Bone Marrow Cultures," Endocrinology, 143(1):74-83 (2002).

Gamer et al., "BMP-3 is a Novel Inhibitor of Both Activin and BMP-4 Signaling in *Xenopus* Embryos," Developmental Biology, 285:156-168 (2005).

Ge, G., et al., "GDF11 Forms a Bone Morphogenetic Protein 1-Activated Latent Complex That Can Modulate Nerve Growth Factor-Induced Differentiation of PC12 Cells", Molecular and Cellular Biology, 25(14):5846-5858 (2005).

GenBank NM_001106, *Homo sapiens* activin A receptor, type IIB (ACVR2B), mRNA, http://www.ncbi.nlm.nih.gov/entrez/viewer.fcgi?db=nucleotide&val=116734707 (Downloaded on Jan. 29, 2007).

Gilbert, R., et al., "Prolonged dystrophin expression and functional correction of mdx mouse muscle following gene transfer with a helper-dependent (gutted) adenovirus-encoding murine dystrophin," Human Molecular Genetics, 12(11)1287-1299 (2003).

Gonzalez-Cadavid, N. F., et al., "Organization of the human myostatin gene and expression in healthy men and HIV-infected men with muscle wasting," PNAS, 95:14938-14943 (1998).

Gray, et al., "Identification of a binding site on the type II activin receptor for activin and inhibin", Journal of Biological Chemistry, 275(5):3206-3212 (2000).

Greenspan, N. S., et al., "Defining epitopes: It's not as easy as it seems," Nature Biotechnology, 17:936-937 (1999).

Greenwald, et al., "The BMP7/ActRII Extracellular Domain Complex Provides New Insights into the Cooperative Nature of Receptor Assembly," Molecular Cell, 11:605-617 (2003).

Greenwald, J., et al., "Three-finger toxin fold for the extracellular ligand-binding domain of the type II activin receptor serine kinase," Nature Structural Biology, 6(1):18-22 (1999).

Gregoriadis, G., et al., "Polysialic acids: potential in drug delivery," FEBS, 315(3):271-276 (1993).

Gupta, V. et al., "Transforming Growth Factor-b Superfamily: Evaluation as Breast Cancer Biomarkers and Preventive Agents," Current Cancer Drug Targets, 4:165-182 (2004).

Gura, T., "Cancer Models: Systems for Identifying New Drugs Are Often Faulty," Science, 278(5340):1041-1042 (1997).

Hamrick et al., "Bone Mineral Content and Density in the Humerus of Adult Myostatin-Deficient Mice," Calcified Tissue International, 71:63-68 (2002).

Hamrick, "Increased Bone Mineral Density in the Femora of GDF8 Knockout Mice," The Anatomical Record, Part A 272A:388-391 (2003).

Hamrick, M.W., et al., "Femoral Morphology and Cross-sectional Geometry of Adult Myostatin-deficient Mice," Bone, 27(3):343-349 (2000).

Harrison, C.A., et al., "An Activin Mutant with Disrupted ALK4 Binding Blocks Signaling via Type II Receptors," The Journal of Biological Chemistry, 279(27):28036-28044 (2004).

Harrison, et al., "Antagonists of activin signaling: mechanisms and potential biological applications," Trends in Endocrinology and Metabolism, 16(2):73-78 (2005).

Hashimoto et al., "Functional Regulation of Osteoblastic Cells by the Interaction of Activin-A with Follistatin," The Journal of Biological Chemistry, 267(7):4999-5004 (1992).

Hemmati-Brivanlou, A., et al., "A truncated activin receptor inhibits mesoderm induction and formation of axial structures in *Xenopus* embryos," Nature, 359:609-614 (1992).

Herbert, W.J., et al., The Dictionary of Immunology, Academic Press, 3rd Edition, London, pp. 58-59 (1985).

Hilden, K., et al., "Expression of Type II Activin Receptor Genes During Differentiation of Human K562 Cells and cDNA Cloning of the Human Type IIB Activin Receptor," Blood, 83(8):2163-2170 (1994).

Hill, J.J., et al., "Regulation of Myostatin in Vivo by Growth and Differentiation Factor-Associated Serum Protein-1: A Novel Protein with Protease Inhibitor and Follistatin Domains," Molecular Endocrinology, 17(6):1144-1154 (2003).

Hsieh, Matthew M, et al., "HIF-prolyl hydroxylase inhibition results in endogenous erythropoietin induction, erythrocytosis, and modest fetal hemoglobin expression in rhesus macaques," Blood, 110(6):2140-2147 (2007).

Ikenoue et al., "Inhibitory Effects of Activin-A on Osteoblast Differentiation During Cultures of Fetal Rat Calvarial Cells," Journal of Cellular Biochemistry, 75:206-214 (1999).

Kaiser, J., "First Pass at Cancer Genome Reveals Complex Landscape," Science, 313:1370 (2006).

Kaspar, B.K., et al., "Retrograde Viral Delivery of IGF-1 Prolongs Survival in a Mouse ALS Model," Science, 301:839-842 (2003).

Kim, et al., "Type IIa IgG-Fc Fusion Protein, Increases Hemoglobin and Hematocrit Levels in Postmenopausal Healthy Women," Blood, 112(11):1316 (2008).

Knight, "Roles of Inhibins, Activins, and Follistatin in the Female Reproductive System," Frontiers in Neuroendocrinology, 17:476-509 (1996).

Kosaki, R., et al., "Left-Right Axis Malformations Associated With Mutations in ACVR2B, the Gene for Human Activin Receptor Type IIB," American Journal of Medical Genetics, 82:70-76 (1999).

Koseki, et al., "Role of TCF-b Family in Osteoclastogenesis Induced by RANKL," Cellular Signaling, 14:31-36 (2002).

Krag, T.O.B., et al., "Heregulin ameliorates the dystrophic phenotype in mdx mice," PNAS, 101(38):13856-13860 (2004).

Krneta, J., et al., "Dissociation of Angiogenesis and Tumorigenesis in Follistatin- and Activin-Expressing Tumors," Cancer Research, 66(11):5686-5695 (2006).

Krystal et al., Transforming Growth Factor β1 Is an Inducer of Erythroid Differentiation. J. Exp. Med. vol. 180 pp. 851-860 (1994).

Kubanek, B., "Introduction: The Role of the Microenvironment and Cytokines on the Modulation of Erythropoiesis," Annals New York Academy of Sciences, pp. 257-258 (1994).

Kunihro, T., et al., "Regulation of Muscle Mass and Hepatic Steatosis by Follistatin-derived Myostatin Inhibitors," Making Muscle in the Embryo and Adult: a joint meeting of Frontiers in Myogenesis and Skeletal Muscle Stem and Satellite Cells, New York, NY, p. 45 (Abstract) (1990).

Lazar, E., et al., "Transforming Growth Factor α: Mutation of Aspartic Acid 47 and Leucine 48 Results in Different Biological Activities," Molecular and Cellular Biology, 8(3):1247-1252 (1988).

Lebrun, J.J., et al, "Activin and Inhibin Have Antagonistic Effects on Ligand-Dependent Heteromerization of the Type I and Type II Activin Receptors and Human Erythroid Differentiation," Molecular and Cellular Biology, 17(3):1682-1691 (1997).

Lee et al., "Regulation of Muscle Growth by Multiple Ligands Signaling Through Activin Type II Receptors," PNAS 102(50):18117-18122 (2005).

Lee, et al., "Regulation of Myostatin Activity and Muscle Growth," PNAS, 98(16):9306-9311 (2001).

Leto et al., "Activin A Circulating Levels in Patients with Bone Metastasis from Breast or Prostate Cancer," Clin Exp Metastasis, 23(2):117-122 (2006).

Li, Q., et al., "Prevention of cachexia-like syndrome development and reduction of tumor progression in inhibin-deficient mice following administration of a chimeric activin receptor type II-murine Fc protein," Molecular Human Reproduction, 13(9):675-683 (2007).

Ludlow, H., et al., "Development of a new antibody to the human inhibin/activin βB subunit and its application to improved inhibin B ELISAs," J. Immunol. Methods, 329:102-111 (2008).

Maguer-Satta, V., et al, "Regulation of human erythropoiesis by activin A, BMP2, and BMP4, members of the TGFβ family," Experimental Cell Research, 282:110-120 (2003).

Matzuk et al., "Different phenotypes for mice deficient in either activins or activin receptor type II," Nature, 374:356-360 (1995).

McNally, E.M., "Powerful Genes—Myostatin Regulation of Human Muscle Mass," N. Engl. J. Med., 350(26):2642-2644 (2004).

McPherron, A.C., et al., "Regulation of Skeletal Muscle Mass in Mice by a Bew TGF-b Superfamily Member," Nature, 387:83-90 (1997).

McPherson, S.J., et al., "Growth inhibitory response to activin A and B by human prostate tumour cell lines LNCaP and DU1465", Journal of Endocrinology, 154:535-545 (1997).

Menstruation: Absent Periods (Amenorrhea), Website downloaded on Jun. 14, 2010, <http://adam.about.com/reports/000101_2.htm?p=1> (11 pages).

Merck Manuals Online Medical Library (online). Anemia of Chronic Disease, Jun. 10, 2008. Downloaded from the internet on Jan. 5, 2010. <http://web.archive.org/web/20080610070226/http://www.merck.com/mmpe/sec11/ch130/ch130d.html> pp. 1-2.

Merck Manuals Online Medical Library (online). Iron Deficiency Anemia, Jun. 10, 2008. Downloaded from the internet on Jan. 5, 2010. <http://web.archive.org/web/20080610070221/http://www.merck.com/mmpe/sec11/ch130/ch130d.html> pp. 1-4.

Meriggiola et al., "Follistatin Decreases Activin-Stimulated FSH Secretion with No Effect on GnRH-Stimulated FSH Secretion in Prepubertal Male Monkeys," Endocrinology, 134(4):1967-1970 (1994).

Mickle, et al., "Genotype-Phenotype Relationships in Cystic Fibrosis," Med. Clin. North Am., 84(3):597-607 (2000).

Miura, P., et al., "Utrophin upregulation for treating Duchenne or Becker muscular dystrophy: how close are we?," Trends in Molecular Medicine, 12(3):122-129 (2006).

Murase et al., "Possible Involvement of Protein Kinases and Smad2 Signaling Pathways on Osteoclast Differentiation Enhanced by Activin A," Journal of Cellular Physiology, 188:236-242 (2001).

Nagamine et al., "Immunohistochemical Detection of Activin A, Follistatin, and Activin Receptors during Fracture Healing in the Rat," Journal of Orthopaedic Research, 16:314-321 (1998).

Nakamura, K., et al, "Effect of Erythroid Differentiation Factor on Maintenance of Human Hematopoietic Cells in Co-cultures with Allogenic Stromal Cells," Biochemical and Biophysical Research Communications, 194(3):1103-1110 (1993).

Ngo, J.T., et al., "Computational Complexity, Protein Structure Prediction, and the Levinthal Paradox," The Protein Folding Problem and Tertiary Structure Prediction, Merz et al., eds., Birkhauser, Boston, 492-495 (1994).

Ogawa et al., "Bovine Bone Activin Enhances Bone Morphogenetic Protein-Induced Ectopic Bone Formation," The Journal of Biological Chemistry, 267(20):14233-14237 (1992).

Oh, S.P., et al., "Activin type IIA and IIB receptors mediate Gdf11 signaling in axial vertebral patterning," Genes & Development, 16:2749-2754 (2002).

Oue et al., "Effect of Local Injection of Activin A on Bone Formation in Newborn Rats," Bone, 15(3):361-366 (1994).

Patel, K., et al., "The function of Myostatin and strategies of Myostatin blockade—new hope for therapies aimed at promoting growth of skeletal muscle," Neuromuscular Disorders, 15:117-126 (2005).

Pearsall, et al., "A Soluble Activin Receptor Type IIA (ACTRIIA) Acts As a Novel Bone Anabolic Agent," The Official Journal of the European Calcified Tissue Society, 34th Europena Symposium on Calcified Tissues (2007).

Pearsall, et al., "Treatment with a Soluble Activin Type II Receptor Reverses Bone Loss in Ovariectomized Mice," Journal of Bone and Mineral Research 2006 Abstracts, 21(1):s1-s530 (2006).

Pearsall, R.S., et al., "A soluble activin Type IIA receptor induces bone formation and improves skeletal integrity", PNAS, 105(9):7082-7087 (2008).

Qi, et al., "Blockade of type β transforming growth factor signaling prevents liver fibrosis and dysfunction in the rat," PNAS, 96:2345-2349 (1999).

Raju, T.S., "Glycosylation in the Fc domain of IgG increases resistance to proteolytic cleavage by papain," Biochemical and Biophysical Research Communications, 341:797-803 (2006).

Rebbapragada, et al., "Myostatin Signals Through a Transforming Growth Fact b-Like Signaling Pathway to Block Adipogenesis," Molecular and Cellular Biology, 23(20):7230-7242 (2003).

Reis, F.M., et al., "Activin, Inhibin and the Human Breast," Molecular and Cellular Edocrinology, 225:77-82 (2004).

Risbridger, G.P., et al., "Activins and Inhibins in Endocrine and Other Tumors," Endocrine Reviews, 22(6):836-858 (2001).

Robinson, G.W., et al., "Inhibins and Activins Regulate Mammary Epithelial Cell Differentiation Through Mesenchymal-epithelial Interactions," Development, 124:2701-2708 (1997).

Rodriquez, J.E.S., et al., "Enhanced Osteoclastogenesis Causes Osteopenia in Twisted Gastrulation-Deficient Mice Through Increased BMP Signaling," J. Bone Miner. Res., 24:1917-1926 (2009).

Rosenzweig et al., "Cloning and characterization of a human type II receptor for bone morphogenetic proteins," PNAS, 92:7632-7636 (1995).

Ruzek et al. Minimal Effects on Immune Parameters Following Chronic Anti-TGF-β Monoclonal Antibody Administration to Normal Mice. Immunopharmacology and Immunotoxicology, 25(2):235-257 (2003).

Sakai et al., "Activin Enhances Osteoclast-Like Cell Formation in Vitro," Biochemical and Biophysical Research Communications, 195(1):39-46 (1993).

Sakai et al., "Activin Increases Bone Mass and Mechanical Strength of Lumbar Vertebrae in Aged Ovariectomized Rats," Bone, 27(1):91-96 (2000).

Sakai et al., "Activin release from bone coupled to bone resorption in organ culture of neonatal mouse calvaria," Bone, 26(3):235-240 (2000).

Sakai et al., "Involvement of Activin in the Regulation of Bone Metabolism," Molecular and Cellular Endocrinology, 180:183-188 (2001).

Sakai et al., "Local Administration of Activin Promotes Fracture Healing in the Rat Fibula Fracture Model," Bone, 25(2):191-196 (1999).

Sakai et al., The Measurement of Activin/EDF in Mouse Serum: Evidence for Extragonadal Production. Biochecmical and Biophysical Research Communications, 188(2):921-926 (1992).

Sakai, et al., "Osteogenic Activity of Activin in Young Normal Rats and Young Adult and Aged Rats after Ovariectomy," Bone, 23:S467 (1998).

Sako, D., et al., "Characterization of the Ligand Binding Functionality of the Extracellular Domain of Activin Receptor Type IIB," The Journal of Biological Chemistry, 285(27):21037-21048 (2010).

Satoh et al., Hemodynamic changes by recombinant erythropoietin therapy in hemodialyzed patients. Hypertension, 15(3):262-266 (1990).

Schuelke, M., et al., "Myostatin Mutation Associated with Gross Muscle Hypertrophy in a Child," New England Journal of Medicine, 350(26):2682-2688 (2004).

Shao, L., et al., "Effect of Activin A on Globin Gene Expression in Purified Human Erythroid Progenitors," Blood, 79(3):773-781 (1992).

Shav-Tal, Y., et al., "The Role of Activin A in Regulation of Hemopoiesis," Stem Cells, 20:493-500 (2002).

Shiozaki, M., et al, "Activin A: A Commitment Factor in Erythroid Differentiation," Biochemical and Biophysical Research Communications, 242:631-635 (1998).

Shiozaki, M., et al, "Evidence for the participation of endogenous activin A/erythroid differentiation factor in the regulation of erythropoiesis," Proc. Natl. Acad. Sci. USA, 89:1553-1556 (1992).

Shiozaki, M., et al., "In Vivo Treatment With Erythroid Differentiation Factor (EDF / Activin A) Increases Erythroid Precursors (CFU-E and BFU-E) in Mice," Biochemical and Biophysical Research Communications, 165(3):1155-1161 (1989).

Shuto et al., "Osteoblasts Express Types I and II Activin Receptors During Early Intramembranous and Endochondral Bone Formation," Journal of Bone Mineral Research, 12(3):403-411 (1997).

Song, J., et al., "The Type II Activin Receptors Are Essential for Egg Cylinder Growth, Gastrulation, and Rostral Head Development in Mice," Development Biology, 213:157-169 (1999).

Springer, et al., "Seventh European Congress on Clinical and Economic Aspects of Osteoporosis and Osteoarthritis," Osteoporosis International, 18(1):S29-S75 (2007).

Sun, et al., "FSH Directly Regulates Bone Mass," Cell, 125:247-260 (2006).

Thompson, et al., "Structures of an ActRIIB: activin A complex reveal a novel binding mode for TGF-beta ligand: receptor interactions", EMBO 22(7):1555-1566 (2003).

Tinsley, J., et al., "Expression of full-length utrophin prevents muscular dystrophy in *mdx* mice," Nature Medicine, 4(12):1441-1444 (1998).

Tsuchida, et al., "Activin isoforms signal through type I receptor serine/threonine kinase ALK7," Molecular and Cellular Endocrinology, 220:59-65 (2004).

Tu, P., et al., "Genetic Disruption of Myostatin Reduces the Development of Proatherogenic Dyslipidemia and Atherogenic Lesions in Ldlr Null Mice," Diabetes, 58:1739-1748 (2009).

Ukkola, et al., "Adiponectin: A Link Between Excess Adiposity and Associated Comorbidities?", Journal of Molecular Medicine, 80(11):696-702 (2002).

Vallet, S., et al., "Activin A promotes multiple myeloma-induced osteolysis and is a promising target for myeloma bone disease," PNAS, 107(11):5124-5129 (2010).

Wagner, K.R., et al., "A Phase I/II trial of MYO-029 in Adult Subjects with Muscular Dystrophy," Ann. Neurol., 63:561-571 (2008).

Wagner, K.R., et al., "Loss of Myostatin Attenuates Severity of Muscular Dystrophy in mdx Mice," Ann. Neurol., 52:832-836 (2002).

Wagner, K.R., et al., "Muscle regeneration in the prolonged absence of myostatin," PNAS, 102(7):2519-2524 (2005).

Walsh, F. S, et al., "Myostatin: a modulator of skeletal-muscle stems cells," Biochemical Society Transactions, 33(Pt.6):1513-1517 (2005).

Weber, et al., A slient H-bond can by mutationally activated for high-affinity interaction of BMP-2 and activin type IIB receptor, BMC Structural Biology, 7(6):1-20 (2007).

Wells, J.A., "Additivity of Mutational Effects in Proteins," Biochemistry, 29(37):8509-8517 (1990).

Welt, et al., "Activin: an endocrine or panacrine agent?," European Journal of Endocrinology 139:469-471 (1998).

Wiater, et al., "Inhibin is an Antagonist of Bone Morphogenetic Protein Signaling," The Journal of Biological Chemistry, 278(10):7934-7941 (2003).

Wolfman, N.M., et al., "Activation of latent myostatin by the BMP-1/tolloid family of metalloproteinases," PNAS, 100(26):15842-15846 (2003).

Yokota, T., et al., "Isolation and characterization of a mouse cDNA clone that expresses mast-cell growth-factor activity in monkey cells," Proc. Natl. Acad. Sci. USA, 81:1070-1074 (1984).

Yu et al., "Specific roles of activin/inhibin in human erythropoiesis in vitro," Annals New York Academy of Sciences, 20(10):1243-1246 (1991).

Yu, J., et al., "Importance of FSH-releasing protein and inhibin in erythrodifferentiation," Nature, 330:765-767 (1987).

Zhao, B., et al., "Transgenic expression of myostatin propeptide prevents diet-induced obesity and insulin resistance," Biochemical and Biophysical Research Communications, 337:248-255 (2005).

Binkert, et al., "Cloning, sequence analysis and expression of a cDNA encoding a novel insulin-like growth factor binding protein (IGFBP-2)," The EMBO Journal, 8(9):2497-2502 (1989).

Caricasole, A. A. D., et al., "Human Growth-Differentiation Factor 3 (HGDF3): Developmental Regulation in Human Teratocarcinoma Cell Lines and Expression in Primary Testicular Germ Cell Tumours," Oncogene, 16:95-103 (1998).

Chamow, S.M., and Ashkenazi, A., "Immunoadhesins: Principles and Applications," TIBTECH, 14: 52-60 (1996).

Chapman, B., et al., "Effect of intron A from human cytomegalovirus (Towne) immediate-early gene on heterologous expression in mammalian cells," Nucleic Acids Research, 19(14):3979-3986 (1991).

Delogu, G., Et al., "DNA vaccine combinations expressing either tissue plasminogen activator signal sequence fusion proteins or ubiquitin-conjugated antigens induce sustained protective immunity in a mouse model of pulmonary tuberculosis," Infection and Immunity, 70(1):292-302 (2002).

DePaolo, L.V., et al., "Passive Immunoneutralization with a Monoclonal Antibody Reveals a Role for Endogenous Activin-B in Mediating FSH Hypersecretion during Estrus and Following Ovariectomy of Hypophysectomized, Pituitary-Grafted Rats," Endocrinology, 130(3):1741-1743 (1992).

Gilchrist, A., et al., "Antagonists of the Receptor-G Protein Interface Block Gi-coupled Signal Transduction," Journal of Biological Chemistry, The American Society of Biological Chemists, Inc., 273(24):14912-14919 (1998).

Greenwald, et al., "Characterization of the Extracellular Ligand-Binding Domain of the Type II Activin Receptor," Biochemistry, 37(47):16711-16718 (1998).

Lu, S., et al., "Simian Immunodeficiency Virus DNA Vaccine Trial in Macaques," Journal of Virology, 70(6):3978-3991 (1996).

Mathews, L.S., et al., "Expression Cloning of an Activin Receptor, a Predicted Transmembrane Serine Kinase," Cell, 65(6):973-982 (1991).

Matzuk et al., "Cloning of the human activin receptor cDNA reveals high evolutionary conservation," Biochim Biophys Acta, 1130(1):105-108 (1992).

McPherron, A.C., et al., "GDF-3 and GDF-9: Two New Members of the Transforming Growth Factor-B Superfamily Containing a Novel Pattern of Cysteines," Journal of Endocrinology, 268(5):3444-3449 (1993).

Murata, T., et al., "Anti-activin A Antibody (IgY) Specifically Neutralizes Various Activin A Activities," Proceedings of the Society for Experimental Biology & Medicine, 211(1):100-107 (1996).

Ruckle et al., "Single-Dose, Randomized, Double-Blind, Placebo-Controlled Study of ACE-011 (ACTRIIA-IgG1) in Postmenopausal Women," Journal of Bone and Mineral Research, vol. 24(4), pp. 744-752 (2009).

Schmelzer, C.H., et al., "Purification and Characterization of Recombinant Human Activin B," Biochimica et Biophysica Acta, 1039(2):135-141 (1990).

Thompson, T.B., et al., "Beta A versus beta B: is it merely a matter of express?," Molecular and Cellular Endocrinology, 225:9-17 (2004).

Tisdale, M.J., "Cachexia in Cancer Patients," Nat. Rev. Cancer, 2:862-871 (2002).

Wang, W., et al., "GDF-3 is an adipogenic cytokine under high fat dietary condition," Biochemical and Biophysical Research Comm., 321(4):1024-1031 (2004).

* cited by examiner

```
ActRIIa    ILGRSETQEC LFFNANWEKD RTNQTGVEPC YGDKDKRRHC FATWKNISGS
ActRIIb    GRGEAETREC IYYNANWELE RTNQSGLERC EGEQDKRLHC YASWRNSSGT

IEIVKQGCWL DDINCYDRTD CVEKKDSPEV YFCCCEGNMC NEKFSYFPEM
           IELVKKGCWL DDFNCYDRQE CVATEENPQV YFCCCEGNFC NERFTHLPEA

EVTQPTSNPV TPKPPT
           GGPEVTYEPP PTAPT
```

```
  1  MDAMKRGLCC VLLLCGAVFV SPGASGRGEA ETRECIYYNA NWELERTNQS
 51  GLERCEGEQD KRLHCYASWR NSSGTIELVK KGCWDDDFNC YDRQECVATE
101  ENPQVYFCCC EGNFCNERFT HLPEAGGPEV TYEPPPTAPT GGGTHTCPPC
151  PAPELLGGPS VFLFPPKPKD TLMISRTPEV TCVVVDVSHE DPEVKFNWYV
201  DGVEVHNAKT KPREEQYNST YRVVSVLTVL HQDWLNGKEY KCKVSNKALP
251  APIEKTISKA KGQPREPQVY TLPPSREEMT KNQVSLTCLV KGFYPSDIAV
301  EWESNGQPEN NYKTTPPVLD SDGSFFLYSK LTVDKSRWQQ GNVFSCSVMH
351  EALHNHYTQK SLSLSPGK
```

FIGURE 3

```
  1  ATGGATGCAA TGAAGAGAGG GCTCTGCTGT GTGCTGCTGC TGTGTGGAGC
     TACCTACGTT ACTTCTCTCC CGAGACGACA CACGACGACG ACACACCTCG

51  AGTCTTCGTT TCGCCCGGCG CCTCTGGGCG TGGGGAGGCT GAGACACGGG
     TCAGAAGCAA AGCGGGCCGC GGAGACCCGC ACCCCTCCGA CTCTGTGCCC

101  AGTGCATCTA CTACAACGCC AACTGGGAGC TGGAGCGCAC CAACCAGAGC
     TCACGTAGAT GATGTTGCGG TTGACCCTCG ACCTCGCGTG GTTGGTCTCG

151  GGCCTGGAGC GCTGCGAAGG CGAGCAGGAC AAGCGGCTGC ACTGCTACGC
     CCGGACCTCG CGACGCTTCC GCTCGTCCTG TTCGCCGACG TGACGATGCG

201  CTCCTGGCGC AACAGCTCTG CACCATCGA GCTCGTGAAG AAGGGCTGCT
     GAGGACCGCG TTGTCGAGAC CGTGGTAGCT CGAGCACTTC TTCCCGACGA

251  GGGATGATGA CTTCAACTGC TACGATAGGC AGGAGTGTGT GGCCACTGAG
     CCCTACTACT GAAGTTGACG ATGCTATCCG TCCTCACACA CCGGTGACTC

301  GAGAACCCCC AGGTGTACTT CTGCTGCTGT GAAGGCAACT TCTGCAACGA
     CTCTTGGGGG TCCACATGAA GACGACGACA CTTCCGTTGA AGACGTTGCT

351  GCGCTTCACT CATTTGCCAG AGGCTGGGGG CCCGGAAGTC ACGTACGAGC
     CGCGAAGTGA GTAAACGGTC TCCGACCCCC GGGCCTTCAG TGCATGCTCG

401  CACCCCCGAC AGCCCCCACC GGTGGTGGAA CTCACACATG CCCACCGTGC
     GTGGGGGCTG TCGGGGGTGG CCACCACCTT GAGTGTGTAC GGGTGGCACG

451  CCAGCACCTG AACTCCTGGG GGGACCGTCA GTCTTCCTCT TCCCCCCAAA
     GGTCGTGGAC TTGAGGACCC CCCTGGCAGT CAGAAGGAGA AGGGGGGTTT

501  ACCCAAGGAC ACCCTCATGA TCTCCCGGAC CCCTGAGGTC ACATGCGTGG
     TGGGTTCCTG TGGGAGTACT AGAGGGCCTG GGGACTCCAG TGTACGCACC

551  TGGTGGACGT GAGCCACGAA GACCCTGAGG TCAAGTTCAA CTGGTACGTG
     ACCACCTGCA CTCGGTGCTT CTGGGACTCC AGTTCAAGTT GACCATGCAC

601  GACGGCGTGG AGGTGCATAA TGCCAAGACA AAGCCGCGGG AGGAGCAGTA
     CTGCCGCACC TCCACGTATT ACGGTTCTGT TTCGGCGCCC TCCTCGTCAT

651  CAACAGCACG TACCGTGTGG TCAGCGTCCT CACCGTCCTG CACCAGGACT
     GTTGTCGTGC ATGGCACACC AGTCGCAGGA GTGGCAGGAC GTGGTCCTGA

701  GGCTGAATGG CAAGGAGTAC AAGTGCAAGG TCTCCAACAA AGCCCTCCCA
     CCGACTTACC GTTCCTCATG TTCACGTTCC AGAGGTTGTT TCGGGAGGGT

751  GCCCCCATCG AGAAAACCAT CTCCAAAGCC AAAGGGCAGC CCCGAGAACC
     CGGGGGTAGC TCTTTTGGTA GAGGTTTCGG TTTCCCGTCG GGGCTCTTGG
```

FIGURE 4

```
 801   ACAGGTGTAC ACCCTGCCCC CATCCCGGGA GGAGATGACC AAGAACCAGG
       TGTCCACATG TGGGACGGGG GTAGGGCCCT CCTCTACTGG TTCTTGGTCC

851   TCAGCCTGAC CTGCCTGGTC AAAGGCTTCT ATCCCAGCGA CATCGCCGTG
       AGTCGGACTG GACGGACCAG TTTCCGAAGA TAGGGTCGCT GTAGCGGCAC

901   GAGTGGGAGA GCAATGGGCA GCCGGAGAAC AACTACAAGA CCACGCCTCC
       CTCACCCTCT CGTTACCCGT CGGCCTCTTG TTGATGTTCT GGTGCGGAGG

951   CGTGCTGGAC TCCGACGGCT CCTTCTTCCT CTATAGCAAG CTCACCGTGG
       GCACGACCTG AGGCTGCCGA GGAAGAAGGA GATATCGTTC GAGTGGCACC

1001   ACAAGAGCAG GTGGCAGCAG GGGAACGTCT TCTCATGCTC CGTGATGCAT
       TGTTCTCGTC CACCGTCGTC CCCTTGCAGA AGAGTACGAG GCACTACGTA

1051   GAGGCTCTGC ACAACCACTA CACGCAGAAG AGCCTCTCCC TGTCCCCGGG
       CTCCGAGACG TGTTGGTGAT GTGCGTCTTC TCGGAGAGGG ACAGGGGCCC

1101   TAAATGA (SEQ ID NO:25)
       ATTTACT (SEQ ID NO:33)
```

FIGURE 4 CONT

```
  1    MDAMKRGLCC VLLLCGAVFV SPGAAETREC IYYNANWELE RTNQSGLERC

51    EGEQDKRLHC YASWRNSSGT IELVKKGCWD DDFNCYDRQE CVATEENPQV

101    YFCCCEGNFC NERFTHLPEA GGPEVTYEPP PTGGGTHTCP PCPAPELLGG

151    PSVFLFPPKP KDTLMISRTP EVTCVVVDVS HEDPEVKFNW YVDGVEVHNA

201    KTKPREEQYN STYRVVSVLT VLHQDWLNGK EYKCKVSNKA LPAPIEKTIS

251    KAKGQPREPQ VYTLPPSREE MTKNQVSLTC LVKGFYPSDI AVEWESNGQP

301    ENNYKTTPPV LDSDGSFFLY SKLTVDKSRW QQGNVFSCSV MHEALHNHYT

351    QKSLSLSPGK (SEQ ID NO: 26)
```

FIGURE 5

```
  1 ATGGATGCAA TGAAGAGAGG GCTCTGCTGT GTGCTGCTGC TGTGTGGAGC
    TACCTACGTT ACTTCTCTCC CGAGACGACA CACGACGACG ACACACCTCG

E   T   R   E   C   I   Y   Y
 51 AGTCTTCGTT TCGCCCGGCG CCGCTGAGAC ACGGGAGTGC ATCTACTACA
    TCAGAAGCAA AGCGGGCCGC GGCGACTCTG TGCCCTCACG TAGATGATGT

N   A   N   W   E   L   E   R   T   N   Q   S   G   L   E   R   C
101 ACGCCAACTG GGAGCTGGAG CGCACCAACC AGAGCGGCCT GGAGCGCTGC
    TGCGGTTGAC CCTCGACCTC GCGTGGTTGG TCTCGCCGGA CCTCGCGACG

E   G   E   Q   D   K   R   L   H   C   Y   A   S   W   R   N   S
151 GAAGGCGAGC AGGACAAGCG GCTGCACTGC TACGCCTCCT GGCGCAACAG
    CTTCCGCTCG TCCTGTTCGC CGACGTGACG ATGCGGAGGA CCGCGTTGTC

S   G   T   I   E   L   V   K   K   G   C   W   D   D   F
201 CTCTGGCACC ATCGAGCTCG TGAAGAAGGG CTGCTGGGAC GATGACTTCA
    GAGACCGTGG TAGCTCGAGC ACTTCTTCCC GACGACCCTG CTACTGAAGT

N   C   Y   D   R   Q   E   C   V   A   T   E   E   N   P   Q   V
251 ACTGCTACGA TAGGCAGGAG TGTGTGGCCA CTGAGGAGAA CCCCCAGGTG
    TGACGATGCT ATCCGTCCTC ACACACCGGT GACTCCTCTT GGGGGTCCAC

Y   F   C   C   E   G   N   F   C   N   E   R   F   T   H   L
301 TACTTCTGCT GCTGTGAAGG CAACTTCTGC AACGAGCGCT TCACTCATTT
    ATGAAGACGA CGACACTTCC GTTGAAGACG TTGCTCGCGA AGTGAGTAAA

P   E   A   G   G   P   E   V   T   Y   E   P   P   P   T
351 GCCAGAGGCT GGGGGCCCGG AAGTCACGTA CGAGCCACCC CCGACAGGTG
    CGGTCTCCGA CCCCCGGGCC TTCAGTGCAT GCTCGGTGGG GGCTGTCCAC

401 GTGGAACTCA CACATGCCCA CCGTGCCCAG CACCTGAACT CCTGGGGGGA
    CACCTTGAGT GTGTACGGGT GGCACGGGTC GTGGACTTGA GGACCCCCCT

451 CCGTCAGTCT TCCTCTTCCC CCCAAAACCC AAGGACACCC TCATGATCTC
    GGCAGTCAGA AGGAGAAGGG GGGTTTTGGG TTCCTGTGGG AGTACTAGAG

501 CCGGACCCCT GAGGTCACAT GCGTGGTGGT GGACGTGAGC CACGAAGACC
    GGCCTGGGGA CTCCAGTGTA CGCACCACCA CCTGCACTCG GTGCTTCTGG

551 CTGAGGTCAA GTTCAACTGG TACGTGGACG GCGTGGAGGT GCATAATGCC
    GACTCCAGTT CAAGTTGACC ATGCACCTGC CGCACCTCCA CGTATTACGG
```

FIGURE 6

```
 601   AAGACAAAGC CGCGGGAGGA GCAGTACAAC AGCACGTACC GTGTGGTCAG
       TTCTGTTTCG GCGCCCTCCT CGTCATGTTG TCGTGCATGG CACACCAGTC

651   CGTCCTCACC GTCCTGCACC AGGACTGGCT GAATGGCAAG GAGTACAAGT
       GCAGGAGTGG CAGGACGTGG TCCTGACCGA CTTACCGTTC CTCATGTTCA

701   GCAAGGTCTC CAACAAAGCC CTCCCAGCCC CCATCGAGAA AACCATCTCC
       CGTTCCAGAG GTTGTTTCGG GAGGGTCGGG GGTAGCTCTT TTGGTAGAGG

751   AAAGCCAAAG GGCAGCCCCG AGAACCACAG GTGTACACCC TGCCCCCATC
       TTTCGGTTTC CCGTCGGGGC TCTTGGTGTC CACATGTGGG ACGGGGGTAG

801   CCGGGAGGAG ATGACCAAGA ACCAGGTCAG CCTGACCTGC CTGGTCAAAG
       GGCCCTCCTC TACTGGTTCT TGGTCCAGTC GGACTGGACG GACCAGTTTC

851   GCTTCTATCC CAGCGACATC GCCGTGGAGT GGGAGAGCAA TGGGCAGCCG
       CGAAGATAGG GTCGCTGTAG CGGCACCTCA CCCTCTCGTT ACCCGTCGGC

901   GAGAACAACT ACAAGACCAC GCCTCCCGTG CTGGACTCCG ACGGCTCCTT
       CTCTTGTTGA TGTTCTGGTG CGGAGGGCAC GACCTGAGGC TGCCGAGGAA

951   CTTCCTCTAT AGCAAGCTCA CCGTGGACAA GAGCAGGTGG CAGCAGGGGA
       GAAGGAGATA TCGTTCGAGT GGCACCTGTT CTCGTCCACC GTCGTCCCCT

1001   ACGTCTTCTC ATGCTCCGTG ATGCATGAGG CTCTGCACAA CCACTACACG
       TGCAGAAGAG TACGAGGCAC TACGTACTCC GAGACGTGTT GGTGATGTGC

1051   CAGAAGAGCC TCTCCCTGTC CCCGGGTAAA TGA (SEQ ID NO: 27)
       GTCTTCTCGG AGAGGGACAG GGGCCCATTT ACT (SEQ ID NO: 34)
```

FIGURE 6 CONT

```
  1  ETRECIYYNA NWELERTNQS GLERCEGEQD KRLHCYASWR NSSGTIELVK
 51  KGCWDDDFNC YDRQECVATE ENPQVYFCCC EGNFCNERFT HLPEAGGPEV
101  TYEPPPTGGG THTCPPCPAP ELLGGPSVFL FPPKPKDTLM ISRTPEVTCV
151  VVDVSHEDPE VKFNWYVDGV EVHNAKTKPR EEQYNSTYRV VSVLTVLHQD
201  WLNGKEYKCK VSNKALPAPI EKTISKAKGQ PREPQVYTLP PSREEMTKNQ
251  VSLTCLVKGF YPSDIAVEWE SNGQPENNYK TTPPVLDSDG SFFLYSKLTV
301  DKSRWQQGNV FSCSVMHEAL HNHYTQKSLS LSPGK (SEQ ID NO: 28)
```

FIGURE 7

```
  1   ETRECIYYNA NWELERTNQS GLERCEGEQD KRLHCYASWR NSSGTIELVK

51   KGCWDDDFNC YDRQECVATE ENPQVYFCCC EGNFCNERFT HLPEAGGPEV

101   TYEPPPT   (SEQ ID NO: 29)
```

FIGURE 8

```
  1  ATGGATGCAA TGAAGAGAGG GCTCTGCTGT GTGCTGCTGC TGTGTGGAGC
     TACCTACGTT ACTTCTCTCC CGAGACGACA CACGACGACG ACACACCTCG

E  T   R  E  C   I  Y  Y
 51  AGTCTTCGTT TCGCCCGGCG CCGCCGAAAC CCGCGAATGT ATTTATTACA
     TCAGAAGCAA AGCGGGCCGC GGCGGCTTTG GGCGCTTACA TAAATAATGT

N  A  N  W   E  L  E   R  T  N   Q  S  G   L  E  R  C
101  ATGCTAATTG GGAACTCGAA CGGACGAACC AATCCGGGCT CGAACGGTGT
     TACGATTAAC CCTTGAGCTT GCCTGCTTGG TTAGGCCCGA GCTTGCCACA

E  G  E   Q  D  K  R   L  H  C   Y  A  S   W  R  N  S
151  GAGGGGGAAC AGGATAAACG CCTCCATTGC TATGCGTCGT GGAGGAACTC
     CTCCCCCTTG TCCTATTTGC GGAGGTAACG ATACGCAGCA CCTCCTTGAG

S  G  T   I  E  L   V  K  K   C  W  D   D  D  F
201  CTCCGGGACG ATTGAACTGG TCAAGAAAGG GTGCTGGGAC GACGATTTCA
     GAGGCCCTGC TAACTTGACC AGTTCTTTCC CACGACCCTG CTGCTAAAGT

N  C  Y  D   R  Q  E   C  V  A   T  E  E   N  P  Q  V
251  ATTGTTATGA CCGCCAGGAA TGTGTCGCGA CCGAAGAGAA TCCGCAGGTC
     TAACAATACT GGCGGTCCTT ACACAGCGCT GGCTTCTCTT AGGCGTCCAG

Y  F  C   C  C  E  G   N  F  C   N  E  R   F  T  H  L
301  TATTTCTGTT GTTGCGAGGG GAATTTCTGT AATGAACGGT TTACCCACCT
     ATAAAGACAA CAACGCTCCC CTTAAAGACA TTACTTGCCA AATGGGTGGA

P  E  A   G  G  P   E  V  T  Y   E  P  P   P  T
351  CCCCGAAGCC GGCGGGCCCG AGGTGACCTA TGAACCCCCG CCCACCGGTG
     GGGGCTTCGG CCGCCCGGGC TCCACTGGAT ACTTGGGGGC GGGTGGCCAC

401  GTGGAACTCA CACATGCCCA CCGTGCCCAG CACCTGAACT CCTGGGGGGA
     CACCTTGAGT GTGTACGGGT GGCACGGGTC GTGGACTTGA GGACCCCCCT

451  CCGTCAGTCT TCCTCTTCCC CCCAAAACCC AAGGACACCC TCATGATCTC
     GGCAGTCAGA AGGAGAAGGG GGGTTTTGGG TTCCTGTGGG AGTACTAGAG

501  CCGGACCCCT GAGGTCACAT GCGTGGTGGT GGACGTGAGC CACGAAGACC
     GGCCTGGGGA CTCCAGTGTA CGCACCACCA CCTGCACTCG GTGCTTCTGG

551  CTGAGGTCAA GTTCAACTGG TACGTGGACG GCGTGGAGGT GCATAATGCC
     GACTCCAGTT CAAGTTGACC ATGCACCTGC CGCACCTCCA CGTATTACGG

601  AAGACAAAGC CGCGGGAGGA GCAGTACAAC AGCACGTACC GTGTGGTCAG
     TTCTGTTTCG GCGCCCTCCT CGTCATGTTG TCGTGCATGG CACACCAGTC

651  CGTCCTCACC GTCCTGCACC AGGACTGGCT GAATGGCAAG GAGTACAAGT
     GCAGGAGTGG CAGGACGTGG TCCTGACCGA CTTACCGTTC CTCATGTTCA
```

FIGURE 9

```
701    GCAAGGTCTC CAACAAAGCC CTCCCAGCCC CCATCGAGAA AACCATCTCC
       CGTTCCAGAG GTTGTTTCGG GAGGGTCGGG GGTAGCTCTT TTGGTAGAGG

751    AAAGCCAAAG GGCAGCCCCG AGAACCACAG GTGTACACCC TGCCCCCATC
       TTTCGGTTTC CCGTCGGGGC TCTTGGTGTC CACATGTGGG ACGGGGGTAG

801    CCGGGAGGAG ATGACCAAGA ACCAGGTCAG CCTGACCTGC CTGGTCAAAG
       GGCCCTCCTC TACTGGTTCT TGGTCCAGTC GGACTGGACG GACCAGTTTC

851    GCTTCTATCC CAGCGACATC GCCGTGGAGT GGGAGAGCAA TGGGCAGCCG
       CGAAGATAGG GTCGCTGTAG CGGCACCTCA CCCTCTCGTT ACCCGTCGGC

901    GAGAACAACT ACAAGACCAC GCCTCCCGTG CTGGACTCCG ACGGCTCCTT
       CTCTTGTTGA TGTTCTGGTG CGGAGGGCAC GACCTGAGGC TGCCGAGGAA

951    CTTCCTCTAT AGCAAGCTCA CCGTGGACAA GAGCAGGTGG CAGCAGGGGA
       GAAGGAGATA TCGTTCGAGT GGCACCTGTT CTCGTCCACC GTCGTCCCCT

1001   ACGTCTTCTC ATGCTCCGTG ATGCATGAGG CTCTGCACAA CCACTACACG
       TGCAGAAGAG TACGAGGCAC TACGTACTCC GAGACGTGTT GGTGATGTGC

1051   CAGAAGAGCC TCTCCCTGTC CCCGGGTAAA TGA  (SEQ ID NO: 30)
       GTCTTCTCGG AGAGGGACAG GGGCCCATTT ACT  (SEQ ID NO: 35)
```

FIGURE 9 CONT

```
     GAAAC CCGCGAATGT ATTTATTACA ATGCTAATTG GGAACTCGAA CGGACGAACC
AATCCGGGCT CGAACGGTGT GAGGGGGAAC AGGATAAACG CCTCCATTGC TATGCGTCGT
GGAGGAACTC CTCCGGGACG ATTGAACTGG TCAAGAAAGG GTGCTGGGAC GACGATTTCA
ATTGTTATGA CCGCCAGGAA TGTGTCGCGA CCGAAGAGAA TCCGCAGGTC TATTTCTGTT
GTTGCGAGGG GAATTTCTGT AATGAACGGT TTACCCACCT CCCCGAAGCC GGCGGGCCCG
AGGTGACCTA TGAACCCCCG CCCACC    (SEQ ID NO: 31)
```

FIGURE 10

600;
METHODS FOR INCREASING RED BLOOD CELL LEVELS AND TREATING ANEMIA USING A COMBINATION OF GDF TRAPS AND ERYTHROPOIETIN RECEPTOR ACTIVATORS

RELATED APPLICATIONS

This application is a continuation-in-part of U.S. application Ser. No. 12/583,177 and International Application Serial No. PCT/US2009/004659, both filed on Aug. 13, 2009. This application also claims the benefit of Provisional Application Ser. No. 61/305,901, filed Feb. 18, 2010. All the teachings of the above-referenced applications are incorporated herein by reference.

SEQUENCE LISTING

The instant application contains a Sequence Listing, which has been submitted via EFS-Web and is hereby incorporated by reference in its entirety. Said ASCII copy, created on Oct. 20, 2010 is named PHPH040102.txt and is 70,997 bytes in size.

BACKGROUND OF THE INVENTION

The mature red blood cell, or erythrocyte, is responsible for oxygen transport in the circulatory systems of vertebrates. Red blood cells contain high concentrations of hemoglobin, a protein that binds oxygen in the lungs at relatively high partial pressure of oxygen ($pO_2$) and delivers oxygen to areas of the body with a relatively low $pO_2$.

Mature red blood cells are produced from pluripotent hematopoietic stem cells in a process termed erythropoiesis. Postnatal erythropoiesis occurs primarily in the bone marrow and in the red pulp of the spleen. The coordinated action of various signaling pathways control the balance of cell proliferation, differentiation, survival and death. Under normal conditions, red blood cells are produced at a rate that maintains a constant red cell mass in the body, and production may increase or decrease in response to various stimuli, including increased or decreased oxygen tension or tissue demand. The process of erythropoiesis begins with the formation of lineage committed precursor cells and proceeds through a series of distinct precursor cell types. The final stages of erythropoiesis occur as reticulocytes are released into the bloodstream and lose their mitochondria and ribosomes while assuming the morphology of mature red blood cell. An elevated level of reticulocytes, or an elevated reticulocyte:erythrocyte ratio, in the blood is indicative of increased red blood cell production rates.

Erythropoietin (EPO) is widely recognized as the most significant positive regulator of postnatal erythropoiesis in vertebrates. EPO regulates the compensatory erythropoietic response to reduced tissue oxygen tension (hypoxia) and low red blood cell levels or low hemoglobin levels. In humans, elevated EPO levels promote red blood cell formation by stimulating the generation of erythroid progenitors in the bone marrow and spleen. In the mouse, EPO enhances erythropoiesis primarily in the spleen.

Effects of EPO are mediated by a cell-surface receptor belonging to the cytokine receptor superfamily. The human EPO receptor gene encodes a 483 amino-acid transmembrane protein, whereas the active EPO receptor is thought to exist as a multimeric complex even in the absence of ligand (See U.S. Pat. No. 6,319,499). The cloned full-length EPO receptor expressed in mammalian cells binds EPO with an affinity similar to that of the native receptor on erythroid progenitor cells. Binding of EPO to its receptor causes a conformational change resulting in receptor activation and biological effects including increased proliferation of immature erythroblasts, increased differentiation of immature erythroblasts, and decreased apoptosis in erythroid progenitor cells (Liboi et al., 1993, Proc Natl Acad Sci USA 90:11351-11355; Koury et al., 1990, Science 248:378-381).

Various forms of recombinant EPO are used by physicians to increase red blood cell levels in a variety of clinical settings, and particularly for the treatment of anemia. Anemia is a broadly-defined condition characterized by lower than normal levels of hemoglobin or red blood cells in the blood. In some instances, anemia is caused by a primary disorder in the production or survival of red blood cells. More commonly, anemia is secondary to diseases of other systems (Weatherall & Provan (2000) Lancet 355, 1169-1175). Anemia may result from a reduced rate of production or increased rate of destruction of red blood cells or by loss of red blood cells due to bleeding. Anemia may result from a variety of disorders that include, for example, chronic renal failure, chemotherapy treatment, myelodysplastic syndrome, rheumatoid arthritis, and bone marrow transplantation.

Treatment with EPO typically causes a rise in hemoglobins by about 1-3 g/dL in healthy humans over a period of weeks. When administered to anemic individuals, this treatment regimen often provides substantial increases in hemoglobin and red blood cell levels and leads to improvements in quality of life and prolonged survival. EPO is not uniformly effective, and many individuals are refractory to even high doses (Horl et al. (2000) Nephrol Dial Transplant 15, 43-50). Over 50% of patients with cancer have an inadequate response to EPO, approximately 10% with end-stage renal disease are hyporesponsive (Glaspy et al. (1997) J Clin Oncol 15, 1218-1234; Demetri et al. (1998) J Clin Oncol 16, 3412-3425), and less than 10% with myelodysplastic syndrome respond favorably (Estey (2003) Curr Opin Hematol 10, 60-67). Several factors, including inflammation, iron and vitamin deficiency, inadequate dialysis, aluminum toxicity, and hyperparathyroidism may predict a poor therapeutic response. The molecular mechanisms of resistance to EPO are as yet unclear. Recent evidence suggests that higher doses of EPO may be associated with an increased risk of cardiovascular morbidity, tumor growth, and mortality in some patient populations (Krapf et al., 2009, Clin J Am Soc Nephrol 4:470-480; Glaspy, 2009, Annu Rev Med 60:181-192). It has therefore been recommended that EPO-based therapeutic compounds (erythropoietin-stimulating agents, ESAs) be administered at the lowest dose sufficient to avoid the need for red blood cell transfusions (Jelkmann et al., 2008, Crit. Rev Oncol. Hematol 67:39-61).

Thus, it is an object of the present disclosure to provide alternative methods for increasing red blood cell levels in patients, which would permit use of reduced doses of erythropoietin receptor activators.

SUMMARY OF THE INVENTION

In part, the disclosure demonstrates that GDF Traps may be used in combination (e.g., administered at the same time or different times, but generally in such a manner as to achieve overlapping pharmacological effects) with EPO receptor activators to increase red blood cell levels (erythropoiesis) or treat anemia in patients in need thereof. In part, the disclosure demonstrates that a GDF Trap can be administered in combination with an EPO receptor activator to synergistically increase formation of red blood cells in a patient. Thus, the effect of this combined treatment can be significantly greater than the sum of the effects of the GDF Trap and the EPO receptor activator when administered separately at their respective doses. In certain embodiments, this synergism may be advantageous since it enables target levels of red blood cells to be attained with lower doses of an EPO receptor activator, thereby avoiding potential adverse effects or other problems associated with higher levels of EPO receptor activation.

An EPO receptor activator may stimulate erythropoiesis by directly contacting and activating EPO receptor. In certain embodiments, the EPO receptor activator is one of a class of compounds based on the 165 amino-acid sequence of native EPO and generally known as erythropoiesis-stimulating agents (ESAs), examples of which are epoetin alfa, epoetin beta, epoetin delta, and epoetin omega. In other embodiments, ESAs include synthetic EPO proteins (SEPs) and EPO derivatives with nonpeptidic modifications conferring desirable pharmacokinetic properties (lengthened circulating half-life), examples of which are darbepoetin alfa and methoxy-polyethylene-glycol epoetin beta. In certain embodiments, an EPO receptor activator may be an EPO receptor agonist that does not incorporate the EPO polypeptide backbone or is not generally classified as an ESA. Such EPO receptor agonists may include, but are not limited to, peptidic and nonpeptidic mimetics of EPO, agonistic antibodies targeting EPO receptor, fusion proteins comprising an EPO mimetic domain, and erythropoietin receptor extended-duration limited agonists (EREDLA).

In certain embodiments, an EPO receptor activator may stimulate erythropoiesis indirectly, without contacting EPO receptor itself, by enhancing production of endogenous EPO. For example, hypoxia-inducible transcription factors (HIFs) are endogenous stimulators of EPO gene expression that are suppressed (destabilized) under normoxic conditions by cellular regulatory mechanisms. In part, the disclosure provides increased erythropoiesis in a patient by combined treatment with a GDF Trap and an indirect EPO receptor activator with HIF stabilizing properties, such as a prolyl hydroxylase inhibitor.

Variant ActRIIB polypeptides having a significantly decreased affinity for activin (e.g., activin A and/or activin B) relative to other ActRIIB ligands, such as GDF11 and/or myostatin, are referred to as GDF Traps. ActRIIB variants described herein are GDF Traps unless otherwise stated. In particular, the disclosure demonstrates that a GDF Trap which is a soluble form of ActRIIB polypeptide having an acidic residue at position 79 of SEQ ID NO: 1, when administered in vivo, increases red blood cell levels in the blood. Therefore, in certain embodiments, the disclosure provides methods for using GDF Traps to increase red blood cell and hemoglobin levels in patients and to treat disorders associated with low red blood cell or hemoglobin levels in patients in need thereof. As described in U.S. patent application Ser. No. 12/012,652, incorporated by reference herein, GDF Traps can be used to increase muscle mass and decrease fat mass.

In certain aspects, the present disclosure provides GDF Traps that are variant ActRIIB polypeptides, including ActRIIB polypeptides having amino- and carboxy-terminal truncations and sequence alterations. Optionally, GDF Traps of the invention may be designed to preferentially antagonize one or more ligands of ActRIIB receptors, such as GDF8 (also called myostatin), GDF11, Nodal, and BMP7 (also called OP-1). Examples of GDF Traps include a set of variants derived from ActRIIB that have greatly diminished affinity for activin. These variants exhibit desirable effects on red blood cells while reducing effects on other tissues. Examples of such variants include those having an acidic amino acid (e.g., aspartic acid, D, or glutamic acid, E) at the position corresponding to position 79 of SEQ ID NO.1. In certain embodiments, the GDF Trap polypeptide comprises an amino acid sequence that comprises, consists of, or consists essentially of, the amino acid sequence of SEQ ID NO: 7, 26, 28, 29, 32, 37 or 38, and polypeptides that are at least 80%, 85%, 90%, 95%, 97%, 98%, or 99% identical to any of the foregoing.

In certain aspects, the disclosure provides pharmaceutical preparations comprising a GDF Trap that binds to an ActRIIB ligand such as GDF8, GDF11, activin (e.g., activin B), BMP7 or nodal, and a pharmaceutically acceptable carrier. Optionally, the GDF Trap binds to an ActRIIB ligand with a Kd less than 10 micromolar, less than 1 micromolar, less than 100 nanomolar, less than 10 nanomolar, or less than 1 nanomolar. Optionally, the GDF Trap inhibits ActRIIB signaling, such as intracellular signal transduction events triggered by an ActRIIB ligand. A GDF Trap for use in such a preparation may be any of those disclosed herein, including, for example, GDF Traps having an amino acid sequence selected from SEQ ID NOs: 2, 3, 7, 11, 26, 28, 29, 32, 37, 38 or 40, or GDF Traps having an amino acid sequence that is at least 80%, 85%, 90%, 95%, 97% or 99% identical to an amino acid sequence selected from SEQ ID NOs: 2, 3, 7, 11, 26, 28, 29, 32, 37, 38 or 40, or GDF Traps having an amino acid sequence that is at least 80%, 85%, 90%, 95%, 97% or 99% identical to an amino acid sequence selected from SEQ ID NOs: 2, 3, 7, 11, 26, 28, 29, 32, 37, 38 or 40 wherein the position corresponding to L79 in SEQ ID NO: 1 is an acidic amino acid. A preferred GDF Trap for use in such a preparation consists of, or consists essentially of, the amino acid sequence of SEQ ID NO: 26. A GDF Trap may include a functional fragment of a natural ActRIIB polypeptide, such as one comprising at least 10, 20 or 30 amino acids of a sequence selected from SEQ ID NOs: 2, 3, 7, 11, 26, 28, 29, 32, 37, 38 or 40 or a sequence of SEQ ID NO: 2, lacking the C-terminal 1, 2, 3, 4, 5 or 10 to 15 amino acids and lacking 1, 2, 3, 4 or 5 amino acids at the N-terminus. A preferred polypeptide will comprise a truncation relative to SEQ ID NO: 2 or 40 of between 2 and 5 amino acids at the N-terminus and no more than 3 amino acids at the C-terminus. A GDF Trap may include one or more alterations in the amino acid sequence of an ActRIIB polypeptide (e.g., in the ligand-binding domain) relative to a naturally occurring ActRIIB polypeptide. The alteration in the amino acid sequence may, for example, alter glycosylation of the polypeptide when produced in a mammalian, insect or other eukaryotic cell or alter proteolytic cleavage of the polypeptide relative to the naturally occurring ActRIIB polypeptide.

A GDF Trap may be a fusion protein that has, as one domain, an ActRIIB polypeptide (e.g., a ligand-binding domain of an ActRIIB with one or more sequence variations) and one or more additional domains that provide a desirable property, such as improved pharmacokinetics, easier purification, targeting to particular tissues, etc. For example, a domain of a fusion protein may enhance one or more of in vivo stability, in vivo half life, uptake/administration, tissue localization or distribution, formation of protein complexes, multimerization of the fusion protein, and/or purification. GDF Trap fusion proteins may include an immunoglobulin Fc domain (wild-type or mutant) or a serum albumin. In certain embodiments, a GDF Trap fusion comprises a relatively unstructured linker positioned between the Fc domain and the extracellular ActRIIB domain. This unstructured linker may correspond to the roughly 15 amino acid unstructured region at the C-terminal end of the extracellular domain of ActRIIB (the "tail"), or it may be an artificial sequence of between 3 and 5, 15, 20, 30, 50 or more amino acids that are relatively free of secondary structure. A linker may be rich in glycine and proline residues and may, for example, contain repeating sequences of threonine/serine and glycines (e.g., $TG_4$ (SEQ ID NO: 13) or $SG_4$ (SEQ ID NO: 14) singlets or repeats) or a series of three glycines. A fusion protein may include a purification subsequence, such as an epitope tag, a FLAG tag, a polyhistidine sequence, and a GST fusion. In certain embodiments, a GDF Trap fusion comprises a leader sequence. The leader sequence may be a native ActRIIB leader sequence or a heterologous leader sequence. In certain embodiments, the leader sequence is a Tissue Plasminogen Activator (TPA) leader sequence. In an embodiment, a GDF Trap fusion protein comprises an amino acid sequence as set forth in the formula A-B-C. The B portion is an N- and C-terminally truncated ActRIIB polypeptide consisting of the amino acid sequence corresponding to amino acids 25-131 of SEQ ID NO: 2 or 40. The A and C portions may be independently zero, one or more than one amino acids, and both A and C portions are heterologous to B. The A and/or C portions may be attached to the B portion via a linker sequence.

Optionally, a GDF Trap includes a variant ActRIIB polypeptide having one or more modified amino acid residues selected from: a glycosylated amino acid, a PEGylated amino acid, a farnesylated amino acid, an acetylated amino acid, a biotinylated amino acid, an amino acid conjugated to a lipid moiety, and an amino acid conjugated to an organic derivatizing agent. A pharmaceutical preparation may also include one or more additional compounds such as a compound that is used to treat an ActRIIB-associated disorder. Preferably, a pharmaceutical preparation is substantially pyrogen free. In general, it is preferable that a GDF Trap be expressed in a mammalian cell line that mediates suitably natural glycosylation of the GDF Trap so as to diminish the likelihood of an unfavorable immune response in a patient. Human and CHO cell lines have been used successfully, and it is expected that other common mammalian expression vectors will be useful.

In certain aspects, the disclosure provides packaged pharmaceuticals comprising a pharmaceutical preparation described herein and labeled for use in increasing red blood cell levels in a human.

In certain aspects, the disclosure provides GDF Traps which are soluble ActRIIB polypeptides comprising an altered ligand-binding (e.g., GDF8-binding) domain. GDF Traps with altered ligand-binding domains may comprise, for example, one or more mutations at amino acid residues such as E37, E39, R40, K55, R56, Y60, A64, K74, W78, L79, D80, F82 and F101 of human ActRIIB (numbering is relative to SEQ ID NO: 1). Optionally, the altered ligand-binding domain can have increased selectivity for a ligand such as GDF8/GDF11 relative to a wild-type ligand-binding domain of an ActRIIB receptor. To illustrate, these mutations are demonstrated herein to increase the selectivity of the altered ligand-binding domain for GDF11 (and therefore, presumably, GDF8) over activin: K74Y, K74F, K74I, L79D, L79E, and D80I. The following mutations have the reverse effect, increasing the ratio of activin binding over GDF11:D54A, K55A, L79A and F82A. The overall (GDF11 and activin) binding activity can be increased by inclusion of the "tail" region or, presumably, an unstructured linker region, and also by use of a K74A mutation. Other mutations that caused an overall decrease in ligand binding affinity, include: R40A, E37A, R56A, W78A, D80K, D80R, D80A, D80G, D80F, D80M and D80N. Mutations may be combined to achieve desired effects. For example, many of the mutations that affect the ratio of GDF11:Activin binding have an overall negative effect on ligand binding, and therefore, these may be combined with mutations that generally increase ligand binding to produce an improved binding protein with ligand selectivity. In an exemplary embodiment, a GDF Trap is an ActRIIB polypeptide comprising an L79D or L79E mutation, optionally in combination with additional amino acid substitutions, additions or deletions.

Optionally, a GDF Trap comprising an altered ligand-binding domain has a ratio of $K_d$ for activin binding to $K_d$ for GDF8 binding that is at least 2, 5, 10, or even 100 fold greater relative to the ratio for the wild-type ligand-binding domain. Optionally, the GDF Trap comprising an altered ligand-binding domain has a ratio of $IC_{50}$ for inhibiting activin to $IC_{50}$ for inhibiting GDF8/GDF11 that is at least 2, 5, 10, or even 100 fold greater relative to the wild-type ActRIIB ligand-binding domain. Optionally, the GDF Trap comprising an altered ligand-binding domain inhibits GDF8/GDF11 with an $IC_{50}$ at least 2, 5, 10, or even 100 times less than the $IC_{50}$ for inhibiting activin. These GDF Traps can be fusion proteins that include an immunoglobulin Fc domain (either wild-type or mutant). In certain cases, the subject soluble GDF Traps are antagonists (inhibitors) of GDF8 and/or GDF11.

Other GDF Traps are contemplated, such as the following. A GDF Trap fusion protein comprising a portion derived from the ActRIIB sequence of SEQ ID NO: 1 or 39 and a second polypeptide portion, wherein the portion derived from ActRIIB corresponds to a sequence beginning at any of amino acids 21-29 of SEQ ID NO: 1 or 39 (optionally beginning at 22-25 of SEQ ID NO: 1 or 39) and ending at any of amino acids 109-134 of SEQ ID NO: 1 or 39, and wherein the GDF Trap fusion protein inhibits signaling by activin, myostatin and/or GDF11 in a cell-based assay. The GDF Trap fusion protein above, wherein the portion derived from ActRIIB corresponds to a sequence beginning at any of amino acids 20-29 of SEQ ID NO: 1 or 39 (optionally beginning at 22-25 of SEQ ID NO: 1 or 39) and ending at any of amino acids 109-133 of SEQ ID NO: 1 or 39. The GDF Trap fusion protein above, wherein the portion derived from ActRIIB corresponds to a sequence beginning at any of amino acids 20-24 of SEQ ID NO: 1 or 39 (optionally beginning at 22-25 of SEQ ID NO: 1 or 39) and ending at any of amino acids 109-133 of SEQ ID NO: 1 or 39. The GDF Trap fusion protein above, wherein the portion derived from ActRIIB corresponds to a sequence beginning at any of amino acids 21-24 of SEQ ID NO: 1 or 39 and ending at any of amino acids 109-134 of SEQ ID NO: 1 or 39. The GDF Trap fusion protein above, wherein the portion derived from ActRIIB corresponds to a sequence beginning at any of amino acids 20-24 of SEQ ID NO: 1 or 39 and ending at any of amino acids 118-133 of SEQ ID NO: 1 or 39. The GDF Trap fusion protein above, wherein the portion derived from ActRIIB corresponds to a sequence beginning at any of amino acids 21-24 of SEQ ID NO: 1 or 39 and ending at any of amino acids 118-134 of SEQ ID NO: 1 or 39. The GDF Trap fusion protein above, wherein the portion derived from ActRIIB corresponds to a sequence beginning at any of amino acids 20-24 of SEQ ID NO: 1 or 39 and ending at any of amino acids 128-133 of SEQ ID NO: 1 or 39. The GDF Trap fusion protein above, wherein the portion derived from ActRIIB corresponds to a sequence beginning at any of amino acids 20-24 of SEQ ID NO: 1 or 39 and ending at any of amino acids 128-133 of SEQ ID NO: 1 or 39. The GDF Trap fusion protein above, wherein the portion derived from ActRIIB corresponds to a sequence beginning at any of amino acids 21-29 of SEQ ID NO: 1 or 39 and ending at any of amino acids 118-134 of SEQ ID NO: 1 or 39. The GDF Trap fusion protein above, wherein the portion derived from ActRIIB corresponds to a sequence beginning at any of amino acids 20-29 of SEQ ID NO: 1 or 39 and ending at any of amino acids 118-133 of SEQ ID NO: 1 or 39. The GDF Trap fusion protein above, wherein the portion derived from ActRIIB corresponds to a sequence beginning at any of amino acids 21-29 of SEQ ID NO: 1 or 39 and ending at any of amino acids 128-134 of SEQ ID NO: 1 or 39. The GDF Trap fusion protein above, wherein the portion derived from ActRIIB corresponds to a sequence beginning at any of amino acids 20-29 of SEQ ID NO: 1 and ending at any of amino acids 128-133 of SEQ ID NO: 1 or 39. Surprisingly, constructs beginning at 22-25 of SEQ ID NO: 1 or 39 have activity levels greater than proteins having the full extracellular domain of human ActRIIB In a preferred embodiment, the GDF Trap fusion protein comprises, consists essentially of, or consists of, an amino acid sequence beginning at amino acid position 25 of SEQ ID NO: 1 or 39 and ending at amino acid position 131 of SEQ ID NO: 1 or 39. In another preferred embodiments, the GDF Trap polypeptide consists of, or consists essentially of, the amino acid sequence of SEQ ID NO: 7, 26, 28, 29, 32, 37 or 38. Any of the above GDF Trap fusion proteins may be produced as a homodimer. Any of the above GDF Trap fusion proteins may have a heterologous portion that comprises a constant region from an IgG heavy chain, such as an Fc domain. Any of the above GDF Trap fusion proteins may comprise an acidic amino acid at the position corresponding to position 79 of SEQ ID NO: 1, optionally in combination with one or more additional amino acid substitutions, deletions or insertions relative to SEQ ID NO: 1.

Other GDF Trap proteins are contemplated, such as the following. A GDF Trap protein comprising an amino acid sequence that is at least 80% identical to the sequence of amino acids 29-109 of SEQ ID NO: 1 or 39, wherein the position corresponding to 64 of SEQ ID NO: 1 is an R or K, and wherein the GDF Trap protein inhibits signaling by activin, myostatin and/or GDF11 in a cell-based assay. The GDF Trap protein above, wherein at least one alteration with respect to the sequence of SEQ ID NO: 1 or 39 is positioned outside of the ligand binding pocket. The GDF Trap protein above, wherein at least one alteration with respect to the sequence of SEQ ID NO: 1 or 39 is a conservative alteration positioned within the ligand binding pocket. The GDF Trap protein above, wherein at least one alteration with respect to the sequence of SEQ ID NO: 1 or 39 is an alteration at one or more positions selected from the group consisting of K74, R40, Q53, K55, F82 and L79. The GDF Trap protein above, wherein the protein comprises at least one N-X-S/T sequence at a position other than an endogenous N-X-S/T sequence of ActRIIB, and at a position outside of the ligand binding pocket.

Other GDF Traps are contemplated, such as the following. A GDF Trap protein comprising an amino acid sequence that is at least 80% identical to the sequence of amino acids 29-109 of SEQ ID NO: 1 or 39, and wherein the protein comprises at least one N-X-S/T sequence at a position other than an endogenous N-X-S/T sequence of ActRIIB, and at a position outside of the ligand binding pocket. The GDF Trap above, wherein the GDF Trap protein comprises an N at the position corresponding to position 24 of SEQ ID NO: 1 or 39 and an S or T at the position corresponding to position 26 of SEQ ID NO: 1 or 39, and wherein the GDF Trap inhibits signaling by activin, myostatin and/or GDF11 in a cell-based assay. The GDF Trap above, wherein the GDF Trap protein comprises an R or K at the position corresponding to position 64 of SEQ ID NO: 1 or 39. The GDF Trap above, wherein the ActRIIB protein comprises a D or E at the position corresponding to position 79 of SEQ ID NO: 1 or 39 and wherein the GDF Trap inhibits signaling by activin, myostatin and/or GDF11 in a cell-based assay. The GDF Trap above, wherein at least one alteration with respect to the sequence of SEQ ID NO: 1 or 39 is a conservative alteration positioned within the ligand binding pocket. The GDF Trap above, wherein at least one alteration with respect to the sequence of SEQ ID NO: 1 or 39 is an alteration at one or more positions selected from the group consisting of K74, R40, Q53, K55, F82 and L79. The GDF Trap above, wherein the protein is a fusion protein further comprising a heterologous portion. Any of the above GDF Trap fusion proteins may be produced as a homodimer. Any of the above GDF Trap fusion proteins may have a heterologous portion that comprises a constant region from an IgG heavy chain, such as an Fc domain.

In certain aspects, the disclosure provides nucleic acids encoding a GDF Trap polypeptide. An isolated polynucleotide may comprise a coding sequence for a soluble GDF Trap polypeptide, such as described above. For example, an isolated nucleic acid may include a sequence coding for a GDF Trap comprising an extracellular domain (e.g., ligand-binding domain) of an ActRIIB polypeptide having one or more sequence variations and a sequence that would code for part or all of the transmembrane domain and/or the cytoplasmic domain of an ActRIIB polypeptide, but for a stop codon positioned within the transmembrane domain or the cytoplasmic domain, or positioned between the extracellular domain and the transmembrane domain or cytoplasmic domain. For example, an isolated polynucleotide coding for a GDF Trap may comprise a full-length ActRIIB polynucleotide sequence such as SEQ ID NO: 4 having one or more variations, or a partially truncated version, said isolated polynucleotide further comprising a transcription termination codon at least six hundred nucleotides before the 3'-terminus or otherwise positioned such that translation of the polynucleotide gives rise to an extracellular domain optionally fused to a truncated portion of a full-length ActRIIB Nucleic acids disclosed herein may be operably linked to a promoter for expression, and the disclosure provides cells transformed with such recombinant polynucleotides. Preferably the cell is a mammalian cell such as a CHO cell.

In certain aspects, the disclosure provides methods for making a GDF Trap polypeptide. Such a method may include expressing any of the nucleic acids (e.g., SEQ ID NO: 5, 25, 27, 30 or 31) disclosed herein in a suitable cell, such as a Chinese hamster ovary (CHO) cell. Such a method may comprise: a) culturing a cell under conditions suitable for expression of the GDF Trap polypeptide, wherein said cell is transformed with a GDF Trap expression construct; and b) recovering the GDF Trap polypeptide so expressed. GDF Trap polypeptides may be recovered as crude, partially purified or highly purified fractions using any of the well known techniques for obtaining protein from cell cultures.

In certain aspects, a GDF Trap polypeptide disclosed herein may be used in a method for promoting red blood cell production or increasing red blood cell levels in a subject. In certain embodiments, the disclosure provides methods for treating a disorder associated with low red blood cell counts or low hemoglobin levels (e.g., an anemia, myelodysplastic syndrome, etc.), or to promote red blood cell production, in patients in need thereof. A method may comprise administering to a subject in need thereof an effective amount of a GDF Trap polypeptide. In certain aspects, the disclosure provides uses of GDF Trap polypeptides for making a medicament for the treatment of a disorder or condition as described herein.

In certain aspects, the disclosure provides methods for administering a GDF Trap polypeptide to a patient. In part, the disclosure demonstrates that GDF Trap polypeptides can be used to increase red blood cell and hemoglobin levels. GDF Trap polypeptides may also be used for treating or preventing other therapeutic uses such as promoting muscle growth. In certain instances, when administering a GDF Trap polypeptide for promoting muscle growth, it may be desirable to monitor the effects on red blood cells during administration of the GDF Trap polypeptide, or to determine or adjust the dosing of the GDF Trap polypeptide, in order to reduce undesired effects on red blood cells. For example, increases in red blood cell levels, hemoglobin levels, or hematocrit levels may cause increases in blood pressure.

BRIEF DESCRIPTION OF THE DRAWINGS

FIG. 1 shows an alignment of the extracellular domains of human ActRIIA (SEQ ID NO: 15) and human ActRIIB (SEQ ID NO: 2) with the residues that are deduced herein, based on composite analysis of multiple ActRIIB and ActRIIA crystal structures to directly contact ligand (the ligand binding pocket) indicated with boxes.

Figure 2:
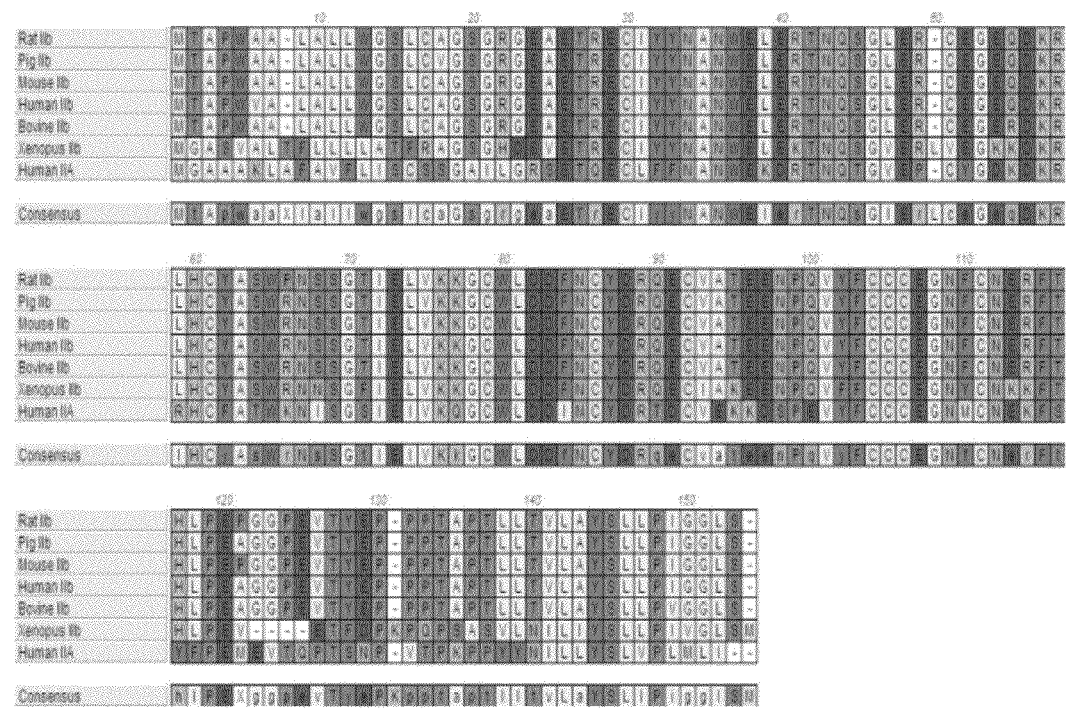

FIG. 2 shows a multiple sequence alignment of various vertebrate ActRIIB proteins and human ActRIIA (SEQ ID NOs: 16-23).

FIG. 3 shows the full amino acid sequence for the GDF Trap ActRIIB(L79D 20-134)-hFc (SEQ ID NO: 11), including the TPA leader sequence (double underlined), ActRIIB extracellular domain (residues 20-134 in SEQ ID NO: 1; underlined), and hFc domain. The aspartate substituted at position 79 in the native sequence is double underlined and highlighted, as is the glycine revealed by sequencing to be the N-terminal residue in the mature fusion protein.

FIG. 4 shows a nucleotide sequence encoding ActRIIB (L79D 20-134)-hFc. SEQ ID NO: 25 corresponds to the sense strand, and SEQ ID NO: 33 corresponds to the antisense strand. The TPA leader (nucleotides 1-66) is double underlined, and the ActRIIB extracellular domain (nucleotides 76-420) is underlined.

FIG. 5 shows the full amino acid sequence for the truncated GDF Trap ActRIIB(L79D 25-131)-hFc (SEQ ID NO: 26), including the TPA leader (double underlined), truncated ActRIIB extracellular domain (residues 25-131 in SEQ ID NO: 1; underlined), and hFc domain. The aspartate substituted at position 79 in the native sequence is double underlined and highlighted, as is the glutamate revealed by sequencing to be the N-terminal residue in the mature fusion protein.

FIG. 6 shows a nucleotide sequence encoding ActRIIB (L79D 25-131)-hFc. SEQ ID NO: 27 corresponds to the sense strand, and SEQ ID NO: 34 corresponds to the antisense strand. The TPA leader (nucleotides 1-66) is double underlined, and the truncated ActRIIB extracellular domain (nucleotides 76-396) is underlined. The amino acid sequence for the ActRIIB extracellular domain (residues 25-131 in SEQ ID NO: 1) is also shown.

FIG. 7 shows the amino acid sequence for the truncated GDF Trap ActRIIB(L79D 25-131)-hFc without a leader (SEQ ID NO: 28). The truncated ActRIIB extracellular domain (residues 25-131 in SEQ ID NO: 1) is underlined. The aspartate substituted at position 79 in the native sequence is double underlined and highlighted, as is the glutamate revealed by sequencing to be the N-terminal residue in the mature fusion protein.

FIG. 8 shows the amino acid sequence for the truncated GDF Trap ActRIIB(L79D 25-131) without the leader, hFc domain, and linker (SEQ ID NO: 29). The aspartate substituted at position 79 in the native sequence is underlined and highlighted, as is the glutamate revealed by sequencing to be the N-terminal residue in the mature fusion protein.

FIG. 9 shows an alternative nucleotide sequence encoding ActRIIB(L79D 25-131)-hFc. SEQ ID NO: 30 corresponds to the sense strand, and SEQ ID NO: 35 corresponds to the antisense strand. The TPA leader (nucleotides 1-66) is double underlined, the truncated ActRIIB extracellular domain (nucleotides 76-396) is underlined, and substitutions in the wildtype nucleotide sequence of the extracellular domain are double underlined and highlighted (compare with SEQ ID NO: 27, FIG. 6). The amino acid sequence for the ActRIIB extracellular domain (residues 25-131 in SEQ ID NO: 1) is also shown.

FIG. 10 shows nucleotides 76-396 (SEQ ID NO: 31) of the alternative nucleotide sequence shown in FIG. 9 (SEQ ID NO: 30). The same nucleotide substitutions indicated in FIG. 9 are also underlined and highlighted here. SEQ ID NO: 31 encodes only the truncated ActRIIB extracellular domain (corresponding to residues 25-131 in SEQ ID NO: 1) with a L79D substitution, e.g., ActRIIB(L79D 25-131).

Figure 20:
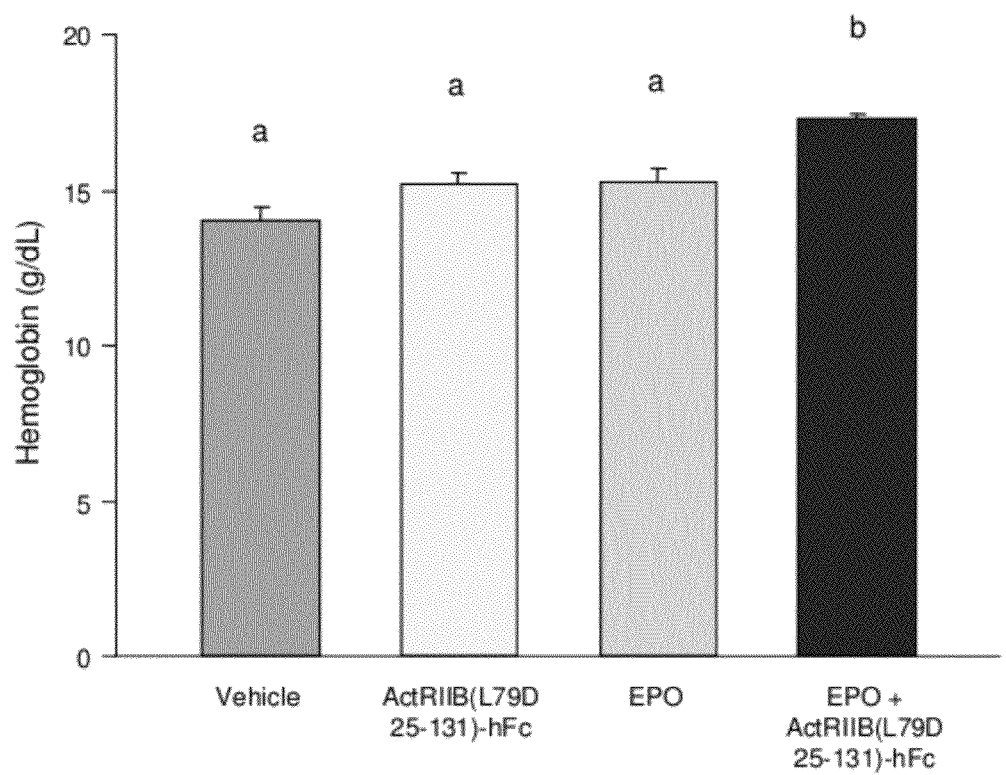

FIG. 20 shows the effect of combined treatment with EPO and ActRIIB(L79D 25-131)-hFc for 72 hours on hemoglobin concentrations in mice. Data are means±SEM (n=4 per group), and means that are significantly different from each other (p<0.05) are designated by different letters. Combined treatment increased hemoglobin concentrations by 23% compared to vehicle, which was also a synergistic effect.

Figure 21:
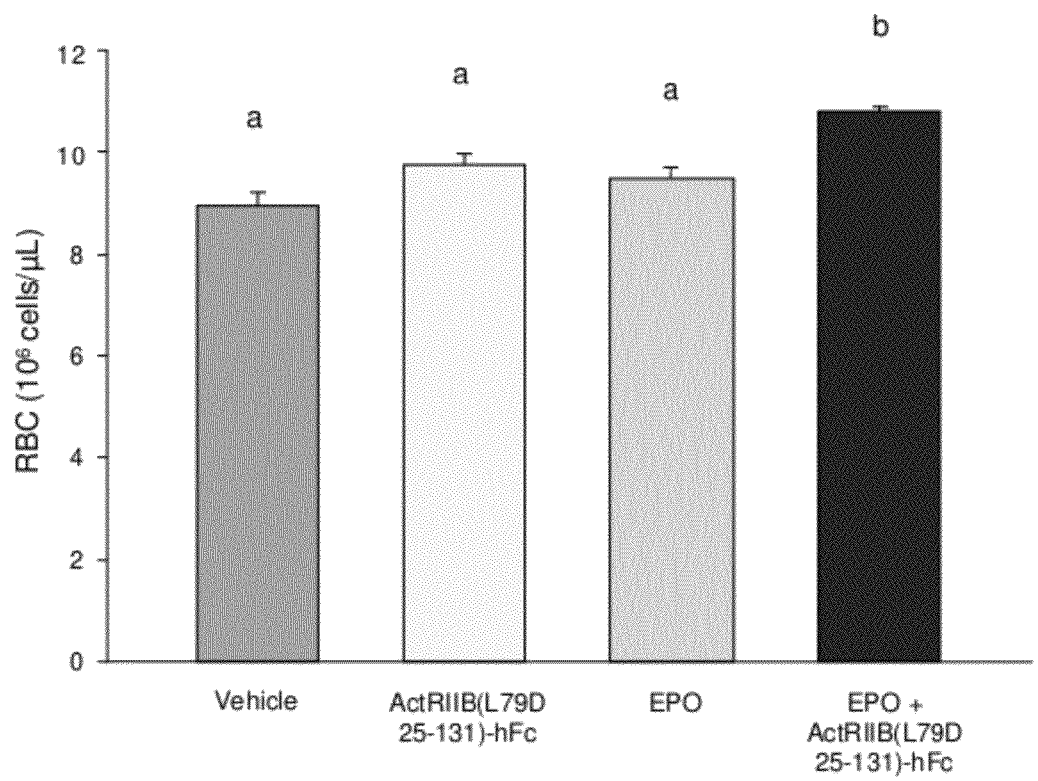

FIG. 21 shows the effect of combined treatment with EPO and ActRIIB(L79D 25-131)-hFc for 72 hours on red blood cell concentrations in mice. Data are means±SEM (n=4 per group), and means that are significantly different from each other (p<0.05) are designated by different letters. Combined treatment increased red blood cell concentrations by 20% compared to vehicle, which was also a synergistic effect.

Figure 22:
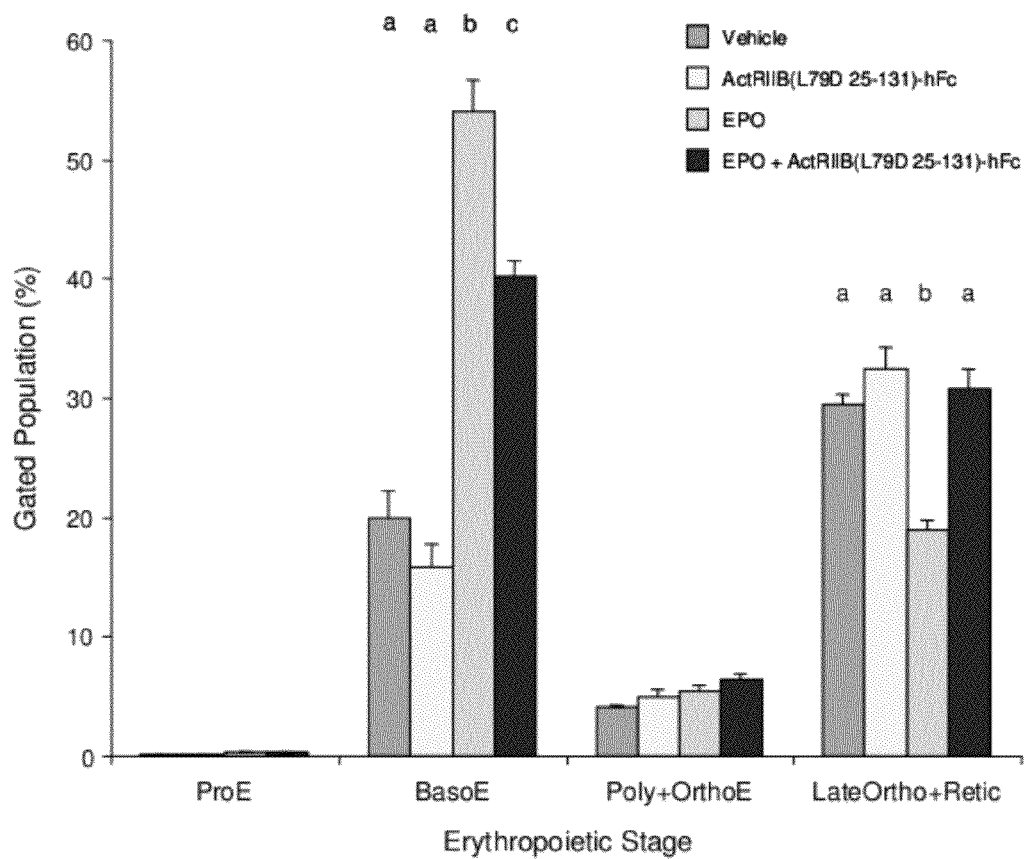

FIG. 22 shows the effect of combined treatment with EPO and ActRIIB(L79D 25-131)-hFc for 72 hours on numbers of erythropoietic precursor cells in mouse spleen. Data are means±SEM (n=4 per group), and means that are significantly different from each other (p<0.01) are designated by different letters. Whereas EPO alone increased the number of basophilic erythroblasts (BasoE) dramatically at the expense of late-stage precursor maturation, combined treatment increased BasoE numbers to a lesser but still significant extent while supporting undiminished maturation of late-stage precursors.

DETAILED DESCRIPTION OF THE INVENTION

1. Overview

EPO is a glycoprotein hormone involved in the growth and maturation of erythroid progenitor cells into erythrocytes. EPO is produced by the liver during fetal life and by the kidney in adults. Decreased production of EPO, which commonly occurs in adults as a consequence of renal failure, leads to anemia. EPO has been produced by genetic engineering techniques based on expression and secretion of the protein from a host cell transfected with the EPO gene. Administration of such recombinant EPO has been effective in the treatment of anemia. For example, Eschbach et al. (1987, N Engl J Med 316:73) describe the use of EPO to correct anemia caused by chronic renal failure.

Effects of EPO are mediated through its binding to, and activation of, a cell surface receptor belonging to the cytokine receptor superfamily and designated the EPO receptor. The human and murine EPO receptors have been cloned and expressed (D'Andrea et al., 1989, Cell 57:277; Jones et al., 1990, Blood 76:31; Winkelman et al., 1990, Blood 76:24; WO 90/08822/U.S. Pat. No. 5,278,065). The human EPO receptor gene encodes a 483 amino acid transmembrane protein comprising an extracellular domain of approximately 224 amino acids and exhibits approximately 82% amino acid sequence identity with the murine EPO receptor (See U.S. Pat. No. 6,319,499). The cloned, full-length EPO receptor expressed in mammalian cells (66-72 kDa) binds EPO with an affinity ($K_D$=100-300 nM) similar to that of the native receptor on erythroid progenitor cells. Thus, this form is thought to contain the main EPO binding determinant and is referred to as the EPO receptor. By analogy with other closely related cytokine receptors, the EPO receptor is thought to dimerize upon agonist binding. Nevertheless, the detailed structure of the EPO receptor, which may be a multimeric complex, and its specific mechanism of activation are not completely understood (U.S. Pat. No. 6,319,499).

Activation of the EPO receptor results in several biological effects. These include increased proliferation of immature erythroblasts, increased differentiation of immature erythroblasts, and decreased apoptosis in erythroid progenitor cells (Liboi et al., 1993, Proc Natl Acad Sci USA 90:11351-11355; Koury et al., 1990, Science 248:378-381). The EPO receptor signal transduction pathways mediating proliferation and differentiation appear to be distinct (Noguchi et al., 1988, Mol Cell Biol 8:2604; Patel et al., 1992, J Biol Chem 1992, 267:21300; Liboi et al., ibid). Some results suggest that an accessory protein may be required for mediation of the differentiation signal (Chiba et al., 1993, Nature 362:646; Chiba et al., 1993, Proc Natl Acad Sci USA 90:11593); however, there is controversy regarding the role of accessory proteins in differentiation since a constitutively activated form of the receptor can stimulate both proliferation and differentiation (Pharr et al., 1993, Proc Natl Acad Sci USA 90:938).

EPO receptor activators include small-molecule erythropoiesis-stimulating agents (ESAs) as well as EPO-based compounds. An example of the former is a dimeric peptide-based agonist covalently linked to polyethylene glycol (proprietary name Hematide), which has shown erythropoiesis-stimulating properties in healthy volunteers and in patients with both chronic kidney disease and endogenous anti-EPO antibodies (Stead et al., 2006, Blood 108:1830-1834; Macdougall et al., 2009, N Engl J Med 361:1848-1855). Other examples include nonpeptide-based ESAs (Qureshi et al., 1999, Proc Natl Acad Sci USA 96:12156-12161).

EPO receptor activators also include compounds that stimulate erythropoiesis indirectly, without contacting EPO receptor itself, by enhancing production of endogenous EPO. For example, hypoxia-inducible transcription factors (HIFs) are endogenous stimulators of EPO gene expression that are suppressed (destabilized) under normoxic conditions by cellular regulatory mechanisms. Therefore, inhibitors of HIF prolyl hydroxylase enzymes are being investigated for EPO-inducing activity in vivo. Other indirect activators of EPO receptor include inhibitors of GATA-2 transcription factor (Nakano et al., 2004, Blood 104:4300-4307), which typically inhibits EPO gene expression, and inhibitors of hemopoietic cell phosphatase (HCP or SHP-1), which functions as a negative regulator of EPO receptor signal transduction (Klingmuller et al., 1995, Cell 80:729-738).

The transforming growth factor-beta (TGF-beta) superfamily contains a variety of growth factors that share common sequence elements and structural motifs. These proteins are known to exert biological effects on a large variety of cell types in both vertebrates and invertebrates. Members of the superfamily perform important functions during embryonic development in pattern formation and tissue specification and can influence a variety of differentiation processes, including adipogenesis, myogenesis, chondrogenesis, cardiogenesis, hematopoiesis, neurogenesis, and epithelial cell differentiation. The family is divided into two general branches: the BMP/GDF and the TGF-beta/Activin/BMP10 branches, whose members have diverse, often complementary effects. By manipulating the activity of a member of the TGF-beta family, it is often possible to cause significant physiological changes in an organism. For example, the Piedmontese and Belgian Blue cattle breeds carry a loss-of-function mutation in the GDF8 (also called myostatin) gene that causes a marked increase in muscle mass. Grobet et al., Nat Genet. 1997, 17(1):71-4. Furthermore, in humans, inactive alleles of GDF8 are associated with increased muscle mass and, reportedly, exceptional strength. Schuelke et al., N Engl J Med 2004, 350:2682-8.

TGF-β signals are mediated by heteromeric complexes of type I and type II serine/threonine kinase receptors, which phosphorylate and activate downstream Smad proteins upon ligand stimulation (Massagué, 2000, Nat. Rev. Mol. Cell Biol. 1:169-178). These type I and type II receptors are transmembrane proteins, composed of a ligand-binding extracellular domain with cysteine-rich region, a transmembrane domain, and a cytoplasmic domain with predicted serine/threonine specificity. Type I receptors are essential for signaling. Type II receptors are required for binding ligands and for expression of Type I receptors. Type I and II activin receptors form a stable complex after ligand binding, resulting in phosphorylation of Type I receptors by Type II receptors.

Two related Type II receptors (ActRII), ActRIIA and ActRIIB, have been identified as the Type II receptors for activins (Mathews and Vale, 1991, Cell 65:973-982; Attisano et al., 1992, Cell 68: 97-108). Besides activins, ActRIIA and ActRIIB can biochemically interact with several other TGF-β family proteins, including BMP7, Nodal, GDF8, and GDF11 (Yamashita et al., 1995, J. Cell Biol. 130:217-226; Lee and McPherson, 2001, Proc. Natl. Acad. Sci. 98:9306-9311; Yeo and Whitman, 2001, Mol. Cell 7: 949-957; Oh et al., 2002, Genes Dev. 16:2749-54). ALK4 is the primary type I receptor for activins, particularly for activin A, and ALK-7 may serve as a receptor for activins as well, particularly for activin B. In certain embodiments, the present invention relates to antagonizing a ligand of ActRIIB receptors (also referred to as an ActRIIB ligand) with a subject GDF Trap polypeptide. Exemplary ligands of ActRIIB receptors include some TGF-β family members, such as activin, Nodal, GDF8, GDF11, and BMP7.

Activins are dimeric polypeptide growth factors that belong to the TGF-beta superfamily. There are three principal activin forms (A, B, and AB) that are homo/heterodimers of two closely related β subunits ($β_Aβ_A$, $β_Bβ_B$, and $β_Aβ_B$, respectively). The human genome also encodes an activin C and an activin E, which are primarily expressed in the liver, and heterodimeric forms containing $β_C$ or $β_E$ are also known. In the TGF-beta superfamily, activins are unique and multifunctional factors that can stimulate hormone production in ovarian and placental cells, support neuronal cell survival, influence cell-cycle progress positively or negatively depending on cell type, and induce mesodermal differentiation at least in amphibian embryos (DePaolo et al., 1991, Proc Soc Ep Biol Med. 198:500-512; Dyson et al., 1997, Curr Biol. 7:81-84; Woodruff, 1998, Biochem Pharmacol. 55:953-963). Moreover, erythroid differentiation factor (EDF) isolated from the stimulated human monocytic leukemic cells was found to be identical to activin A (Murata et al., 1988, PNAS, 85:2434). It has been suggested that activin A promotes erythropoiesis in the bone marrow. In several tissues, activin signaling is antagonized by its related heterodimer, inhibin. For example, during the release of follicle-stimulating hormone (FSH) from the pituitary, activin promotes FSH secretion and synthesis, while inhibin prevents FSH secretion and synthesis. Other proteins that may regulate activin bioactivity and/or bind to activin include follistatin (FS), follistatin-related protein (FSRP) and $α_2$-macroglobulin.

Nodal proteins have functions in mesoderm and endoderm induction and formation, as well as subsequent organization of axial structures such as heart and stomach in early embryogenesis. It has been demonstrated that dorsal tissue in a developing vertebrate embryo contributes predominantly to the axial structures of the notochord and pre-chordal plate while it recruits surrounding cells to form non-axial embryonic structures. Nodal appears to signal through both type I and type II receptors and intracellular effectors known as Smad proteins. Recent studies support the idea that ActRIIA and ActRIIB serve as type II receptors for Nodal (Sakuma et al., Genes Cells. 2002, 7:401-12). It is suggested that Nodal ligands interact with their co-factors (e.g., cripto) to activate activin type I and type II receptors, which phosphorylate Smad2. Nodal proteins are implicated in many events critical to the early vertebrate embryo, including mesoderm formation, anterior patterning, and left-right axis specification. Experimental evidence has demonstrated that Nodal signaling activates pAR3-Lux, a luciferase reporter previously shown to respond specifically to activin and TGF-beta. However, Nodal is unable to induce pTlx2-Lux, a reporter specifically responsive to bone morphogenetic proteins. Recent results provide direct biochemical evidence that Nodal signaling is mediated by both activin-TGF-beta pathway Smads, Smad2 and Smad3. Further evidence has shown that the extracellular cripto protein is required for Nodal signaling, making it distinct from activin or TGF-beta signaling.

Growth and Differentiation Factor-8 (GDF8) is also known as myostatin. GDF8 is a negative regulator of skeletal muscle mass. GDF8 is highly expressed in the developing and adult skeletal muscle. The GDF8 null mutation in transgenic mice is characterized by a marked hypertrophy and hyperplasia of the skeletal muscle (McPherron et al., Nature, 1997, 387:83-90). Similar increases in skeletal muscle mass are evident in naturally occurring mutations of GDF8 in cattle (Ashmore et al., 1974, Growth, 38:501-507; Swatland and Kieffer, J. Anim. Sci., 1994, 38:752-757; McPherron and Lee, Proc. Natl. Acad. Sci. USA, 1997, 94:12457-12461; and Kambadur et al., Genome Res., 1997, 7:910-915) and, strikingly, in humans (Schuelke et al., N Engl J Med 2004; 350:2682-8). Studies have also shown that muscle wasting associated with HIV-infection in humans is accompanied by increases in GDF8 protein expression (Gonzalez-Cadavid et al., PNAS, 1998, 95:14938-43). In addition, GDF8 can modulate the production of muscle-specific enzymes (e.g., creatine kinase) and modulate myoblast cell proliferation (WO 00/43781). The GDF8 propeptide can noncovalently bind to the mature GDF8 domain dimer, inactivating its biological activity (Miyazono et al. (1988) J. Biol. Chem., 263: 6407-6415; Wakefield et al. (1988) J. Biol. Chem., 263; 7646-7654; and Brown et al. (1990) Growth Factors, 3: 35-43). Other proteins which bind to GDF8 or structurally related proteins and inhibit their biological activity include follistatin, and potentially, follistatin-related proteins (Gamer et al. (1999) Dev. Biol., 208: 222-232).

Growth and Differentiation Factor-11 (GDF11), also known as BMP11, is a secreted protein (McPherron et al., 1999, Nat. Genet. 22: 260-264). GDF11 is expressed in the tail bud, limb bud, maxillary and mandibular arches, and dorsal root ganglia during mouse development (Nakashima et al., 1999, Mech. Dev. 80: 185-189). GDF11 plays a unique role in patterning both mesodermal and neural tissues (Gamer et al., 1999, Dev Biol., 208:222-32). GDF11 was shown to be a negative regulator of chondrogenesis and myogenesis in developing chick limb (Gamer et al., 2001, Dev Biol. 229: 407-20). The expression of GDF11 in muscle also suggests its role in regulating muscle growth in a similar way to GDF8. In addition, the expression of GDF11 in brain suggests that GDF11 may also possess activities that relate to the function of the nervous system. Interestingly, GDF11 was found to inhibit neurogenesis in the olfactory epithelium (Wu et al., 2003, Neuron. 37:197-207). Hence, GDF11 may have in vitro and in vivo applications in the treatment of diseases such as muscle diseases and neurodegenerative diseases (e.g., amyotrophic lateral sclerosis).

Bone morphogenetic protein (BMP7), also called osteogenic protein-1 (OP-1), is well known to induce cartilage and bone formation. In addition, BMP7 regulates a wide array of physiological processes. For example, BMP7 may be the osteoinductive factor responsible for the phenomenon of epithelial osteogenesis. It is also found that BMP7 plays a role in calcium regulation and bone homeostasis Like activin, BMP7 binds to Type II receptors, ActRIIA and ActRIIB However, BMP7 and activin recruit distinct Type I receptors into heteromeric receptor complexes. The major BMP7 Type I receptor observed was ALK2, while activin bound exclusively to ALK4 (ActRIIB) BMP7 and activin elicited distinct biological responses and activated different Smad pathways (Macias-Silva et al., 1998, J Biol Chem. 273:25628-36).

As demonstrated herein, a GDF Trap polypeptide, which is a variant ActRIIB polypeptide (ActRIIB), is more effective at increasing red blood cell levels in vivo as compared to a wild-type soluble ActRIIB polypeptide and has beneficial effects in a variety of models for anemias. Additionally, it is shown that the use of a GDF Trap polypeptide in combination with an EPO receptor activator causes a substantial increase in red blood cell formation. It should be noted that hematopoiesis is a complex process, regulated by a variety of factors, including erythropoietin, G-CSF and iron homeostasis. The terms "increase red blood cell levels" and "promote red blood cell formation" refer to clinically observable metrics, such as hematocrit, red blood cell counts and hemoglobin measurements, and are intended to be neutral as to the mechanism by which such changes occur.

In addition to stimulating red blood cell levels, GDF Trap polypeptides are useful for a variety of therapeutic applications, including, for example, promoting muscle growth (see PCT Publication Nos. WO 2006/012627 and WO 2008/097541, which are hereby incorporated by reference in their entirety). In certain instances, when administering a GDF Trap polypeptide for the purpose of increasing muscle, it may be desirable to reduce or minimize effects on red blood cells. By monitoring various hematologic parameters in patients being treated with, or who are candidates for treatment with, a GDF Trap polypeptide, appropriate dosing (including amounts and frequency of administration) may be determined based on an individual patient's needs, baseline hematologic parameters, and purpose for treatment. Furthermore, therapeutic progress and effects on one or more hematologic parameters over time may be useful in managing patients being dosed with a GDF Trap polypeptide by facilitating patient care, determining appropriate maintenance dosing (both amounts and frequency), etc.

The terms used in this specification generally have their ordinary meanings in the art, within the context of this invention and in the specific context where each term is used. Certain terms are discussed below or elsewhere in the specification, to provide additional guidance to the practitioner in describing the compositions and methods of the invention and how to make and use them. The scope or meaning of any use of a term will be apparent from the specific context in which the term is used.

"About" and "approximately" shall generally mean an acceptable degree of error for the quantity measured given the nature or precision of the measurements. Typically, exemplary degrees of error are within 20 percent (%), preferably within 10%, and more preferably within 5% of a given value or range of values.

Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

The methods of the invention may include steps of comparing sequences to each other, including wild-type sequence to one or more mutants (sequence variants). Such comparisons typically comprise alignments of polymer sequences, e.g., using sequence alignment programs and/or algorithms that are well known in the art (for example, BLAST, FASTA and MEGALIGN, to name a few). The skilled artisan can readily appreciate that, in such alignments, where a mutation contains a residue insertion or deletion, the sequence alignment will introduce a "gap" (typically represented by a dash, or "Λ") in the polymer sequence not containing the inserted or deleted residue.

"Homologous," in all its grammatical forms and spelling variations, refers to the relationship between two proteins that possess a "common evolutionary origin," including proteins from superfamilies in the same species of organism, as well as homologous proteins from different species of organism. Such proteins (and their encoding nucleic acids) have sequence homology, as reflected by their sequence similarity, whether in terms of percent identity or by the presence of specific residues or motifs and conserved positions.

The term "sequence similarity," in all its grammatical forms, refers to the degree of identity or correspondence between nucleic acid or amino acid sequences that may or may not share a common evolutionary origin.

However, in common usage and in the instant application, the term "homologous," when modified with an adverb such as "highly," may refer to sequence similarity and may or may not relate to a common evolutionary origin.

2. GDF Trap Polypeptides

In certain aspects, the invention relates to GDF Trap polypeptides, e.g., soluble variant ActRIIB polypeptides, including, for example, fragments, functional variants, and modified forms of ActRIIB polypeptides. In certain embodiments, the GDF Trap polypeptides have at least one similar or same biological activity as a corresponding wild-type ActRIIB polypeptide. For example, a GDF Trap polypeptide of the invention may bind to and inhibit the function of an ActRIIB ligand (e.g., activin A, activin AB, activin B, Nodal, GDF8, GDF11 or BMP7). Optionally, a GDF Trap polypeptide increases red blood cell levels. Examples of GDF Trap polypeptides include human ActRIIB precursor polypeptides (SEQ ID NO: 1 or 39) having one or more sequence variations, and soluble human ActRIIB polypeptides (e.g., SEQ ID NOs: 2, 3, 7, 11, 26, 28, 29, 32, 37, 38, 40 and 41) having one or more sequence variations. A GDF Trap refers to an ActRIIB polypeptide having a decreased affinity for activin relative to other ActRIIB ligands, including for example GDF11 and/or myostatin.

As used herein, the term "ActRIIB" refers to a family of activin receptor type IIb (ActRIIB) proteins from any species and variants derived from such ActRIIB proteins by mutagenesis or other modification. Reference to ActRIIB herein is understood to be a reference to any one of the currently identified forms. Members of the ActRIIB family are generally transmembrane proteins, composed of a ligand-binding extracellular domain with a cysteine-rich region, a transmembrane domain, and a cytoplasmic domain with predicted serine/threonine kinase activity. Amino acid sequences of human ActRIIA soluble extracellular domain (provided for comparison) and ActRIIB soluble extracellular domain are illustrated in FIG. 1.

The term "ActRIIB polypeptide" includes polypeptides comprising any naturally occurring polypeptide of an ActRIIB family member as well as any variants thereof (including mutants, fragments, fusions, and peptidomimetic forms) that retain a useful activity. See, for example, WO 2006/012627. For example, ActRIIB polypeptides include polypeptides derived from the sequence of any known ActRIIB having a sequence at least about 80% identical to the sequence of an ActRIIB polypeptide, and optionally at least 85%, 90%, 95%, 97%, 99% or greater identity. For example, an ActRIIB polypeptide may bind to and inhibit the function of an ActRIIB protein and/or activin. An ActRIIB polypeptide which is a GDF Trap may be selected for activity in promoting red blood cell formation in vivo. Examples of ActRIIB polypeptides include human ActRIIB precursor polypeptide (SEQ ID NO: 1 and 39) and soluble human ActRIIB polypeptides (e.g., SEQ ID NO: 2, 3, 7, 11, 26, 28, 29, 32, 37, 38, 40 and 41). Numbering of amino acids for all ActRIIB-related polypeptides described herein is based on the numbering for SEQ ID NO:1, unless specifically designated otherwise.

The human ActRIIB precursor protein sequence is as follows:

```
                                              (SEQ ID NO: 1)
MTAPWVALALLWGSLWPGSGRGEAETRECIYYNANWELERTNQSGLE

RCEGEQDKRLHCYASWRNSSGTIELVKKGCWLDDFNCYDRQECVATE

ENPQVYFCCCEGNFCNERFTHLPEAGGPEVTYEPPPTAPTLLTVLAY

SLLPIGGLSLIVLLAFWMYRHRKPPYGHVDIHEDPGPPPPSPLVGLK

PLQLLEIKARGRFGCVWKAQLMNDFVAVKIFPLQDKQSWQSEREIFS

TPGMKHENLLQFIAAEKRGSNLEVELWLITAFHDKGSLTDYLKGNII

TWNELCHVAETMSRGLSYLHEDVPWCRGEGHKPSIAHRDFKSKNVLL

KSDLTAVLADFGLAVRFEPGKPPGDTHGQVGTRRYMAPEVLEGAINF

QRDAFLRIDMYAMGLVLWELVSRCKAADGPVDEYMLPFEEEIGQHPS

LEELQEVVVHKKMRPTIKDHWLKHPGLAQLCVTIEECWDHDAEARLS

AGCVEERVSLIRRSVNGTTSDCLVSLVTSVTNVDLPPKESSI
```

The signal peptide is single underlined; the extracellular domain is in bold and the potential N-linked glycosylation sites are in boxes.

A form with an alanine at position 64 is also reported in the literature, as follows:

```
                                             (SEQ ID NO: 39)
MTAPWVALALLWGSLWPGSGRGEAETRECIYYNANWELERTNQSGL

ERCEGEQDKRLHCYASWANSSGTIELVKKGCWLDDFNCYDRQECVA

TEENPQVYFCCCEGNFCNERFTHLPEAGGPEVTYEPPPTAPTLLTV

LAYSLLPIGGLSLIVLLAFWMYRHRKPPYGHVDIHEDPGPPPPSPL

VGLKPLQLLEIKARGRFGCVWKAQLMNDFVAVKIFPLQDKQSWQSE

REIFSTPGMKHENLLQFIAAEKRGSNLEVELWLITAFHDKGSLTDY

LKGNIITWNELCHVAETMSRGLSYLHEDVPWCRGEGHKPSIAHRDF
```

-continued
```
KSKNVLLKSDLTAVLADFGLAVRFEPGKPPGDTHGQVGTRRYMAPE

VLEGAINFQRDAFLRIDMYAMGLVLWELVSRCKAADGPVDEYMLPF

EEEIGQHPSLEELQEVVVHKKMRPTIKDHWLKHPGLAQLCVTIEEC

WDHDAEARLSAGCVEERVSLIRRSVNGTTSDCLVSLVTSVTNVDLP

PKESSI
```

The human ActRIIB soluble (extracellular), processed polypeptide sequence is as follows:

```
                                              (SEQ ID NO: 2)
GRGEAETRECIYYNANWELERTNQSGLERCEGEQDKRLHCYASWRN

SSGTIELVKKGCWLDDFNCYDRQECVATEENPQVYFCCCEGNFCNE

RFTHLPEAGGPEVTYEPPPTAPT
```

The alternative form with an A64 is as follows:

```
                                             (SEQ ID NO: 40)
GRGEAETRECIYYNANWELERTNQSGLERCEGEQDKRLHCYASWANS

SGTIELVKKGCWLDDFNCYDRQECVATEENPQVYFCCCEGNFCNERF

THLPEAGGPEVTYEPPPTAPT
```

In some conditions, the protein may be produced with an "SGR . . ." sequence at the N-terminus. The C-terminal "tail" of the extracellular domain is underlined. The sequence with the "tail" deleted (a Δ15 sequence) is as follows:

```
                                              (SEQ ID NO: 3)
GRGEAETRECIYYNANWELERTNQSGLERCEGEQDKRLHCYASWRNS

SGTIELVKKGCWLDDFNCYDRQECVATEENPQVYFCCCEGNFCNERF

THLPEA
```

The alternative form with an A64 is as follows:

```
                                             (SEQ ID NO: 41)
GRGEAETRECIYYNANWELERTNQSGLERCEGEQDKRLHCYASWANS

SGTIELVKKGCWLDDFNCYDRQECVATEENPQVYFCCCEGNFCNERF

THLPEA
```

In some conditions, the protein may be produced with an "SGR . . ." sequence at the N-terminus. The nucleic acid sequence encoding a human ActRIIB precursor protein is as follows: (nucleotides 5-1543 of Genbank entry NM_001106) (the sequence as shown provides an alanine at position 64, and may be modified to provide an arginine instead)

```
                                              (SEQ ID NO: 4)
ATGACGGCGCCCTGGGTGGCCCTCGCCCTCCTCTGGGGATCGCTGTG

GCCCGGCTCTGGGCGTGGGGAGGCTGAGACACGGGAGTGCATCTACT

ACAACGCCAACTGGGAGCTGGAGCGCACCAACCAGAGCGGCCTGGAG

CGCTGCGAAGGCGAGCAGGACAAGCGGCTGCACTGCTACGCCTCCTG

GGCCAACAGCTCTGGCACCATCGAGCTCGTGAAGAAGGGCTGCTGGC

TAGATGACTTCAACTGCTACGATAGGCAGGAGTGTGTGGCCACTGAG
```

-continued
```
GAGAACCCCCAGGTGTACTTCTGCTGCTGTGAAGGCAACTTCTGCAA

CGAGCGCTTCACTCATTTGCCAGAGGCTGGGGGCCCGGAAGTCACGT

ACGAGCCACCCCCGACAGCCCCCACCCTGCTCACGGTGCTGGCCTAC

TCACTGCTGCCCATCGGGGGCCTTTCCCTCATCGTCCTGCTGGCCTT

TTGGATGTACCGGCATCGCAAGCCCCCTACGGTCATGTGGACATCC

ATGAGGACCCTGGGCCTCCACCACCATCCCCTCTGGTGGGCCTGAAG

CCACTGCAGCTGCTGGAGATCAAGGCTCGGGGCGCTTTGGCTGTGT

CTGGAAGGCCCAGCTCATGAATGACTTTGTAGCTGTCAAGATCTTCC

CACTCCAGGACAAGCAGTCGTGGCAGAGTGAACGGGAGATCTTCAGC

ACACCTGGCATGAAGCACGAGAACCTGCTACAGTTCATTGCTGCCGA

GAAGCGAGGCTCCAACCTCGAAGTAGAGCTGTGGCTCATCACGGCCT

TCCATGACAAGGGCTCCCTCACGGATTACCTCAAGGGGAACATCATC

ACATGGAACGAACTGTGTCATGTAGCAGAGACGATGTCACGAGGCCT

CTCATACCTGCATGAGGATGTGCCCTGGTGCCGTGGCGAGGGCCACA

AGCCGTCTATTGCCCACAGGGACTTTAAAAGTAAGAATGTATTGCTG

AAGAGCGACCTCACAGCCGTGCTGGCTGACTTTGGCTTGGCTGTTCG

ATTTGAGCCAGGGAAACCTCCAGGGGACACCCACGGACAGGTAGGCA

CGAGACGGTACATGGCTCCTGAGGTGCTCGAGGGAGCCATCAACTTC

CAGAGAGATGCCTTCCTGCGCATTGACATGTATGCCATGGGGTTGGT

GCTGTGGGAGCTTGTGTCTCGCTGCAAGGCTGCAGACGGACCCGTGG

ATGAGTACATGCTGCCCTTTGAGGAAGAGATTGGCCAGCACCCTTCG

TTGGAGGAGCTGCAGGAGGTGGTGGTGCACAAGAAGATGAGGCCCAC

CATTAAAGATCACTGGTTGAAACACCCGGGCCTGGCCCAGCTTTGTG

TGACCATCGAGGAGTGCTGGGACCATGATGCAGAGGCTCGCTTGTCC

GCGGGCTGTGTGGAGGAGCGGGTGTCCCTGATTCGGAGGTCGGTCAA

CGGCACTACCTCGGACTGTCTCGTTTCCCTGGTGACCTCTGTCACCA

ATGTGGACCTGCCCCCTAAAGAGTCAAGCATCTAA
```

The nucleic acid sequence encoding a human ActRIIB soluble (extracellular) polypeptide is as follows (the sequence as shown provides an alanine at position 64, and may be modified to provide an arginine instead):

(SEQ ID NO: 5)
```
GGGCGTGGGGAGGCTGAGACACGGGAGTGCATCTACTACAACGCCAA

CTGGGAGCTGGAGCGCACCAACCAGAGCGGCCTGGAGCGCTGCGAAG

GCGAGCAGGACAAGCGGCTGCACTGCTACGCCTCCTGGGCCAACAGC

TCTGGCACCATCGAGCTCGTGAAGAAGGGCTGCTGGCTAGATGACTT

CAACTGCTACGATAGGCAGGAGTGTGTGGCCACTGAGGAGAACCCCC

AGGTGTACTTCTGCTGCTGTGAAGGCAACTTCTGCAACGAGCGCTTC

ACTCATTTGCCAGAGGCTGGGGGCCCGGAAGTCACGTACGAGCCACC

CCCGACAGCCCCCACC
```

In a specific embodiment, the invention relates to GDF Trap polypeptides which are variant forms of soluble ActRIIB polypeptides. As described herein, the term "soluble ActRIIB polypeptide" generally refers to polypeptides comprising an extracellular domain of an ActRIIB protein. The term "soluble ActRIIB polypeptide," as used herein, includes any naturally occurring extracellular domain of an ActRIIB protein as well as any variants thereof (including mutants, fragments and peptidomimetic forms) that retain a useful activity. For example, the extracellular domain of an ActRIIB protein binds to a ligand and is generally soluble. Examples of soluble ActRIIB polypeptides include ActRIIB soluble polypeptides (e.g., SEQ ID NOs: 2, 3, 7, 11, 26, 28, 29, 32, 37, 38, 40 and 41). Other examples of soluble ActRIIB polypeptides comprise a signal sequence in addition to the extracellular domain of an ActRIIB protein, see Example 1. The signal sequence can be a native signal sequence of an ActRIIB, or a signal sequence from another protein, such as a tissue plasminogen activator (TPA) signal sequence or a honey bee melittin (HBM) signal sequence.

The disclosure identifies functionally active portions and variants of ActRIIB Applicants have ascertained that an Fc fusion protein having the sequence disclosed by Hilden et al. (Blood. 1994 Apr. 15; 83(8):2163-70), which has an Alanine at the position corresponding to amino acid 64 of SEQ ID NO: 1 (A64), has a relatively low affinity for activin and GDF-11. By contrast, the same Fc fusion protein with an Arginine at position 64 (R64) has an affinity for activin and GDF-11 in the low nanomolar to high picomolar range. Therefore, a sequence with an R64 is used as the wild-type reference sequence for human ActRIIB in this disclosure.

Attisano et al. (Cell. 1992 Jan. 10; 68(1):97-108) showed that a deletion of the proline knot at the C-terminus of the extracellular domain of ActRIIB reduced the affinity of the receptor for activin. An ActRIIB-Fc fusion protein containing amino acids 20-119 of SEQ ID NO: 1, "ActRIIB(20-119)-Fc", has reduced binding to GDF-11 and activin relative to an ActRIIB(20-134)-Fc, which includes the proline knot region and the complete juxtamembrane domain. However, an ActRIIB(20-129)-Fc protein retains similar but somewhat reduced activity relative to the wild type, even though the proline knot region is disrupted. Thus, ActRIIB extracellular domains that stop at amino acid 134, 133, 132, 131, 130 and 129 are all expected to be active, but constructs stopping at 134 or 133 may be most active. Similarly, mutations at any of residues 129-134 are not expected to alter ligand binding affinity by large margins. In support of this, mutations of P129 and P130 do not substantially decrease ligand binding. Therefore, a GDF Trap polypeptide which is an ActRIIB-Fc fusion protein may end as early as amino acid 109 (the final cysteine), however, forms ending at or between 109 and 119 are expected to have reduced ligand binding. Amino acid 119 is poorly conserved and so is readily altered or truncated. Forms ending at 128 or later retain ligand binding activity. Forms ending at or between 119 and 127 will have an intermediate binding ability. Any of these forms may be desirable to use, depending on the clinical or experimental setting.

At the N-terminus of ActRIIB, it is expected that a protein beginning at amino acid 29 or before will retain ligand binding activity. Amino acid 29 represents the initial cysteine. An alanine to asparagine mutation at position 24 introduces an N-linked glycosylation sequence without substantially affecting ligand binding. This confirms that mutations in the region between the signal cleavage peptide and the cysteine cross-linked region, corresponding to amino acids 20-29 are well tolerated. In particular, constructs beginning at position 20, 21, 22, 23 and 24 will retain activity, and constructs beginning at positions 25, 26, 27, 28 and 29 are also expected to retain activity. Data shown in the Examples demonstrates that, surprisingly, a construct beginning at 22, 23, 24 or 25 will have the most activity.

Taken together, an active portion of ActRIIB comprises amino acids 29-109 of SEQ ID NO: 1, and GDF Trap constructs may, for example, comprise a portion of ActRIIB beginning at a residue corresponding to amino acids 20-29 of SEQ ID NO: 1 or 39 and ending at a position corresponding to amino acids 109-134 of SEQ ID NO: 1 or 39. Other examples include constructs that begin at a position from 20-29 or 21-29 and end at a position from 119-134, 119-133, 129-134, or 129-133 of SEQ ID NO: 1 or 39. Other examples include constructs that begin at a position from 20-24 (or 21-24, or 22-25) and end at a position from 109-134 (or 109-133), 119-134 (or 119-133) or 129-134 (or 129-133) of SEQ ID NO: 1 or 39. Variants within these ranges are also contemplated, particularly those having at least 80%, 85%, 90%, 95% or 99% identity to the corresponding portion of SEQ ID NO: 1 or 39. In certain embodiments, the GDF Trap polypeptide comprises, consists essentially of, or consists of, a polypeptide having an amino acid sequence that is at least 80%, 85%, 90%, 95%, 96%, 97%, 98%, 99% or 100% identical to amino acid residues 25-131 of SEQ ID NO: 1 or 39. In certain embodiments, the GDF Trap polypeptide comprises, consists essentially of, or consists of, a polypeptide having an amino acid sequence that is at least 80%, 85%, 90%, 95%, 96%, 97%, 98%, 99% or 100% identical to SEQ ID NOs: 7, 26, 28, 29, 32, 37 or 38. In preferred embodiments, the GDF Trap polypeptide consists of, or consists essentially of, the amino acid sequence of SEQ ID NO: 7, 26, 28, 29, 32, 37 or 38.

The disclosure includes the results of an analysis of composite ActRIIB structures, shown in FIG. 1, demonstrating that the ligand binding pocket is defined by residues Y31, N33, N35, L38 through T41, E47, E50, Q53 through K55, L57, H58, Y60, S62, K74, W78 through N83, Y85, R87, A92, and E94 through F101. At these positions, it is expected that conservative mutations will be tolerated, although a K74A mutation is well-tolerated, as are R40A, K55A, F82A and mutations at position L79. R40 is a K in *Xenopus*, indicating that basic amino acids at this position will be tolerated. Q53 is R in bovine ActRIIB and K in *Xenopus* ActRIIB, and therefore amino acids including R, K, Q, N and H will be tolerated at this position. Thus, a general formula for a GDF Trap protein is one that comprises amino acids 29-109 of SEQ ID NO: 1 or 39, but optionally beginning at a position ranging from 20-24 or 22-25 and ending at a position ranging from 129-134, and comprising no more than 1, 2, 5, 10 or 15 conservative amino acid changes in the ligand binding pocket, and zero, one or more non-conservative alterations at positions 40, 53, 55, 74, 79 and/or 82 in the ligand binding pocket. Such a protein may retain greater than 80%, 90%, 95% or 99% sequence identity to the sequence of amino acids 29-109 of SEQ ID NO: 1 or 39. Sites outside the binding pocket, at which variability may be particularly well tolerated, include the amino and carboxy termini of the extracellular domain (as noted above), and positions 42-46 and 65-73. An asparagine to alanine alteration at position 65 (N65A) actually improves ligand binding in the A64 background, and is thus expected to have no detrimental effect on ligand binding in the R64 background. This change probably eliminates glycosylation at N65 in the A64 background, thus demonstrating that a significant change in this region is likely to be tolerated. While an R64A change is poorly tolerated, R64K is well-tolerated, and thus another basic residue, such as H may be tolerated at position 64.

ActRIIB is well-conserved across nearly all vertebrates, with large stretches of the extracellular domain conserved completely. Many of the ligands that bind to ActRIIB are also highly conserved. Accordingly, comparisons of ActRIIB sequences from various vertebrate organisms provide insights into residues that may be altered. Therefore, an active, human ActRIIB variant polypeptide useful as a GDF Trap may include one or more amino acids at corresponding positions from the sequence of another vertebrate ActRIIB, or may include a residue that is similar to that in the human or other vertebrate sequence. The following examples illustrate this approach to defining an active ActRIIB variant. L46 is a valine in *Xenopus* ActRIIB, and so this position may be altered, and optionally may be altered to another hydrophobic residue, such as V, I or F, or a non-polar residue such as A. E52 is a K in *Xenopus*, indicating that this site may be tolerant of a wide variety of changes, including polar residues, such as E, D, K, R, H, S, T, P, G, Y and probably A. T93 is a K in *Xenopus*, indicating that a wide structural variation is tolerated at this position, with polar residues favored, such as S, K, R, E, D, H, G, P, G and Y. F108 is a Y in *Xenopus*, and therefore Y or other hydrophobic group, such as I, V or L should be tolerated. E111 is K in *Xenopus*, indicating that charged residues will be tolerated at this position, including D, R, K and H, as well as Q and N. R112 is K in *Xenopus*, indicating that basic residues are tolerated at this position, including R and H. A at position 119 is relatively poorly conserved, and appears as P in rodents and V in *Xenopus*, thus essentially any amino acid should be tolerated at this position.

The disclosure demonstrates that the addition of a further N-linked glycosylation site (N-X-S/T) increases the serum half-life of an ActRIIB-Fc fusion protein, relative to the ActRIIB(R64)-Fc form. By introducing an asparagine at position 24 (A24N construct), an NXT sequence is created that confers a longer half-life. Other NX(T/S) sequences are found at 42-44 (NQS) and 65-67 (NSS), although the latter may not be efficiently glycosylated with the R at position 64. N-X-S/T sequences may be generally introduced at positions outside the ligand binding pocket defined in FIG. 1. Particularly suitable sites for the introduction of non-endogenous N-X-S/T sequences include amino acids 20-29, 20-24, 22-25, 109-134, 120-134 or 129-134. N-X-S/T sequences may also be introduced into the linker between the ActRIIB sequence and the Fc or other fusion component. Such a site may be introduced with minimal effort by introducing an N in the correct position with respect to a pre-existing S or T, or by introducing an S or T at a position corresponding to a pre-existing N. Thus, desirable alterations that would create an N-linked glycosylation site are: A24N, R64N, S67N (possibly combined with an N65A alteration), E106N, R112N, G120N, E123N, P129N, A132N, R112S and R112T. Any S that is predicted to be glycosylated may be altered to a T without creating an immunogenic site, because of the protection afforded by the glycosylation Likewise, any T that is predicted to be glycosylated may be altered to an S. Thus the alterations S67T and S44T are contemplated. Likewise, in an A24N variant, an S26T alteration may be used. Accordingly, a GDF Trap may be an ActRIIB variant having one or more additional, non-endogenous N-linked glycosylation consensus sequences.

Position L79 of ActRIIB may be altered to confer altered activin—myostatin (GDF-11) binding properties. L79A or L79P reduces GDF-11 binding to a greater extent than activin binding. L79E or L79D retains GDF-11 binding. Remarkably, the L79E and L79D variants have greatly reduced activin binding. In vivo experiments indicate that these non-activin receptors retain significant ability to increase red blood cells but show decreased effects on other tissues. These data demonstrate the desirability and feasibility for obtaining polypeptides with reduced effects on activin. In exemplary embodiments, the methods described herein utilize a GDF Trap polypeptide which is a variant ActRIIB polypeptide comprising an acidic amino acid (e.g., D or E) at the position corresponding to position 79 of SEQ ID NO: 1 or 39, optionally in combination with one or more additional amino acid substitutions, additions, or deletions.

The variations described may be combined in various ways. Additionally, the results of the mutagenesis program described herein indicate that there are amino acid positions in ActRIIB that are often beneficial to conserve. These include position 64 (basic amino acid), position 80 (acidic or hydrophobic amino acid), position 78 (hydrophobic, and particularly tryptophan), position 37 (acidic, and particularly aspartic or glutamic acid), position 56 (basic amino acid), position 60 (hydrophobic amino acid, particularly phenylalanine or tyrosine). Thus, in each of the variants disclosed herein, the disclosure provides a framework of amino acids that may be conserved. Other positions that may be desirable to conserve are as follows: position 52 (acidic amino acid), position 55 (basic amino acid), position 81 (acidic), 98 (polar or charged, particularly E, D, R or K).

In certain embodiments, isolated fragments of ActRIIB polypeptides can be obtained by screening polypeptides recombinantly produced from the corresponding fragment of the nucleic acid encoding an ActRIIB polypeptide (e.g., SEQ ID NOs: 4 and 5). In addition, fragments can be chemically synthesized using techniques known in the art such as conventional Merrifield solid phase f-Moc or t-Boc chemistry. The fragments can be produced (recombinantly or by chemical synthesis) and tested to identify those peptidyl fragments that can function, for example, as antagonists (inhibitors) or agonists (activators) of an ActRIIB protein or an ActRIIB ligand.

In certain embodiments, GDF Trap polypeptide is a variant ActRIIB polypeptide having an amino acid sequence that is at least 75% identical to an amino acid sequence selected from SEQ ID NOs: 2, 3, 7, 11, 26, 28, 29, 32, 37, 38, 40 or 41. In certain cases, the GDF Trap has an amino acid sequence at least 80%, 85%, 90%, 95%, 97%, 98%, 99% or 100% identical to an amino acid sequence selected from SEQ ID NOs: 2, 3, 7, 11, 26, 28, 29, 32, 37, 38, 40 or 41. In certain embodiments, the GDF Trap comprises, consists essentially of, or consists of, an amino acid sequence at least 80%, 85%, 90%, 95%, 97%, 98%, 99% or 100% identical to an amino acid sequence selected from SEQ ID NOs: 2, 3, 7, 11, 26, 28, 29, 32, 37, 38, 40 or 41, wherein the position corresponding to L79 of SEQ ID NO: 1 is an acidic amino acid (e.g., a D or E amino acid residue).

In certain embodiments, the present invention contemplates making functional variants by modifying the structure of a GDF Trap polypeptide for such purposes as enhancing therapeutic efficacy, or stability (e.g., ex vivo shelf life and resistance to proteolytic degradation in vivo). GDF Trap polypeptides can also be produced by amino acid substitution, deletion, or addition. For instance, it is reasonable to expect that an isolated replacement of a leucine with an isoleucine or valine, an aspartate with a glutamate, a threonine with a serine, or a similar replacement of an amino acid with a structurally related amino acid (e.g., conservative mutations) will not have a major effect on the biological activity of the resulting molecule. Conservative replacements are those that take place within a family of amino acids that are related in their side chains. Whether a change in the amino acid sequence of a GDF Trap polypeptide results in a functional variant can be readily determined by assessing the ability of the GDF Trap polypeptide to produce a response in cells relative to the unmodified GDF Trap polypeptide or a wild-type ActRIIB polypeptide, or to bind to one or more ligands, such as activin, GDF-11 or myostatin as compared to the unmodified GDF Trap polypeptide or a wild-type ActRIIB polypeptide.

In certain specific embodiments, the present invention contemplates making mutations in the extracellular domain (also referred to as ligand-binding domain) of an ActRIIB polypeptide such that the ActRIIB polypeptide has altered ligand-binding activities (e.g., binding affinity or binding specificity). In certain cases, such GDF Trap polypeptides have altered (elevated or reduced) binding affinity for a specific ligand. In other cases, the GDF Trap polypeptides have altered binding specificity for ActRIIB ligands.

For example, the disclosure provides GDF Trap polypeptides that preferentially bind to GDF8/GDF11 relative to activins. The disclosure further establishes the desirability of such polypeptides for reducing off-target effects, although such selective variants may be less desirable for the treatment of severe diseases where very large gains in red blood cell levels may be needed for therapeutic effect and where some level of off-target effect is acceptable. For example, amino acid residues of the ActRIIB protein, such as E39, K55, Y60, K74, W78, D80, and F101, are in the ligand-binding pocket and mediate binding to its ligands such as activin and GDF8. Thus, the present invention provides a GDF Trap comprising an altered ligand-binding domain (e.g., GDF8-binding domain) of an ActRIIB receptor, which comprises one or more mutations at those amino acid residues. Optionally, the altered ligand-binding domain can have increased selectivity for a ligand such as GDF8 relative to a wild-type ligand-binding domain of an ActRIIB receptor. To illustrate, these mutations increase the selectivity of the altered ligand-binding domain for GDF8 over activin. Optionally, the altered ligand-binding domain has a ratio of $K_d$ for activin binding to $K_d$ for GDF8 binding that is at least 2, 5, 10, or even 100 fold greater relative to the ratio for the wild-type ligand-binding domain. Optionally, the altered ligand-binding domain has a ratio of $IC_{50}$ for inhibiting activin to $IC_{50}$ for inhibiting GDF8 that is at least 2, 5, 10, or even 100 fold greater relative to the wild-type ligand-binding domain. Optionally, the altered ligand-binding domain inhibits GDF8 with an $IC_{50}$ at least 2, 5, 10, or even 100 times less than the $IC_{50}$ for inhibiting activin.

As a specific example, the positively-charged amino acid residue Asp (D80) of the ligand-binding domain of ActRIIB can be mutated to a different amino acid residue to produce a GDF Trap polypeptide that preferentially binds to GDF8, but not activin. Preferably, the D80 residue is changed to an amino acid residue selected from the group consisting of: an uncharged amino acid residue, a negative amino acid residue, and a hydrophobic amino acid residue. As a further specific example, the hydrophobic residue, L79, can be altered to the acidic amino acids aspartic acid or glutamic acid to greatly reduce activin binding while retaining GDF11 binding. As will be recognized by one of skill in the art, most of the described mutations, variants or modifications may be made at the nucleic acid level or, in some cases, by post translational modification or chemical synthesis. Such techniques are well known in the art.

In certain embodiments, the present invention contemplates GDF Trap polypeptides having specific mutations in ActRIIB so as to alter the glycosylation of the ActRIIB polypeptide. Exemplary glycosylation sites in GDF Trap polypeptides are illustrated in FIG. 1 (e.g., the underlined NX(S/T) sites). Such mutations may be selected so as to introduce or eliminate one or more glycosylation sites, such as O-linked or N-linked glycosylation sites. Asparagine-linked glycosylation recognition sites generally comprise a tripeptide sequence, asparagine-X-threonine (where "X" is any amino acid) which is specifically recognized by appropriate cellular glycosylation enzymes. The alteration may also be made by the addition of, or substitution by, one or more serine or threonine residues to the sequence of the wild-type ActRIIB polypeptide (for O-linked glycosylation sites). A variety of amino acid substitutions or deletions at one or both of the first or third amino acid positions of a glycosylation recognition site (and/or amino acid deletion at the second position) results in non-glycosylation at the modified tripeptide sequence. Another means of increasing the number of carbohydrate moieties on a GDF Trap polypeptide is by chemical or enzymatic coupling of glycosides to the GDF Trap polypeptide. Depending on the coupling mode used, the sugar(s) may be attached to (a) arginine and histidine; (b) free carboxyl groups; (c) free sulfhydryl groups such as those of cysteine; (d) free hydroxyl groups such as those of serine, threonine, or hydroxyproline; (e) aromatic residues such as those of phenylalanine, tyrosine, or tryptophan; or (f) the amide group of glutamine. These methods are described in WO 87/05330 and in Aplin and Wriston (1981) CRC Crit. Rev. Biochem., pp. 259-306, incorporated by reference herein. Removal of one or more carbohydrate moieties present on a GDF Trap polypeptide may be accomplished chemically and/or enzymatically. Chemical deglycosylation may involve, for example, exposure of the GDF Trap polypeptide to the compound trifluoromethanesulfonic acid, or an equivalent compound. This treatment results in the cleavage of most or all sugars except the linking sugar (N-acetylglucosamine or N-acetylgalactosamine), while leaving the amino acid sequence intact. Chemical deglycosylation is further described by Hakimuddin et al. (1987) Arch. Biochem. Biophys. 259:52 and by Edge et al. (1981) Anal. Biochem. 118:131. Enzymatic cleavage of carbohydrate moieties on GDF Trap polypeptides can be achieved by the use of a variety of endo- and exo-glycosidases as described by Thotakura et al. (1987) Meth. Enzymol. 138:350. The sequence of a GDF Trap polypeptide may be adjusted, as appropriate, depending on the type of expression system used, as mammalian, yeast, insect and plant cells may all introduce differing glycosylation patterns that can be affected by the amino acid sequence of the peptide. In general, GDF Trap polypeptides for use in humans will be expressed in a mammalian cell line that provides proper glycosylation, such as HEK293 or CHO cell lines, although other mammalian expression cell lines are expected to be useful as well.

This disclosure further contemplates a method of generating variants, particularly sets of combinatorial variants of a GDF Trap polypeptide, including, optionally, truncation variants; pools of combinatorial mutants are especially useful for identifying GDF Trap sequences. The purpose of screening such combinatorial libraries may be to generate, for example, GDF Trap polypeptide variants which have altered properties, such as altered pharmacokinetics, or altered ligand binding. A variety of screening assays are provided below, and such assays may be used to evaluate variants. For example, a GDF Trap polypeptide variant may be screened for the ability to bind to an ActRIIB polypeptide, to prevent binding of an ActRIIB ligand to an ActRIIB polypeptide or to interfere with signaling caused by an ActRIIB ligand.

The activity of a GDF Trap polypeptide or its variants may also be tested in a cell-based or in vivo assay. For example, the effect of a GDF Trap polypeptide variant on the expression of genes involved in hematopoiesis may be assessed. This may, as needed, be performed in the presence of one or more recombinant ActRIIB ligand proteins (e.g., activin), and cells may be transfected so as to produce a GDF Trap polypeptide and/or variants thereof, and optionally, an ActRIIB ligand. Likewise, a GDF Trap polypeptide may be administered to a mouse or other animal, and one or more blood measurements, such as an RBC count, hemoglobin levels, hematocrit levels, iron stores, or reticulocyte count may be assessed using art recognized methods.

Combinatorially-derived variants can be generated which have a selective potency relative to a reference GDF Trap polypeptide. Such variant proteins, when expressed from recombinant DNA constructs, can be used in gene therapy protocols. Likewise, mutagenesis can give rise to variants which have intracellular half-lives dramatically different than the corresponding unmodified GDF Trap polypeptide. For example, the altered protein can be rendered either more stable or less stable to proteolytic degradation or other processes which result in destruction of, or otherwise inactivation of an unmodified GDF Trap polypeptide. Such variants, and the genes which encode them, can be utilized to alter GDF Trap polypeptide levels by modulating the half-life of the GDF Trap polypeptides. For instance, a short half-life can give rise to more transient biological effects and, when part of an inducible expression system, can allow tighter control of recombinant GDF Trap polypeptide levels within the cell. In an Fc fusion protein, mutations may be made in the linker (if any) and/or the Fc portion to alter the half-life of the protein.

In certain embodiments, the GDF Trap polypeptides of the invention may further comprise post-translational modifications in addition to any that are naturally present in the ActRIIB polypeptides. Such modifications include, but are not limited to, acetylation, carboxylation, glycosylation, phosphorylation, lipidation, and acylation. As a result, GDF Trap polypeptides may contain non-amino acid elements, such as polyethylene glycols, lipids, poly- or mono-saccharide, and phosphates. Effects of such non-amino acid elements on the functionality of a GDF Trap polypeptide may be tested as described herein for other GDF Trap polypeptide variants. When a GDF Trap polypeptide is produced in cells by cleaving a nascent form of the GDF Trap polypeptide, post-translational processing may also be important for correct folding and/or function of the protein. Different cells (such as CHO, HeLa, MDCK, 293, WI38, NIH-3T3 or HEK293) have specific cellular machinery and characteristic mechanisms for such post-translational activities and may be chosen to ensure the correct modification and processing of the GDF Trap polypeptides.

In certain aspects, GDF Trap polypeptides include fusion proteins having at least a portion of an ActRIIB polypeptide and one or more fusion domains. Well known examples of such fusion domains include, but are not limited to, polyhistidine, Glu-Glu, glutathione S transferase (GST), thioredoxin, protein A, protein G, an immunoglobulin heavy chain constant region (e.g., an Fc), maltose binding protein (MBP), or human serum albumin. A fusion domain may be selected so as to confer a desired property. For example, some fusion domains are particularly useful for isolation of the fusion proteins by affinity chromatography. For the purpose of affinity purification, relevant matrices for affinity chromatography, such as glutathione-, amylase-, and nickel- or cobalt-conjugated resins are used. Many of such matrices are available in "kit" form, such as the Pharmacia GST purification system and the QIAexpress™ system (Qiagen) useful with ($HIS_6$) fusion partners. As another example, a fusion domain may be selected so as to facilitate detection of the GDF Trap polypeptides. Examples of such detection domains include the various fluorescent proteins (e.g., GFP) as well as "epitope tags," which are usually short peptide sequences for which a specific antibody is available. Well known epitope tags for which specific monoclonal antibodies are readily available include FLAG, influenza virus haemagglutinin (HA), and c-myc tags. In some cases, the fusion domains have a protease cleavage site, such as for Factor Xa or Thrombin, which allows the relevant protease to partially digest the fusion proteins and thereby liberate the recombinant proteins therefrom. The liberated proteins can then be isolated from the fusion domain by subsequent chromatographic separation. In certain preferred embodiments, a GDF Trap polypeptide is fused with a domain that stabilizes the GDF Trap polypeptide in vivo (a "stabilizer" domain). By "stabilizing" is meant anything that increases serum half life, regardless of whether this is because of decreased destruction, decreased clearance by the kidney, or other pharmacokinetic effect. Fusions with the Fc portion of an immunoglobulin are known to confer desirable pharmacokinetic properties on a wide range of proteins Likewise, fusions to human serum albumin can confer desirable properties. Other types of fusion domains that may be selected include multimerizing (e.g., dimerizing, tetramerizing) domains and functional domains (that confer an additional biological function, such as further increasing red blood cell levels).

As a specific example, the present invention provides GDF Trap that is an ActRIIB-Fc fusion protein which comprises an extracellular (e.g., ligand-binding) domain of ActRIIB polypeptide fused to an Fc domain. The sequence of an exemplary Fc domain is shown below (SEQ ID NO: 6).

THTCPPCPAPELLGGPSVFLFPPKPKDTLMISRTPEVTCVVVD(A)V

SHEDPEVKFNWYVDGVEVHNAKTKPREEQYNSTYRVVSVLTVLHQDW

LNGKEYKCK(A)VSNKALPVPIEKTISKAKGQPREPQVYTLPPSREE

MTKNQVSLTCLVKGFYPSDIAVEWESNGQPENNYKTTPPVLDSDGPF

FLYSKLTVDKSRWQQGNVFSCSVMHEALHN(A)HYTQKSLSLSPGK*

Optionally, the Fc domain has one or more mutations at residues such as Asp-265, lysine 322, and Asn-434. In certain cases, the mutant Fc domain having one or more of these mutations (e.g., Asp-265 mutation) has reduced ability of binding to the Fcγ receptor relative to a wildtype Fc domain. In other cases, the mutant Fc domain having one or more of these mutations (e.g., Asn-434 mutation) has increased ability of binding to the MHC class I-related Fc-receptor (FcRN) relative to a wildtype Fc domain.

It is understood that different elements of the fusion proteins may be arranged in any manner that is consistent with the desired functionality. For example, a GDF Trap polypeptide may be placed C-terminal to a heterologous domain, or, alternatively, a heterologous domain may be placed C-terminal to a GDF Trap polypeptide. The GDF Trap polypeptide domain and the heterologous domain need not be adjacent in a fusion protein, and additional domains or amino acid sequences may be included C- or N-terminal to either domain or between the domains.

In certain embodiments, a GDF Trap fusion protein comprises an amino acid sequence as set forth in the formula A-B-C. The B portion is an N- and C-terminally truncated ActRIIB polypeptide consisting of the amino acid sequence corresponding to amino acids 26-132 of SEQ ID NO: 26. The A and C portions may be independently zero, one or more than one amino acids, and both the A and C portions when present are heterologous to B. The A and/or C portions may be attached to the B portion via a linker sequence. Exemplary linkers are include short polypeptide linkers such as 2-10, 2-5, 2-4, 2-3 Glycine residues, such as, for example, a Gly-Gly-Gly linker. Other suitable linkers are described herein above. In certain embodiments, a GDF Trap fusion protein comprises an amino acid sequence as set forth in the formula A-B-C, wherein A is a leader sequence, B consists of amino acids 26-132 of SEQ ID NO: 26, and C is a polypeptide portion that enhances one or more of in vivo stability, in vivo half life, uptake/administration, tissue localization or distribution, formation of protein complexes, and/or purification. In certain embodiments, a GDF Trap fusion protein comprises an amino acid sequence as set forth in the formula A-B-C, wherein A is a TPA leader sequence, B consists of amino acids 26-132 of SEQ ID NO: 26, and C is an immunoglobulin Fc domain. A preferred GDF Trap fusion protein comprises the amino acid sequence set forth in SEQ ID NO: 26.

In certain embodiments, the GDF Trap polypeptides of the present invention contain one or more modifications that are capable of stabilizing the GDF Trap polypeptides. For example, such modifications enhance the in vitro half life of the GDF Trap polypeptides, enhance circulatory half life of the GDF Trap polypeptides or reducing proteolytic degradation of the GDF Trap polypeptides. Such stabilizing modifications include, but are not limited to, fusion proteins (including, for example, fusion proteins comprising an GDF Trap polypeptide and a stabilizer domain), modifications of a glycosylation site (including, for example, addition of a glycosylation site to a GDF Trap polypeptide), and modifications of carbohydrate moiety (including, for example, removal of carbohydrate moieties from a GDF Trap polypeptide). In the case of fusion proteins, a GDF Trap polypeptide is fused to a stabilizer domain such as an IgG molecule (e.g., an Fc domain). As used herein, the term "stabilizer domain" not only refers to a fusion domain (e.g., Fc) as in the case of fusion proteins, but also includes nonproteinaceous modifications such as a carbohydrate moiety, or nonproteinaceous polymer, such as polyethylene glycol.

In certain embodiments, the present invention makes available isolated and/or purified forms of the GDF Trap polypeptides, which are isolated from, or otherwise substantially free of, other proteins.

In certain embodiments, GDF Trap polypeptides (unmodified or modified) of the invention can be produced by a variety of art-known techniques. For example, such GDF Trap polypeptides can be synthesized using standard protein chemistry techniques such as those described in Bodansky, M. Principles of Peptide Synthesis, Springer Verlag, Berlin (1993) and Grant G. A. (ed.), Synthetic Peptides: A User's Guide, W.H. Freeman and Company, New York (1992). In addition, automated peptide synthesizers are commercially available (e.g., Advanced ChemTech Model 396; Milligen/Biosearch 9600). Alternatively, the GDF Trap polypeptides, fragments or variants thereof may be recombinantly produced using various expression systems (e.g., E. coli, Chinese Hamster Ovary (CHO) cells, COS cells, baculovirus) as is well known in the art. In a further embodiment, the modified or unmodified GDF Trap polypeptides may be produced by digestion of recombinantly produced full-length GDF Trap polypeptides by using, for example, a protease, e.g., trypsin, thermolysin, chymotrypsin, pepsin, or paired basic amino acid converting enzyme (PACE). Computer analysis (using a commercially available software, e.g., MacVector, Omega, PCGene, Molecular Simulation, Inc.) can be used to identify proteolytic cleavage sites. Alternatively, such GDF Trap polypeptides may be produced from recombinantly produced full-length GDF Trap polypeptides such as standard techniques known in the art, such as by chemical cleavage (e.g., cyanogen bromide, hydroxylamine).

3. Nucleic Acids Encoding GDF Trap Polypeptides

In certain aspects, the invention provides isolated and/or recombinant nucleic acids encoding any of the GDF Trap polypeptides disclosed herein. SEQ ID NO: 4 encodes a naturally occurring ActRIIB precursor polypeptide, while SEQ ID NO: 5 encodes a soluble ActRIIB polypeptide, and SEQ ID NOs: 25, 27, 30 and 31 encode soluble GDF Traps. The subject nucleic acids may be single-stranded or double stranded. Such nucleic acids may be DNA or RNA molecules. These nucleic acids may be used, for example, in methods for making GDF Trap polypeptides or as direct therapeutic agents (e.g., in a gene therapy approach).

In certain aspects, the subject nucleic acids encoding GDF Trap polypeptides are further understood to include nucleic acids that are variants of SEQ ID NOs: 5, 25, 27, 30 and 31. Variant nucleotide sequences include sequences that differ by one or more nucleotide substitutions, additions or deletions, such as allelic variants; and will, therefore, include coding sequences that differ from the nucleotide sequence of the coding sequence designated in SEQ ID NOs: 5, 25, 27, 30 and 31.

In certain embodiments, the invention provides isolated or recombinant nucleic acid sequences that are at least 80%, 85%, 90%, 95%, 97%, 98%, 99% or 100% identical to SEQ ID NO: 5, 25, 27, 30 or 31. One of ordinary skill in the art will appreciate that nucleic acid sequences complementary to SEQ ID NO: 5, 25, 27, 30 or 31, and variants of SEQ ID NO: 5, 25, 27, 30 or 31, are also within the scope of this invention. In further embodiments, the nucleic acid sequences of the invention can be isolated, recombinant, and/or fused with a heterologous nucleotide sequence, or in a DNA library.

In other embodiments, nucleic acids of the invention also include nucleotide sequences that hybridize under highly stringent conditions to the nucleotide sequence designated in SEQ ID NO: 5, 25, 27, 30 or 31, complement sequence of SEQ ID NO: 5, 25, 27, 30 or 31, or fragments thereof. As discussed above, one of ordinary skill in the art will understand readily that appropriate stringency conditions which promote DNA hybridization can be varied. For example, one could perform the hybridization at 6.0× sodium chloride/sodium citrate (SSC) at about 45° C., followed by a wash of 2.0×SSC at 50° C. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In one embodiment, the invention provides nucleic acids which hybridize under low stringency conditions of 6×SSC at room temperature followed by a wash at 2×SSC at room temperature.

Isolated nucleic acids which differ from the nucleic acids as set forth in SEQ ID NO: 5, 25, 27, 30 or 31 due to degeneracy in the genetic code are also within the scope of the invention. For example, a number of amino acids are designated by more than one triplet. Codons that specify the same amino acid, or synonyms (for example, CAU and CAC are synonyms for histidine) may result in "silent" mutations which do not affect the amino acid sequence of the protein. In certain embodiments, the GDF Trap polypeptide will be encoded by an alternative nucleotide sequence. Alternative nucleotide sequences are degenerate with respect to the native GDF Trap nucleic acid sequence but still encode for the same fusion protein. In certain embodiments, the GDF Trap having SEQ ID NO: 26 is encoded by an alternative nucleic acid sequence comprising SEQ ID NO: 30. However, it is expected that DNA sequence polymorphisms that do lead to changes in the amino acid sequences of the subject proteins will exist among mammalian cells. One skilled in the art will appreciate that these variations in one or more nucleotides (up to about 3-5% of the nucleotides) of the nucleic acids encoding a particular protein may exist among individuals of a given species due to natural allelic variation. Any and all such nucleotide variations and resulting amino acid polymorphisms are within the scope of this invention.

In certain embodiments, the recombinant nucleic acids of the invention may be operably linked to one or more regulatory nucleotide sequences in an expression construct. Regulatory nucleotide sequences will generally be appropriate to the host cell used for expression. Numerous types of appropriate expression vectors and suitable regulatory sequences are known in the art for a variety of host cells. Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the invention. The promoters may be either naturally occurring promoters, or hybrid promoters that combine elements of more than one promoter. An expression construct may be present in a cell on an episome, such as a plasmid, or the expression construct may be inserted in a chromosome. In a preferred embodiment, the expression vector contains a selectable marker gene to allow the selection of transformed host cells. Selectable marker genes are well known in the art and will vary with the host cell used.

In certain aspects of the invention, the subject nucleic acid is provided in an expression vector comprising a nucleotide sequence encoding a GDF Trap polypeptide and operably linked to at least one regulatory sequence. Regulatory sequences are art-recognized and are selected to direct expression of the GDF Trap polypeptide. Accordingly, the term regulatory sequence includes promoters, enhancers, and other expression control elements. Exemplary regulatory sequences are described in Goeddel; *Gene Expression Technology: Methods in Enzymology*, Academic Press, San Diego, Calif. (1990). For instance, any of a wide variety of expression control sequences that control the expression of a DNA sequence when operatively linked to it may be used in these vectors to express DNA sequences encoding a GDF Trap polypeptide. Such useful expression control sequences, include, for example, the early and late promoters of SV40, tet promoter, adenovirus or cytomegalovirus immediate early promoter, RSV promoters, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., PhoS, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

A recombinant nucleic acid of the invention can be produced by ligating the cloned gene, or a portion thereof, into a vector suitable for expression in either prokaryotic cells, eukaryotic cells (yeast, avian, insect or mammalian), or both. Expression vehicles for production of a recombinant GDF Trap polypeptide include plasmids and other vectors. For instance, suitable vectors include plasmids of the types: pBR322-derived plasmids, pEMBL-derived plasmids, pEX-derived plasmids, pBTac-derived plasmids and pUC-derived plasmids for expression in prokaryotic cells, such as E. coli.

Some mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and in transformation of host organisms are well known in the art.

For other suitable expression systems for both prokaryotic and eukaryotic cells, as well as general recombinant procedures, see *Molecular Cloning A Laboratory Manual*, 2nd Ed., ed. by Sambrook, Fritsch and Maniatis (Cold Spring Harbor Laboratory Press, 1989) Chapters 16 and 17. In some instances, it may be desirable to express the recombinant polypeptides by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

In a preferred embodiment, a vector will be designed for production of the subject GDF Trap polypeptides in CHO cells, such as a Pcmv-Script vector (Stratagene, La Jolla, Calif.), pcDNA4 vectors (Invitrogen, Carlsbad, Calif.) and pCI-neo vectors (Promega, Madison, Wis.). As will be apparent, the subject gene constructs can be used to cause expression of the subject GDF Trap polypeptides in cells propagated in culture, e.g., to produce proteins, including fusion proteins or variant proteins, for purification.

This invention also pertains to a host cell transfected with a recombinant gene including a coding sequence (e.g., SEQ ID NO: 4, 5, 25, 27, 30 or 31) for one or more of the subject GDF Trap polypeptides. The host cell may be any prokaryotic or eukaryotic cell. For example, a GDF Trap polypeptide of the invention may be expressed in bacterial cells such as E. coli, insect cells (e.g., using a baculovirus expression system), yeast, or mammalian cells. Other suitable host cells are known to those skilled in the art.

Accordingly, the present invention further pertains to methods of producing the subject GDF Trap polypeptides. For example, a host cell transfected with an expression vector encoding a GDF Trap polypeptide can be cultured under appropriate conditions to allow expression of the GDF Trap polypeptide to occur. The GDF Trap polypeptide may be secreted and isolated from a mixture of cells and medium containing the GDF Trap polypeptide. Alternatively, the GDF Trap polypeptide may be retained cytoplasmically or in a membrane fraction and the cells harvested, lysed and the protein isolated. A cell culture includes host cells, media and other byproducts. Suitable media for cell culture are well known in the art. The subject GDF Trap polypeptides can be isolated from cell culture medium, host cells, or both, using techniques known in the art for purifying proteins, including ion-exchange chromatography, gel filtration chromatography, ultrafiltration, electrophoresis, and immunoaffinity purification with antibodies specific for particular epitopes of the GDF Trap polypeptides. In a preferred embodiment, the GDF Trap polypeptide is a fusion protein containing a domain which facilitates its purification.

In another embodiment, a fusion gene coding for a purification leader sequence, such as a poly-(His)/enterokinase cleavage site sequence at the N-terminus of the desired portion of the recombinant GDF Trap polypeptide, can allow purification of the expressed fusion protein by affinity chromatography using a $Ni^{2+}$ metal resin. The purification leader sequence can then be subsequently removed by treatment with enterokinase to provide the purified GDF Trap polypeptide (e.g., see Hochuli et al., (1987) *J. Chromatography* 411: 177; and Janknecht et al., *PNAS USA* 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, eds. Ausubel et al., John Wiley & Sons: 1992).

4. Screening Assays

In certain aspects, the present invention relates to the use of the subject GDF Trap polypeptides (e.g., soluble variant ActRIIB polypeptides) to identify compounds (agents) which are agonist or antagonists of ActRIIB polypeptides. Compounds identified through this screening can be tested to assess their ability to modulate red blood cell, hemoglobin and/or reticulocyte levels in vivo or in vitro. These compounds can be tested, for example, in animal models.

There are numerous approaches to screening for therapeutic agents for increasing red blood cell or hemoglobin levels by targeting ActRIIB signaling. In certain embodiments, high-throughput screening of compounds can be carried out to identify agents that perturb ActRIIB-mediated effects on a selected cell line. In certain embodiments, the assay is carried out to screen and identify compounds that specifically inhibit or reduce binding of an ActRIIB polypeptide to its binding partner, such as an ActRIIB ligand (e.g., activin, Nodal, GDF8, GDF11 or BMP7). Alternatively, the assay can be used to identify compounds that enhance binding of an ActRIIB polypeptide to its binding partner such as an ActRIIB ligand. In a further embodiment, the compounds can be identified by their ability to interact with an ActRIIB polypeptide.

A variety of assay formats will suffice and, in light of the present disclosure, those not expressly described herein will nevertheless be comprehended by one of ordinary skill in the art. As described herein, the test compounds (agents) of the invention may be created by any combinatorial chemical method. Alternatively, the subject compounds may be naturally occurring biomolecules synthesized in vivo or in vitro. Compounds (agents) to be tested for their ability to act as modulators of tissue growth can be produced, for example, by bacteria, yeast, plants or other organisms (e.g., natural products), produced chemically (e.g., small molecules, including peptidomimetics), or produced recombinantly. Test compounds contemplated by the present invention include non-peptidyl organic molecules, peptides, polypeptides, peptidomimetics, sugars, hormones, and nucleic acid molecules. In a specific embodiment, the test agent is a small organic molecule having a molecular weight of less than about 2,000 Daltons.

The test compounds of the invention can be provided as single, discrete entities, or provided in libraries of greater complexity, such as made by combinatorial chemistry. These libraries can comprise, for example, alcohols, alkyl halides, amines, amides, esters, aldehydes, ethers and other classes of organic compounds. Presentation of test compounds to the test system can be in either an isolated form or as mixtures of compounds, especially in initial screening steps. Optionally, the compounds may be optionally derivatized with other compounds and have derivatizing groups that facilitate isolation of the compounds. Non-limiting examples of derivatizing groups include biotin, fluorescein, digoxygenin, green fluorescent protein, isotopes, polyhistidine, magnetic beads, glutathione S transferase (GST), photoactivatable crosslinkers or any combinations thereof.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity or bioavailability of the test compound can be generally ignored in the in vitro system, the assay instead being focused primarily on the effect of the drug on the molecular target as may be manifest in an alteration of binding affinity between an ActRIIB polypeptide and its binding partner (e.g., an ActRIIB ligand).

Merely to illustrate, in an exemplary screening assay of the present invention, the compound of interest is contacted with an isolated and purified ActRIIB polypeptide which is ordinarily capable of binding to an ActRIIB ligand, as appropriate for the intention of the assay. To the mixture of the compound and ActRIIB polypeptide is then added to a composition containing an ActRIIB ligand. Detection and quantification of ActRIIB/ActRIIB ligand complexes provides a means for determining the compound's efficacy at inhibiting (or potentiating) complex formation between the ActRIIB polypeptide and its binding protein. The efficacy of the compound can be assessed by generating dose response curves from data obtained using various concentrations of the test compound. Moreover, a control assay can also be performed to provide a baseline for comparison. For example, in a control assay, isolated and purified ActRIIB ligand is added to a composition containing the ActRIIB polypeptide, and the formation of ActRIIB/ActRIIB ligand complex is quantitated in the absence of the test compound. It will be understood that, in general, the order in which the reactants may be admixed can be varied, and can be admixed simultaneously. Moreover, in place of purified proteins, cellular extracts and lysates may be used to render a suitable cell-free assay system.

Complex formation between the ActRIIB polypeptide and its binding protein may be detected by a variety of techniques. For instance, modulation of the formation of complexes can be quantitated using, for example, detectably labeled proteins such as radiolabeled (e.g., $^{32}P$, $^{35}S$, $^{14}C$ or $^{3}H$), fluorescently labeled (e.g., FITC), or enzymatically labeled ActRIIB polypeptide or its binding protein, by immunoassay, or by chromatographic detection.

In certain embodiments, the present invention contemplates the use of fluorescence polarization assays and fluorescence resonance energy transfer (FRET) assays in measuring, either directly or indirectly, the degree of interaction between an ActRIIB polypeptide and its binding protein. Further, other modes of detection, such as those based on optical waveguides (PCT Publication WO 96/26432 and U.S. Pat. No. 5,677,196), surface plasmon resonance (SPR), surface charge sensors, and surface force sensors, are compatible with many embodiments of the invention.

Moreover, the present invention contemplates the use of an interaction trap assay, also known as the "two hybrid assay," for identifying agents that disrupt or potentiate interaction between an ActRIIB polypeptide and its binding partner. See for example, U.S. Pat. No. 5,283,317; Zervos et al. (1993) Cell 72:223-232; Madura et al. (1993) J Biol Chem 268: 12046-12054; Bartel et al. (1993) Biotechniques 14:920-924; and Iwabuchi et al. (1993) Oncogene 8:1693-1696). In a specific embodiment, the present invention contemplates the use of reverse two hybrid systems to identify compounds (e.g., small molecules or peptides) that dissociate interactions between an ActRIIB polypeptide and its binding protein. See for example, Vidal and Legrain, (1999) Nucleic Acids Res 27:919-29; Vidal and Legrain, (1999) Trends Biotechnol 17:374-81; and U.S. Pat. Nos. 5,525,490; 5,955,280; and 5,965,368.

In certain embodiments, the subject compounds are identified by their ability to interact with an ActRIIB polypeptide. The interaction between the compound and the ActRIIB polypeptide may be covalent or non-covalent. For example, such interaction can be identified at the protein level using in vitro biochemical methods, including photo-crosslinking, radiolabeled ligand binding, and affinity chromatography (Jakoby W B et al., 1974, Methods in Enzymology 46: 1). In certain cases, the compounds may be screened in a mechanism based assay, such as an assay to detect compounds which bind to an ActRIIB polypeptide. This may include a solid phase or fluid phase binding event. Alternatively, the gene encoding an ActRIIB polypeptide can be transfected with a reporter system (e.g., β-galactosidase, luciferase, or green fluorescent protein) into a cell and screened against the library preferably by a high throughput screening or with individual members of the library. Other mechanism based binding assays may be used, for example, binding assays which detect changes in free energy. Binding assays can be performed with the target fixed to a well, bead or chip or captured by an immobilized antibody or resolved by capillary electrophoresis. The bound compounds may be detected usually using colorimetric or fluorescence or surface plasmon resonance.

5. Exemplary Therapeutic Uses

In certain embodiments, the GDF Trap polypeptides of the present invention can be used to increase red blood cell levels in mammals such as rodents and primates, and particularly human patients. Additionally, as shown herein, GDF Trap polypeptides may be used in combination with EPO receptor activators to achieve an increase in red blood cells at lower dose ranges. This may be beneficial in reducing the known off-target effects and risks associated with high doses of EPO receptor activators. In certain embodiments, the present invention provides methods of treating or preventing anemia in an individual in need thereof by administering to the individual a therapeutically effective amount of a GDF Trap polypeptide or a combination (or concomitant therapy) of a GDF Trap polypeptide and a EPO receptor activator. These methods may be used for therapeutic and prophylactic treatments of mammals, and particularly humans.

The GDF Trap polypeptides may be used in combination with EPO receptor activators to reduce the required dose of these activators in patients that are susceptible to adverse effects of EPO. The primary adverse effects of EPO are an excessive increase in the hematocrit or hemoglobin levels and polycythemia. Elevated hematocrit levels can lead to hypertension (more particularly aggravation of hypertension) and vascular thrombosis. Other adverse effects of EPO which have been reported, some of which related to hypertension, are headaches, influenza-like syndrome, obstruction of shunts, myocardial infarctions and cerebral convulsions due to thrombosis, hypertensive encephalopathy, and red cell blood cell applasia (Singibarti, (1994) J. Clin Investig 72 (suppl 6), S36-S43; Horl et al. (2000) Nephrol Dial Transplant 15 (suppl 4), 51-56; Delanty et al. (1997) Neurology 49, 686-689; Bunn (2002) N Engl J Med 346 (7), 522-523).

The rapid effect on red blood cell levels of the GDF Trap polypeptides disclosed herein indicate that these agents act by a different mechanism than EPO. Accordingly, these antagonists may be useful for increasing red blood cell and hemoglobin levels in patients that do not respond well to EPO. For example, a GDF Trap polypeptide may be beneficial for a patient in which administration of a normal to increased (>300 IU/kg/week) dose of EPO does not result in the increase of hemoglobin level up to the target level. Patients with an inadequate EPO response are found for all types of anemia, but higher numbers of non-responders have been observed particularly frequently in patients with cancers and patients with end-stage renal disease. An inadequate response to EPO can be either constitutive (i.e. observed upon the first treatment with EPO) or acquired (e.g. observed upon repeated treatment with EPO).

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample. The term "treating" as used herein includes prophylaxis of the named condition or amelioration or elimination of the condition once it has been established. In either case, prevention or treatment may be discerned in the diagnosis provided by a physician or other health care provider and the intended result of administration of the therapeutic agent.

As shown herein, GDF Trap polypeptides, optionally combined with an EPO receptor activator, may be used to increase red blood cell, hemoglobin or reticulocyte levels in healthy individuals, and such GDF Trap polypeptides may be used in selected patient populations. Examples of appropriate patient populations include those with undesirably low red blood cell or hemoglobin levels, such as patients having an anemia, and those that are at risk for developing undesirably low red blood cell or hemoglobin levels, such as those patients that are about to undergo major surgery or other procedures that may result in substantial blood loss. In one embodiment, a patient with adequate red blood cell levels is treated with a GDF Trap polypeptide to increase red blood cell levels, and then blood is drawn and stored for later use in transfusions.

GDF Trap polypeptides, optionally combined with an EPO receptor activator, disclosed herein may be used to increase red blood cell levels in patients having an anemia. When observing hemoglobin levels in humans, a level of less than normal for the appropriate age and gender category may be indicative of anemia, although individual variations are taken into account. For example, a hemoglobin level of 12 g/dl is generally considered the lower limit of normal in the general adult population. Potential causes include blood-loss, nutritional deficits, medication reaction, various problems with the bone marrow and many diseases. More particularly, anemia has been associated with a variety of disorders that include, for example, chronic renal failure, myelodysplastic syndrome, rheumatoid arthritis, bone marrow transplantation. Anemia may also be associated with the following conditions: solid tumors (e.g. breast cancer, lung cancer, colon cancer); tumors of the lymphatic system (e.g. chronic lymphocyte leukemia, non-Hodgkins and Hodgkins lymphomas); tumors of the hematopoietic system (e.g. leukemia, myelodysplastic syndrome, multiple myeloma); radiation therapy; chemotherapy (e.g. platinum containing regimens); inflammatory and autoimmune diseases, including, but not limited to, rheumatoid arthritis, other inflammatory arthritides, systemic lupus erythematosis (SLE), acute or chronic skin diseases (e.g. psoriasis), inflammatory bowel disease (e.g. Crohn's disease and ulcerative colitis); acute or chronic renal disease or failure including idiopathic or congenital conditions; acute or chronic liver disease; acute or chronic bleeding; situations where transfusion of red blood cells is not possible due to patient allo- or auto-antibodies and/or for religious reasons (e.g. some Jehovah's Witnesses); infections (e.g. malaria, osteomyelitis); hemoglobinopathies, including, for example, sickle cell disease, thalassemias; drug use or abuse, e.g. alcohol misuse; pediatric patients with anemia from any cause to avoid transfusion; and elderly patients or patients with underlying cardiopulmonary disease with anemia who cannot receive transfusions due to concerns about circulatory overload.

Myelodysplastic syndrome (MDS) is a diverse collection of hematological conditions characterized by ineffective production of myeloid blood cells and risk of transformation to acute mylogenous leukemia. In MDS patients, blood stem cells do not mature into healthy red blood cells, white blood cells, or platelets. MDS disorders include, for example, refractory anemia, refractory anemia with ringed sideroblasts, refractory anemia with excess blasts, refractory anemia with excess blasts in transformation, refractory cytopenia with multilineage dysplasia, and myelodysplastic syndrome associated with an isolated 5q chromosome abnormality. As these disorders manifest as irreversible defects in both quantity and quality of hematopoietic cells, most MDS patients are afflicted with chronic anemia. Therefore, MDS patients eventually require blood transfusions and/or treatment with growth factors (e.g., erythropoietin or G-CSF) to increase red blood cell levels. However, many MDS patients develop side-effect due to frequency of such therapies. For example, patients who receive frequent red blood cell transfusion can have tissue and organ damage from the buildup of extra iron. As demonstrated in the Examples below, GDF Trap polypeptides were used to treat anemia in a mouse model of MDS. Accordingly, GDF Trap polypeptides disclosed herein may be used to treat patients having MDS. In certain embodiments, patients suffering from MDS may be treated using a combination of a GDF Trap polypeptide in combination with an EPO receptor activator. In other embodiments, patient suffering from MDS may be treated using a combination of a GDF Trap polypeptide and one or more additional therapeutic agents for treating MDS including, for example, thalidomide, lenalidomide, azacitadine, decitabine, erythropoietins, deferoxamine, antithymocyte globulin, filgrastrim (G-CSF) and an erythropoietin signaling pathway agonist.

GDF Trap polypeptides, optionally combined with an EPO receptor activator, would be appropriate for treating anemias of hypoproliferative bone marrow, which are typically associated with little change in red blood cell (RBC) morphology. Hypoproliferative anemias include: 1) anemia of chronic disease, 2) anemia of kidney disease, and 3) anemia associated with hypometabolic states. In each of these types, endogenous erythropoietin levels are inappropriately low for the degree of anemia observed. Other hypoproliferative anemias include: 4) early-stage iron-deficient anemia, and 5) anemia caused by damage to the bone marrow. In these types, endogenous erythropoietin levels are appropriately elevated for the degree of anemia observed.

The most common type is anemia of chronic disease, which encompasses inflammation, infection, tissue injury, and conditions such as cancer, and is distinguished by both low erythropoietin levels and an inadequate response to erythropoietin in the bone marrow (Adamson, 2008, Harrison's Principles of Internal Medicine, 17th ed.; McGraw Hill, New York, pp 628-634). Many factors can contribute to cancer-related anemia. Some are associated with the disease process itself and the generation of inflamatory cytokines such as interleukin-1, interferon-gamma, and tumor necrosis factor (Bron et al., 2001, Semin Oncol 28 (Suppl 8):1-6). Among its effects, inflammation induces the key iron-regulatory peptide hepcidin, thereby inhibiting iron export from macrophages and generally limiting iron availability for erythropoiesis (Ganz, 2007, J Am Soc Nephrol 18:394-400). Blood loss through various routes can also contribute to cancer-related anemia. The prevalence of anemia due to cancer progression varies with cancer type, ranging from 5% in prostate cancer up to 90% in multiple myeloma. Cancer-related anemia has profound consequences for patients, including fatigue and reduced quality of life, reduced treatment efficacy, and increased mortality.

Chronic kidney disease is associated with hypoproliferative anemia that varies in severity with the degree of renal impairment. Such anemia is primarily due to inadequate production of erythropoietin and reduced survival of red blood cells. Chronic kidney disease usually proceeds gradually over a period of years or decades to end-stage (Stage-5) disease, at which point dialysis or kidney transplantation is required for patient survival. Anemia often develops early in this process and worsens as disease progresses. The clinical consequences of anemia of kidney disease are well-documented and include development of left ventricular hypertrophy, impaired cognitive function, reduced quality of life, and altered immune function (Levin et al., 1999, Am J Kidney Dis 27:347-354; Nissenson, 1992, Am J Kidney Dis 20 (Suppl 1):21-24; Revicki et al., 1995, Am J Kidney Dis 25:548-554; Gafter et al., 1994, Kidney Int 45:224-231). As demonstrated by the Applicants in a mouse model of chronic kidney disease (see Example below), a GDF Trap polypeptide, optionally combined with an EPO receptor activator, can be used to treat anemia of kidney disease.

Many conditions resulting in a hypometabolic rate can produce a mild-to-moderate hypoproliferative anemia. Among such conditions are endocrine deficiency states. For example, anemia can occur in Addison's disease, hypothyroidism, hyperparathyroidism, or males who are castrated or treated with estrogen. Mild-to-moderate anemia can also occur with reduced dietary intake of protein, a condition particularly prevalent in the elderly. Finally, anemia can develop in patients with chronic liver disease arising from nearly any cause (Adamson, 2008, Harrison's Principles of Internal Medicine, 17th ed.; McGraw Hill, New York, pp 628-634).

Anemia resulting from acute blood loss of sufficient volume, such as from trauma or postpartum hemorrhage, is known as acute post-hemorrhagic anemia. Acute blood loss initially causes hypovolemia without anemia since there is proportional depletion of RBCs along with other blood constituents. However, hypovolemia will rapidly trigger physiologic mechanisms that shift fluid from the extravascular to the vascular compartment, which results in hemodilution and anemia. If chronic, blood loss gradually depletes body iron stores and eventually leads to iron deficiency. As demonstrated by the Applicants in a mouse model (see Example below), a GDF Trap polypeptide, optionally combined with an EPO receptor activator, can be used to speed recovery from anemia of acute blood loss.

Iron-deficiency anemia is the final stage in a graded progression of increasing iron deficiency which includes negative iron balance and iron-deficient erythropoiesis as intermediate stages. Iron deficiency can result from increased iron demand, decreased iron intake, or increased iron loss, as exemplified in conditions such as pregnancy, inadequate diet, intestinal malabsorption, acute or chronic inflammation, and acute or chronic blood loss. With mild-to-moderate anemia of this type, the bone marrow remains hypoproliferative, and RBC morphology is largely normal; however, even mild anemia can result in some microcytic hypochromic RBCs, and the transition to severe iron-deficient anemia is accompanied by hyperproliferation of the bone marrow and increasingly prevalent microcytic and hypochromic RBCs (Adamson, 2008, Harrison's Principles of Internal Medicine, 17th ed.; McGraw Hill, New York, pp 628-634). Appropriate therapy for iron-deficiency anemia depends on its cause and severity, with oral iron preparations, parenteral iron formulations, and RBC transfusion as major conventional options. A GDF Trap polypeptide, optionally combined with an EPO receptor activator, could be used to treat chronic iron-deficiency anemias alone or in combination with conventional therapeutic approaches, particularly to treat anemias of multifactoral origin.

Hypoproliferative anemias can result from primary dysfunction or failure of the bone marrow, instead of dysfunction secondary to inflammation, infection, or cancer progression. Prominent examples would be myelosuppression caused by cancer chemotherapeutic drugs or cancer radiation therapy. A broad review of clinical trials found that mild anemia can occur in 100% of patients after chemotherapy, while more severe anemia can occur in up to 80% of such patients (Groopman et al., 1999, J Natl Cancer Inst 91:1616-1634). Myelosuppressive drugs include: 1) alkylating agents such as nitrogen mustards (e.g., melphalan) and nitrosoureas (e.g., streptozocin); 2) antimetabolites such as folic acid antagonists (e.g., methotrexate), purine analogs (e.g., thioguanine), and pyrimidine analogs (e.g., gemcitabine); 3) cytotoxic antibotics such as anthracyclines (e.g., doxorubicin); 4) kinase inhibitors (e.g., gefitinib); 5) mitotic inhibitors such as taxanes (e.g., paclitaxel) and vinca alkaloids (e.g., vinorelbine); 6) monoclonal antibodies (e.g., rituximab); and 7) topoisomerase inhibitors (e.g., topotecan and etoposide). As demonstrated in a mouse model of chemotherapy-induced anemia (see Example below), a GDF Trap polypeptide, optionally combined with an EPO receptor activator, can be used to treat anemia caused by chemotherapeutic agents and/or radiation therapy.

GDF Trap polypeptides, optionally combined with an EPO receptor activator, would also be appropriate for treating anemias of disordered RBC maturation, which are characterized in part by undersized (microcytic), oversized (macrocytic), misshapen, or abnormally colored (hypochromic) RBCs.

Patients may be treated with a dosing regimen intended to restore the patient to a target hemoglobin level, usually between about 10 g/dl and about 12.5 g/dl, and typically about 11.0 g/dl (see also Jacobs et al. (2000) Nephrol Dial Transplant 15, 15-19), although lower target levels may cause fewer cardiovascular side effects. Alternatively, hematocrit levels (percentage of the volume of a blood sample occupied by the cells) can be used as a measure for the condition of red blood cells. Hematocrit levels for healthy individuals range from 41 to 51% for adult males and from 35 to 45% for adult females. Target hematocrit levels are usually around 30-33%. Moreover, hemoglobin/hematocrit levels vary from person to person. Thus, optimally, the target hemoglobin/hematocrit level can be individualized for each patient.

In certain embodiments, the present invention provides methods for managing a patient that has been treated with, or is a candidate to be treated with, a GDF Trap polypeptide by measuring one or more hematologic parameters in the patient. The hematologic parameters may be used to evaluate appropriate dosing for a patient who is a candidate to be treated with a GDF Trap polypeptide, to monitor the hematologic parameters during treatment with a GDF Trap polypeptide, to evaluate whether to adjust the dosage during treatment with a GDF Trap polypeptide, and/or to evaluate an appropriate maintenance dose of a GDF Trap polypeptide. If one or more of the hematologic parameters are outside the normal level, dosing with a GDF Trap polypeptide may be reduced, delayed or terminated.

Hematologic parameters that may be measured in accordance with the methods provided herein include, for example, red blood cell levels, blood pressure, iron stores, and other agents found in bodily fluids that correlate with increased red blood cell levels, using art recognized methods. Such parameters may be determined using a blood sample from a patient. Increases in red blood cell levels, hemoglobin levels, and/or hematocrit levels may cause increases in blood pressure.

In one embodiment, if one or more hematologic parameters are outside the normal range, or on the high side of normal, in a patient who is a candidate to be treated with a GDF Trap polypeptide then onset of administration of the GDF Trap polypeptide may be delayed until the hematologic parameters have returned to a normal or acceptable level either naturally or via therapeutic intervention. For example, if a candidate patient is hypertensive or prehypertensive, then the patient may be treated with a blood pressure lowering agent in order to reduce the patient's blood pressure. Any blood pressure lowering agent appropriate for the individual patient's condition may be used including, for example, diuretics, adrenergic inhibitors (including alpha blockers and beta blockers), vasodilators, calcium channel blockers, angiotensin-converting enzyme (ACE) inhibitors, or angiotensin II receptor blockers. Blood pressure may alternatively be treated using a diet and exercise regimen. Similarly, if a candidate patient has iron stores that are lower than normal, or on the low side of normal, then the patient may be treated with an appropriate regimen of diet and/or iron supplements until the patient's iron stores have returned to a normal or acceptable level. For patients having higher than normal red blood cell levels and/or hemoglobin levels, then administration of the GDF Trap polypeptide may be delayed until the levels have returned to a normal or acceptable level.

In certain embodiments, if one or more hematologic parameters are outside the normal range, or on the high side of normal, in a patient who is a candidate to be treated with a GDF Trap polypeptide then the onset of administration may be not be delayed. However, the dosage amount or frequency of dosing of the GDF Trap polypeptide may be set at an amount that would reduce the risk of an unacceptable increase in the hematologic parameters arising upon administration of the GDF Trap polypeptide. Alternatively, a therapeutic regimen may be developed for the patient that combines a GDF Trap polypeptide with a therapeutic agent that addresses the undesirable level of the hematologic parameter. For example, if the patient has elevated blood pressure, then a therapeutic regimen involving administration of a GDF Trap polypeptide and a blood pressure lowering agent may be designed. For a patient having lower than desired iron stores, a therapeutic regimen of a GDF Trap polypeptide and iron supplementation may be developed.

In one embodiment, baseline parameter(s) for one or more hematologic parameters may be established for a patient who is a candidate to be treated with a GDF Trap polypeptide and an appropriate dosing regimen establish for that patient based on the baseline value(s). Alternatively, established baseline parameters based on a patient's medical history could be used to inform an appropriate GDF Trap polypeptide dosing regimen for a patient. For example, if a healthy patient has an established baseline blood pressure reading that is above the defined normal range it may not be necessary to bring the patient's blood pressure into the range that is considered normal for the general population prior to treatment with the GDF Trap polypeptide. A patient's baseline values for one or more hematologic parameters prior to treatment with a GDF Trap polypeptide may also be used as the relevant comparative values for monitoring any changes to the hematologic parameters during treatment with the GDF Trap polypeptide.

In certain embodiments, one or more hematologic parameters are measured in patients who are being treated with a GDF Trap polypeptide. The hematologic parameters may be used to monitor the patient during treatment and permit adjustment or termination of the dosing with the GDF Trap polypeptide or additional dosing with another therapeutic agent. For example, if administration of a GDF Trap polypeptide results in an increase in blood pressure, red blood cell level, or hemoglobin level, or a reduction in iron stores, then the dose of the GDF Trap polypeptide may be reduced in amount or frequency in order to decrease the effects of the GDF Trap polypeptide on the one or more hematologic parameters. If administration or a GDF Trap polypeptide results in a change in one or more hematologic parameters that is adverse to the patient, then the dosing of the GDF Trap polypeptide may be terminated either temporarily, until the hematologic parameter(s) return to an acceptable level, or permanently. Similarly, if one or more hematologic parameters are not brought within an acceptable range after reducing the dose or frequency of administration of the GDF Trap polypeptide then the dosing may be terminated. As an alternative, or in addition to, reducing or terminating the dosing with the GDF Trap polypeptide, the patient may be dosed with an additional therapeutic agent that addresses the undesirable level in the hematologic parameter(s), such as, for example, a blood pressure lowering agent or an iron supplement. For example, if a patient being treated with a GDF Trap polypeptide has elevated blood pressure, then dosing with the GDF Trap polypeptide may continue at the same level and a blood pressure lowering agent is added to the treatment regimen, dosing with the GDF Trap polypeptide may be reduce (e.g., in amount and/or frequency) and a blood pressure lowering agent is added to the treatment regimen, or dosing with the GDF Trap polypeptide may be terminated and the patient may be treated with a blood pressure lowering agent.

In certain embodiments, patients being treated with a GDF Trap polypeptide, or candidate patients to be treated with a GDF Trap polypeptide, are patients in need of muscle growth, such as patients suffering from, or at risk of developing, a neuromuscular disorder or musculogenerative disorder. For example, patients or candidate patients may be suffering from, or at risk for developing, Lou Gehrig's disease (ALS), cancer anorexia-cachexia syndrome, muscular dystrophy, muscle atrophy, congestive obstructive pulmonary disease (and muscle wasting associated with COPD), muscle wasting syndrome, sarcopenia, or cachexia. Muscular dystrophy refers to a group of degenerative muscle diseases characterized by gradual weakening and deterioration of skeletal muscles and sometimes the heart and respiratory muscles. Exemplary muscular dystrophies that can be treated with a regimen including the subject GDF Trap polypeptides include: Duchenne Muscular Dystrophy (DMD), Becker Muscular Dystrophy (BMD), Emery-Dreifuss Muscular Dystrophy (EDMD), Limb-Girdle Muscular Dystrophy (LGMD), Facioscapulohumeral Muscular Dystrophy (FSH or FSHD) (also known as Landouzy-Dejerine), Myotonic Dystrophy (MMD) (also known as Steinert's Disease), Oculopharyngeal Muscular Dystrophy (OPMD), Distal Muscular Dystrophy (DD), Congenital Muscular Dystrophy (CMD).

6. Pharmaceutical Compositions

In certain embodiments, compounds (e.g., GDF Trap polypeptides) of the present invention are formulated with a pharmaceutically acceptable carrier. For example, a GDF Trap polypeptide can be administered alone or as a component of a pharmaceutical formulation (therapeutic composition). The subject compounds may be formulated for administration in any convenient way for use in human or veterinary medicine.

In certain embodiments, the therapeutic method of the invention includes administering the composition systemically, or locally as an implant or device. When administered, the therapeutic composition for use in this invention is, of course, in a pyrogen-free, physiologically acceptable form. Therapeutically useful agents other than the GDF Trap polypeptides which may also optionally be included in the composition as described above, may be administered simultaneously or sequentially with the subject compounds (e.g., GDF Trap polypeptides) in the methods of the invention.

Typically, compounds will be administered parenterally. Pharmaceutical compositions suitable for parenteral administration may comprise one or more GDF Trap polypeptides in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Further, the composition may be encapsulated or injected in a form for delivery to a target tissue site (e.g., bone marrow). In certain embodiments, compositions of the present invention may include a matrix capable of delivering one or more therapeutic compounds (e.g., GDF Trap polypeptides) to a target tissue site (e.g., bone marrow), providing a structure for the developing tissue and optimally capable of being resorbed into the body. For example, the matrix may provide slow release of the GDF Trap polypeptides. Such matrices may be formed of materials presently in use for other implanted medical applications.

The choice of matrix material is based on biocompatibility, biodegradability, mechanical properties, cosmetic appearance and interface properties. The particular application of the subject compositions will define the appropriate formulation. Potential matrices for the compositions may be biodegradable and chemically defined calcium sulfate, tricalciumphosphate, hydroxyapatite, polylactic acid and polyanhydrides. Other potential materials are biodegradable and biologically well defined, such as bone or dermal collagen. Further matrices are comprised of pure proteins or extracellular matrix components. Other potential matrices are non-biodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalciumphosphate. The bioceramics may be altered in composition, such as in calcium-aluminate-phosphate and processing to alter pore size, particle size, particle shape, and biodegradability.

In certain embodiments, methods of the invention can be administered for orally, e.g., in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of an agent as an active ingredient. An agent may also be administered as a bolus, electuary or paste.

In solid dosage forms for oral administration (capsules, tablets, pills, dragees, powders, granules, and the like), one or more therapeutic compounds of the present invention may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents.

Suspensions, in addition to the active compounds, may contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

The compositions of the invention may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

It is understood that the dosage regimen will be determined by the attending physician considering various factors which modify the action of the subject compounds of the invention (e.g., GDF Trap polypeptides). The various factors include, but are not limited to, the patient's red blood cell count, hemoglobin level or other diagnostic assessments, the desired target red blood cell count, the patient's age, sex, and diet, the severity of any disease that may be contributing to a depressed red blood cell level, time of administration, and other clinical factors. The addition of other known growth factors to the final composition may also affect the dosage. Progress can be monitored by periodic assessment of red blood cell and hemoglobin levels, as well as assessments of reticulocyte levels and other indicators of the hematopoietic process.

In certain embodiments, the present invention also provides gene therapy for the in vivo production of GDF Trap polypeptides. Such therapy would achieve its therapeutic effect by introduction of the GDF Trap polynucleotide sequences into cells or tissues having the disorders as listed above. Delivery of GDF Trap polynucleotide sequences can be achieved using a recombinant expression vector such as a chimeric virus or a colloidal dispersion system. Preferred for therapeutic delivery of GDF Trap polynucleotide sequences is the use of targeted liposomes.

Various viral vectors which can be utilized for gene therapy as taught herein include adenovirus, herpes virus, vaccinia, or an RNA virus such as a retrovirus. The retroviral vector may be a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. Retroviral vectors can be made target-specific by attaching, for example, a sugar, a glycolipid, or a protein. Preferred targeting is accomplished by using an antibody. Those of skill in the art will recognize that specific polynucleotide sequences can be inserted into the retroviral genome or attached to a viral envelope to allow target specific delivery of the retroviral vector containing the GDF Trap polynucleotide.

Alternatively, tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for GDF Trap polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. RNA, DNA and intact virions can be encapsulated within the aqueous interior and be delivered to cells in a biologically active form (see e.g., Fraley, et al., Trends Biochem. Sci., 6:77, 1981). Methods for efficient gene transfer using a liposome vehicle, are known in the art, see e.g., Mannino, et al., Biotechniques, 6:682, 1988. The composition of the liposome is usually a combination of phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Illustrative phospholipids include egg phosphatidylcholine, dipalmitoylphosphatidylcholine, and distearoylphosphatidylcholine. The targeting of liposomes is also possible based on, for example, organ-specificity, cell-specificity, and organelle-specificity and is known in the art.

EXEMPLIFICATION

The invention now being generally described, it will be more readily understood by reference to the following examples, which are included merely for purposes of illustration of certain embodiments and embodiments of the present invention, and are not intended to limit the invention.

Example 1

Generation of a GDF Trap

Applicants constructed a GDF Trap as follows. A polypeptide having a modified extracellular domain of ActRIIB with greatly reduced activin A binding relative to GDF11 and/or myostatin (as a consequence of a leucine-to-aspartate substitution at position 79 in SEQ ID NO: 1) was fused to a human or mouse Fc domain with a minimal linker (three glycine amino acids) in between. The constructs are referred to as ActRIIB(L79D 20-134)-hFc and ActRIIB(L79D 20-134)-mFc, respectively. Alternative forms with a glutamate rather than an aspartate at position 79 performed similarly (L79E). Alternative forms with an alanine rather than a valine at position 226 with respect to SEQ ID NO: 7, below were also generated and performed equivalently in all respects tested. The aspartate at position 79 (relative to SEQ ID NO: 1, or position 60 relative to SEQ ID NO: 7) is highlighted in gray below. The valine at position 226 relative to SEQ ID NO: 7 is also highlighted in gray below.

The GDF Trap ActRIIB(L79D 20-134)-hFc is shown below as purified from CHO cell lines (SEQ ID NO: 7).

GRGEAETRECIYYNANWELERTNQSGLERCEGEQDKRLHCYASWRNS

SGTIELVKKGCW D DDFNCYDRQECVATEENPQVYFCCCEGNFCNERF

THLPEAGGPEVTYEPPPTAPT<u>GGGTHTCPPCPAPELLGGPSVFLFPP</u>

<u>KPKDTLMISRTPEVTCVVVDVSHEDPEVKFNWYVDGVEVHNAKTKPR</u>

<u>EEQYNSTYRVVSVLTVLHQDWLNGKEYKCKVSNKALP</u>V<u>PIEKTISKA</u>

<u>KGQPREPQVYTLPPSREEMTKNQVSLTCLVKGFYPSDIAVEWESNGQ</u>

<u>PENNYKTTPPVLDSDGSFFLYSKLTVDKSRWQQGNVFSCSVMHEALH</u>

<u>NHYTQKSLSLSPGK</u>

The ActRIIB-derived portion of the GDF Trap has an amino acid sequence set forth below (SEQ ID NO: 32), and that portion could be used as a monomer or as a non-Fc fusion protein as a monomer, dimer or greater order complex.

(SEQ ID NO: 32)
GRGEAETRECIYYNANWELERTNQSGLERCEGEQDKRLHCYASWRN

SSGTIELVKKGCW D DDFNCYDRQECVATEENPQVYFCCCEGNFCNE

RFTHLPEAGGPEVTYEPPPTAPT

The GDF Trap protein was expressed in CHO cell lines. Three different leader sequences were considered:
(i) Honey bee melittin (HBML): MKFLVNVALVFMVVYI-SYIYA (SEQ ID NO: 8)
(ii) Tissue Plasminogen Activator (TPA): MDAMKRGLCCVLLLCGAVFVSP (SEQ ID NO: 9)
(iii) Native: MTAPWVALALLWGSLCAGS (SEQ ID NO: 10).

The selected form employs the TPA leader and has the following unprocessed amino acid sequence:

(SEQ ID NO: 11)
<u>MDAMKRGLCCVLLLCGAVFVSPGAS</u>GRGEAETRECIYYNANWELERT

NQSGLERCEGEQDKRLHCYASWRNSSGTIELVKKGCWDDDFNCYDRQ

ECVATEENPQVYFCCCEGNFCNERFTHLPEAGGPEVTYEPPPTAPT<u>G</u>

<u>GGTHTCPPCPAPELLGGPSVFLFPPKPKDTLMISRTPEVTCVVVDVS</u>

<u>HEDPEVKFNWYVDGVEVHNAKTKPREEQYNSTYRVVSVLTVLHQDWL</u>

<u>NGKEYKCKVSNKALPVPIEKTISKAKGQPREPQVYTLPPSREEMTKN</u>

<u>QVSLTCLVKGFYPSDIAVEWESNGQPENNYKTTPPVLDSDGSFFLYS</u>

<u>KLTVDKSRWQQGNVFSCSVMHEALHNHYTQKSLSLSPGK</u>

This polypeptide is encoded by the following nucleic acid sequence (SEQ ID NO:12):

```
A TGGATGCAAT GAAGAGAGGG CTCTGCTGTG TGCTGCTGCT

GTGTGGAGCA GTCTTCGTTT CGCCCGGCGC CTCTGGGCGT

GGGGAGGCTG AGACACGGGA GTGCATCTAC TACAACGCCA

ACTGGGAGCT GGAGCGCACC AACCAGAGCG GCCTGGAGCG

CTGCGAAGGC GAGCAGGACA AGCGGCTGCA CTGCTACGCC

TCCTGGCGCA ACAGCTCTGG CACCATCGAG CTCGTGAAGA

AGGGCTGCTG GGACGATGAC TTCAACTGCT ACGATAGGCA

GGAGTGTGTG GCCACTGAGG AGAACCCCCA GGTGTACTTC

TGCTGCTGTG AAGGCAACTT CTGCAACGAG CGCTTCACTC

ATTTGCCAGA GGCTGGGGGC CCGGAAGTCA CGTACGAGCC

ACCCCCGACA GCCCCCACCG GTGGTGGAAC TCACACATGC

CCACCGTGCC CAGCACCTGA ACTCCTGGGG GGACCGTCAG

TCTTCCTCTT CCCCCCAAAA CCCAAGGACA CCCTCATGAT

CTCCCGGACC CCTGAGGTCA CATGCGTGGT GGTGGACGTG

AGCCACGAAG ACCCTGAGGT CAAGTTCAAC TGGTACGTGG

ACGGCGTGGA GGTGCATAAT GCCAAGACAA AGCCGCGGGA

GGAGCAGTAC AACAGCACGT ACCGTGTGGT CAGCGTCCTC

ACCGTCCTGC ACCAGGACTG GCTGAATGGC AAGGAGTACA

AGTGCAAGGT CTCCAACAAA GCCCTCCCAG TCCCCATCGA

GAAAACCATC TCCAAAGCCA AAGGGCAGCC CCGAGAACCA

CAGGTGTACA CCCTGCCCCC ATCCCGGGAG GAGATGACCA

AGAACCAGGT CAGCCTGACC TGCCTGGTCA AAGGCTTCTA

TCCCAGCGAC ATCGCCGTGG AGTGGGAGAG CAATGGGCAG

CCGGAGAACA ACTACAAGAC CACGCCTCCC GTGCTGGACT

CCGACGGCTC CTTCTTCCTC TATAGCAAGC TCACCGTGGA

CAAGAGCAGG TGGCAGCAGG GGAACGTCTT CTCATGCTCC

GTGATGCATG AGGCTCTGCA CAACCACTAC ACGCAGAAGA

GCCTCTCCCT GTCTCCGGGT AAATGA
```

Purification could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange. In an example of a purification scheme, the cell culture medium is passed over a protein A column, washed in 150 mM Tris/NaCl (pH 8.0), then washed in 50 mM Tris/NaCl (pH 8.0) and eluted with 0.1 M glycine, pH 3.0. The low pH eluate is kept at room temperature for 30 minutes as a viral clearance step. The eluate is then neutralized and passed over a Q sepharose ion exchange column and washed in 50 mM Tris pH 8.0, 50 mM NaCl, and eluted in 50 mM Tris pH 8.0, with an NaCl concentration between 150 mM and 300 mM. The eluate is then changed into 50 mM Tris pH 8.0, 1.1 M ammonium sulfate and passed over a phenyl sepharose column, washed, and eluted in 50 mM Tris pH 8.0 with ammonium sulfate between 150 and 300 mM. The eluate is dialyzed and filtered for use.

Additional GDF Traps (ActRIIB-Fc fusion proteins modified so as to reduce the ratio of activin A binding relative to myostatin or GDF11) are described in PCT/US2008/001506 and WO 2006/012627, incorporated by reference herein.

Example 2

Bioassay for GDF-11 and Activin-Mediated Signaling

An A-204 Reporter Gene Assay was used to evaluate the effects of ActRIIB-Fc proteins and GDF Traps on signaling by GDF-11 and Activin A. Cell line: Human Rhabdomyosarcoma (derived from muscle). Reporter vector: pGL3 (CAGA)12 (Described in Dennler et al, 1998, EMBO 17: 3091-3100). The CAGA12 motif is present in TGF-Beta responsive genes (PAI-1 gene), so this vector is of general use for factors signaling through Smad2 and 3.

Day 1: Split A-204 cells into 48-well plate.
Day 2: A-204 cells transfected with 10 ug pGL3(CAGA)12 or pGL3(CAGA)12(10 ug)+pRLCMV (1 ug) and Fugene.
Day 3: Add factors (diluted into medium+0.1% BSA). Inhibitors need to be preincubated with Factors for 1 hr before adding to cells. 6 hrs later, cells rinsed with PBS, and lyse cells.

This is followed by a Luciferase assay. In the absence of any inhibitors, Activin A showed 10 fold stimulation of reporter gene expression and an ED50~2 ng/ml. GDF-11: 16 fold stimulation, ED50: ~1.5 ng/ml.

ActRIIB(20-134) is a potent inhibitor of activin, GDF-8 and GDF-11 activity in this assay. Variants were tested in this assay as well.

Example 3

GDF-11 Inhibition by N-Terminal and C-Terminal Truncations

Variants of ActRIIB(20-134)-hFc with truncations at the N-terminus and/or C-terminus were generated and tested for activity as inhibitors of GDF-11 and activin. The activities are shown below (as measured in conditioned media):

C-Terminal ActRIIB-hFc Truncations:

|  | IC50 (ng/mL) | |
| --- | --- | --- |
|  | GDF-11 | Activin |
| ActRIIB(20-134)-hFc | 45 | 22 |
| ActRIIB(20-132)-hFc | 87 | 32 |
| ActRIIB(20-131)-hFc | 120 | 44 |
| ActRIIB(20-128)-hFc | 130 | 158 |

As can be seen, truncations of three (ending with . . . PPT), six (ending with . . . YEP) or more amino acids at the C-terminus causes a threefold or greater decrease in the activity of the molecule. The truncation of the final 15 amino acids of the ActRIIB portion causes a greater loss of activity (see WO2006/012627).

Amino terminal truncations were made in the background of an ActRIIB(20-131)-hFc protein. The activities are shown below (as measured in conditioned media):

N-Terminal ActRIIB-hFc Truncations:

|  | IC50 (ng/mL) | |
| --- | --- | --- |
|  | GDF-11 | Activin |
| ActRIIB(20-131)-hFc (GRG . . . ) | 183 | 201 |
| ActRIIB(21-131)-hFc (RGE . . . ) | 121 | 325 |
| ActRIIB(22-131)-hFc (GEA . . . ) | 71 | 100 |
| ActRIIB(23-131)-hFc (EAE . . . ) | 60 | 43 |
| ActRIIB(24-131)-hFc (AET . . . ) | 69 | 105 |

Accordingly, truncations of two, three or four amino acids from the N-terminus lead to the production of a more active protein than the versions with a full-length extracellular domain. Additional experiments show that a truncation of five amino acids, ActRIIB(25-131)-hFc has activity equivalent to the untruncated form, and additional deletions at the N-terminus continue to degrade the activity of the protein. Therefore, optimal constructs will have a C-terminus ending between amino acid 133-134 of SEQ ID NO: 1 and an N-terminus beginning at amino acids 22-24 of SEQ ID NO: 1. An N-terminus corresponding to amino acids 21 or 25 will give activity that is similar to the ActRIIB(20-134)-hFc construct. These truncations may also be used in the context of GDF Traps, such as an L79D or L79E variant.

Example 4

ActRIIB-Fc Variants, Cell-Based Activity

Activity of ActRIIB-Fc proteins and GDF Traps was tested in a cell based assay, as described above. Results are summarized in the table below. Some variants were tested in different C-terminal truncation constructs. As discussed above, truncations of five or fifteen amino acids caused reduction in activity. The GDF Traps (L79D and L79E variants) showed substantial loss of activin binding while retaining almost wild-type inhibition of GDF-11.

Soluble ActRIIB-Fc Binding to GDF11 and Activin A:

| ActRIIB-Fc Variations | Portion of ActRIIB (corresponds to amino acids of SEQ ID NO: 1) | GDF11 Inhibition Activity | Activin Inhibition Activity |
| --- | --- | --- | --- |
| R64 | 20-134 | +++ (approx. $10^{-8}$ M $K_I$) | +++ (approx. $10^{-8}$ M $K_I$) |
| A64 | 20-134 | + (approx. $10^{-6}$ M $K_I$) | + (approx. $10^{-6}$ M $K_I$) |

| ActRIIB-Fc Variations | Portion of ActRIIB (corresponds to amino acids of SEQ ID NO: 1) | GDF11 Inhibition Activity | Activin Inhibition Activity |
|---|---|---|---|
| R64 | 20-129 | +++ | +++ |
| R64 K74A | 20-134 | ++++ | ++++ |
| R64 A24N | 20-134 | +++ | +++ |
| R64 A24N | 20-119 | ++ | ++ |
| R64 A24N K74A | 20-119 | + | + |
| R64 L79P | 20-134 | + | + |
| R64 L79P K74A | 20-134 | + | + |
| R64 L79D | 20-134 | +++ | + |
| R64 L79E | 20-134 | +++ | + |
| R64K | 20-134 | +++ | +++ |
| R64K | 20-129 | +++ | +++ |
| R64 P129S P130A | 20-134 | +++ | +++ |
| R64N | 20-134 | + | + |

+ Poor activity (roughly $1 \times 10^{-6}$ $K_f$)
++ Moderate activity (roughly $1 \times 10^{-7}$ $K_f$)
+++ Good (wild-type) activity (roughly $1 \times 10^{-8}$ $K_f$)
++++ Greater than wild-type activity Several variants have been assessed for serum half-life in rats. ActRIIB(20-134)-Fc has a serum half-life of approximately 70 hours. ActRIIB(A24N 20-134)-Fc has a serum half-life of approximately 100-150 hours. The A24N variant has activity in the cell-based assay (above) and in vivo assays (below) that are equivalent to the wild-type molecule. Coupled with the longer half-life, this means that over time an A24N variant will give greater effect per unit of protein than the wild-type molecule. The A24N variant, and any of the other variants tested above, may be combined with the GDF Trap molecules, such as the L79D or L79E variants.

Example 5

GDF-11 and Activin A Binding

Binding of certain ActRIIB-Fc proteins and GDF Traps to ligands was tested in a BiaCore™ assay.

The ActRIIB-Fc variants or wild-type protein were captured onto the system using an anti-hFc antibody. Ligands were injected and flowed over the captured receptor proteins. Results are summarized in the tables, below.

Ligand Binding Specificity IIB Variants.

| Protein | Kon (1/Ms) | Koff (1/s) | KD (M) |
|---|---|---|---|
| | | | GDF11 |
| ActRIIB(20-134)-hFc | 1.34e-6 | 1.13e-4 | 8.42e-11 |
| ActRIIB(A24N 20-134)-hFc | 1.21e-6 | 6.35e-5 | 5.19e-11 |
| ActRIIB(L79D 20-134)-hFc | 6.7e-5 | 4.39e-4 | 6.55e-10 |
| ActRIIB(L79E 20-134)-hFc | 3.8e-5 | 2.74e-4 | 7.16e-10 |
| ActRIIB(R64K 20-134)-hFc | 6.77e-5 | 2.41e-5 | 3.56e-11 |
| | | | GDF8 |
| ActRIIB(20-134)-hFc | 3.69e-5 | 3.45e-5 | 9.35e-11 |
| ActRIIB(A24N 20-134)-hFc | | | |
| ActRIIB(L79D 20-134)-hFc | 3.85e-5 | 8.3e-4 | 2.15e-9 |
| ActRIIB(L79E 20-134)-hFc | 3.74e-5 | 9e-4 | 2.41e-9 |
| ActRIIB(R64K 20-134)-hFc | 2.25e-5 | 4.71e-5 | 2.1e-10 |
| ActRIIB(R64K 20-129)-hFc | 9.74e-4 | 2.09e-4 | 2.15e-9 |
| ActRIIB(P129S, P130R 20-134)-hFc | 1.08e-5 | 1.8e-4 | 1.67e-9 |
| ActRIIB(K74A 20-134)-hFc | 2.8e-5 | 2.03e-5 | 7.18e-11 |
| | | | ActivinA |
| ActRIIB(20-134)-hFc | 5.94e6 | 1.59e-4 | 2.68e-11 |
| ActRIIB(A24N 20-134)-hFc | 3.34e6 | 3.46e-4 | 1.04e-10 |
| ActRIIB(L79D 20-134)-hFc | | | Low binding |
| ActRIIB(L79E 20-134)-hFc | | | Low binding |
| ActRIIB(R64K 20-134)-hFc | 6.82e6 | 3.25e-4 | 4.76e-11 |
| ActRIIB(R64K 20-129)-hFc | 7.46e6 | 6.28e-4 | 8.41e-11 |
| ActRIIB(P129S, P130R 20-134)-hFc | 5.02e6 | 4.17e-4 | 8.31e-11 |

These data confirm the cell based assay data, demonstrating that the A24N variant retains ligand-binding activity that is similar to that of the ActRIIB(20-134)-hFc molecule, and that the L79D or L79E molecule retains myostatin and GDF11 binding but shows markedly decreased (non-quantifiable) binding to Activin A.

Other variants have been generated and tested, as reported in WO2006/012627 (incorporated herein by reference in its entirety) see e.g., pp. 59-60, using ligands coupled to the device and flowing receptor over the coupled ligands. Notably, K74Y, K74F, K74I (and presumably other hydrophobic substitutions at K74, such as K74L), and D80I, cause a decrease in the ratio of Activin A binding to GDF11 binding, relative to the wild-type K74 molecule. A table of data with respect to these variants is reproduced below:

Soluble ActRIIB-Fc Variants Binding to GDF11 and Activin A (BiaCore Assay)

| ActRIIB | ActA | GDF11 |
|---|---|---|
| WT (64A) | KD = 1.8e-7M (+) | KD = 2.6e-7M (+) |
| WT (64R) | na | KD = 8.6e-8M (+++) |
| +15tail | KD ~2.6e-8M (+++) | KD = 1.9e-8M (++++) |
| E37A | * | * |
| R40A | – | – |
| D54A | – | * |
| K55A | ++ | * |
| R56A | * | * |
| K74A | KD = 4.35e-9 M +++++ | KD = 5.3e-9M +++++ |
| K74Y | * | -- |
| K74F | * | -- |
| K74I | * | -- |

-continued

| ActRIIB | ActA | GDF11 |
|---------|------|-------|
| W78A | * | * |
| L79A | + | * |
| D80K | * | * |
| D80R | * | * |
| D80A | * | * |
| D80F | * | * |
| D80G | * | * |
| D80M | * | * |
| D80N | * | * |
| D80I | * | -- |
| F82A | ++ | - |

\* No observed binding
-- <1/5 WT binding
- ~1/2 WT binding
+ WT
++ <2x increased binding
+++ ~5x increased binding
++++ ~10x increased binding
+++++ ~ 40x increased binding

Example 6

ActRIIB-hFc Stimulates Erythropoiesis in Non-Human Primates

ActRIIB(20-134)-hFc (IgG1) was administered once a week for 1 month to male and female cynomolgus monkeys by subcutaneous injection. Forty-eight cynomolgus monkeys (24/sex) were assigned to one of four treatment groups (6 animals/sex/group) and were administered subcutaneous injections of either vehicle or ActRIIB-hFc at 3, 10, or 30 mg/kg once weekly for 4 weeks (total of 5 doses). Parameters evaluated included general clinical pathology (hematology, clinical chemistry, coagulation, and urinalysis). ActRIIB-hFc caused statistically significant elevated mean absolute reticulocyte values by day 15 in treated animals. By day 36, ActRIIB-hFc caused several hematological changes, including elevated mean absolute reticulocyte and red blood cell distribution width values and lower mean corpuscular hemoglobin concentration. All treated groups and both sexes were affected. These effects are consistent with a positive effect of ActRIIB-hFc on the release of immature reticulocytes from the bone marrow. This effect was reversed after drug was washed out of the treated animals (by study day 56). Accordingly, we conclude that ActRIIB-hFc stimulates erythropoiesis.

Example 7

ActRIIB-mFc Promotes Aspects of Erythropoiesis in Mice by Stimulation of Splenic Erythropoietic Activities In this study the effects of the in vivo administration of ActRIIB(20-134)-mFc on the frequency of hematopoietic progenitors in bone marrow and spleen was analyzed. One group of C57BL/6 mice was injected with PBS as a control and a second group of mice administered two doses of ActRIIB-mFc at 10 mg/kg and both groups sacrificed after 8 days. Peripheral blood was used to perform complete blood counts and femurs and spleens were used to perform in vitro clonogenic assays to assess the lymphoid, erythroid and myeloid progenitor cell content in each organ. In the brief time frame of this study, no significant changes were seen in red blood cell, hemoglobin or white blood cell levels in treated mice. In the femurs there was no difference in the nucleated cell numbers or progenitor content between the control and treated groups. In the spleens, the compound treated group experienced a statistically significant increase in the mature erythroid progenitor (CFU-E) colony number per dish, frequency and total progenitor number per spleen. In addition, and increase was seen in the number of myeloid (CFU-GM), immature erythroid (BFU-E) and total progenitor number per spleen.

Animals:
Sixteen C57BL/6 female mice 6-8 weeks of age were used in the study. Eight mice were injected subcutaneously with test compound ActRIIB-mFc at days 1 and 3 at a dose of 10 mg/kg and eight mice were injected subcutaneously with vehicle control, phosphate buffered saline (PBS), at a volume of 100 µL per mouse. All mice were sacrificed 8 days after first injection in accordance with the relevant Animal Care Guidelines. Peripheral blood (PB) samples from individual animals were collected by cardiac puncture and used for complete blood counts and differential (CBC/Diff). Femurs and spleens were harvested from each mouse.

Tests Performed:
CBC/Diff Counts
PB from each mouse was collected via cardiac puncture and placed into the appropriate microtainer tubes. Samples were sent to CLV for analysis on a CellDyn 3500 counter.

Clonogenic Assays
Clonogenic progenitors of the myeloid, erythroid and lymphoid lineages were assessed using the in vitro methylcellulose-based media systems described below.

Mature Erythroid Progenitors:
Clonogenic progenitors of the mature erythroid (CFU-E) lineages were cultured in MethoCult™ 3334, a methylcellulose-based medium containing recombinant human (rh) Erythropoietin (3 U/mL).

Lymphoid Progenitors:
Clonogenic progenitors of the lymphoid (CFU-pre-B) lineage were cultured in MethoCult® 3630, a methylcellulose-based medium containing rh Interleukin 7 (10 ng/mL).

Myeloid and Immature Erythroid Progenitors:
Clonogenic progenitors of the granulocyte-monocyte (CFU-GM), erythroid (BFU-E) and multipotential (CFU-GEMM) lineages were cultured in MethoCult™ 3434, a methylcellulose-based medium containing recombinant murine (rm) Stem Cell Factor (50 ng/mL), rh Interleukin 6 (10 ng/mL), rm Interleukin 3 (10 ng/mL) and rh Erythropoietin (3 U/mL).

Methods:
Mouse femurs and spleens were processed by standard protocols. Briefly, bone marrow was obtained by flushing the femoral cavity with Iscove's Modified Dulbecco's Media containing 2% fetal bovine serum (IMDM 2% FBS) using a 21 gauge needle and 1 cc syringe. Spleen cells were obtained by crushing spleens through a 70 µM filter and rinsing the filter with IMDM 2% FBS. Nucleated cell counts in 3% glacial acetic acid were then performed on the single cells suspensions using a Neubauer counting chamber so that the total cells per organ could be calculated. To remove contaminating red blood cells, total spleen cells were then diluted with 3 times the volume of ammonium chloride lysis buffer and incubated on ice 10 minutes. The cells were then washed and resuspended in IMDM 2% FBS and a second cell count were performed to determine the cell concentration of cells after lysis.

Cell stocks were made and added to each methylcellulose-based media formulation to obtain the optimal plating concentrations for each tissue in each media formulation. Bone marrow cells were plated at $1 \times 10^5$ cells per dish in MethoCult™ 3334 to assess mature erythroid progenitors, $2 \times 10^5$ cells per dish in MethoCult™ 3630 to assess lymphoid progenitors and $3 \times 10^4$ cells per dish in MethoCult™ 3434 to assess immature erythroid and myeloid progenitors. Spleen cells were plated at $4 \times 10^5$ cells per dish in MethoCult™ 3334 to assess mature erythroid progenitors, $4 \times 10^5$ cells per dish in MethoCult™ 3630 to assess lymphoid progenitors and $2 \times 10^5$ cells per dish in MethoCult™ 3434 to assess immature erythroid and myeloid progenitors. Cultures plated in triplicate dishes were incubated at 37° C., 5% CO2 until colony enumeration and evaluation was performed by trained personnel. Mature erythroid progenitors were cultured for 2 days, lymphoid progenitors were cultured for 7 days and mature erythroid and myeloid progenitors were cultured for 12 days.

Analysis:

The mean +/−1 standard deviation was calculated for the triplicate cultures of the clonogenic assays and for the control and treatment groups for all data sets.

Frequency of colony forming cells (CFC) in each tissue was calculated as follows:

Cells plated per dish
Mean CFC scored per dish
Total CFC per femur or spleen was calculated as follows:
Total CFC scored×nucleated cell count per femur or spleen (following RBC lysis)
Number of nucleated cells cultured Standard t-tests were performed to assess if there was a differences in the mean number of cells or hematopoietic progenitors between the PBS control mice and compound treated mice. Due to the potential subjectivity of colony enumeration, a p value of less than 0.01 is deemed significant. Mean values (+/−SD) for each group are shown in the tables below.

TABLE

Hematologic Parameters

| Treatment Group | White Blood Cells ($\times 10^9$/L) | Red Blood Cells ($\times 10^9$/L) | Hemoglobin (g/L) | Hematocrit (L/L) |
|---|---|---|---|---|
| PBS (n = 8) | 9.53 +/− 1.44 | 10.5 +/− 1.1 | 160.9 +/− 13.3 | 0.552 +/− 0.057 |
| ActRIIB-mFc (n = 8) | 9.77 +/− 1.19 | 10.8 +/− 0.3 | 162.1 +/− 4.1 | 0.567 +/− 0.019 |

TABLE

CFC From Femur and Spleen

| Treatment Group | Total CFC per Femur | Total CFC per Spleen | Total CFU-E per Femur | Total CFU-E per Spleen |
|---|---|---|---|---|
| PBS (n = 8) | 88 +/− 10 | 54 +/− 14 | 156 +/− 27 | 131 +/− 71 |
| ActRIIB-mFc (n = 8) | 85 +/− 9 | 79 +/− 6* | 164 +/− 23 | 436 +/− 86* |

*preliminary analysis indicates p < 0.05

Treatment of mice with ActRIIB(20-134)-mFc, in the brief time frame of this study, did not result in significant increases in red blood cell or hemoglobin content. However, the effect on progenitor cell content was notable. In the femurs there was no difference in the nucleated cell numbers or progenitor content between the control and treated groups. In the spleens, the compound treated group experienced a statistically significant increase in the nucleated cell number before red blood cell lysis and in the mature erythroid progenitor (CFU-E) colony number per dish, frequency and total progenitor number per spleen. In addition, an increase was seen in the number of myeloid (CFU-GM), immature erythroid (BFU-E) and total progenitor number per spleen. Accordingly, it is expected that over a longer time course, ActRIIB (20-134)-mFc treatment may result in elevated red blood cell and hemoglobin content.

Example 8

A GDF Trap Increases Red Blood Cell Levels In Vivo

Twelve-week-old male C57BL/6NTac mice were assigned to one of two treatment groups (N=10). Mice were dosed with either vehicle or with a variant ActRIIB polypeptide ("GDF Trap") [ActRIIB(L79D 20-134)-hFc] by subcutaneous injection (SC) at 10 mg/kg twice per week for 4 weeks. At study termination, whole blood was collected by cardiac puncture into EDTA containing tubes and analyzed for cell distribution using an HM2 hematology analyzer (Abaxis, Inc).

| | | Group Designation | | | | |
|---|---|---|---|---|---|---|
| Group | N | Mice | Injection | Dose (mg/kg) | Route | Frequency |
| 1 | 10 | C57BL/6 | PBS | 0 | SC | Twice/week |
| 2 | 10 | C57BL/6 | GDF Trap [ActRIIB (L79D 20-134)-hFc] | 10 | SC | Twice/week |

Treatment with the GDF Trap did not have a statistically significant effect on the number of white blood cells (WBC) compared to the vehicle controls. Red blood cell (RBC) numbers were increased in the treated group relative to the controls (see table below). Both the hemoglobin content (HGB) and hematocrit (HCT) were also increased due to the additional red blood cells. The average width of the red blood cells (RDWc) was higher in the treated animals, indicating an increase in the pool of immature red blood cells. Therefore, treatment with the GDF Trap leads to increases in red blood cells, with no distinguishable effects on white blood cell populations.

| | Hematology Results | | | |
|---|---|---|---|---|
| | RBC $10^{12}$/L | HGB (g/dL) | HCT (%) | RDWc (%) |
| PBS | 10.7 ± 0.1 | 14.8 ± 0.6 | 44.8 ± 0.4 | 17.0 ± 0.1 |
| GDF Trap | 12.4 ± 0.4** | 17.0 ± 0.7* | 48.8 ± 1.8* | 18.4 ± 0.2** |

*= p < 0.05,
**= p < 0.01

Example 9

A GDF Trap is Superior to ActRIIB-Fc for Increasing Red Blood Cell Levels In Vivo Nineteen-week-old male C57BL/6NTac mice were randomly assigned to one of three groups. Mice were dosed with vehicle (10 mM Tris Buffered Saline, TBS), wild-type ActRIIB(20-134)-mFc, or GDF trap ActRIIB(L79D 20-134)-hFc by subcutaneous injection twice per week for three weeks. Blood was collected cheek bleed at baseline and after three weeks of dosing and analyzed for cell distribution using a hematology analyzer (HM2, Abaxis, Inc.)

Treatment with ActRIIB-Fc or the GDF trap did not have a significant effect on white blood cell (WBC) numbers compared to vehicle controls. The red blood cell count (RBC), hematocrit (HCT), and hemoglobin levels were all elevated in GDF Trap treated mice compared to either the controls or the wild-type construct (see table below). Therefore, in a direct comparison, the GDF trap promotes increases in red blood cells to a significantly greater extent than a wild-type ActRIIB-Fc protein. In fact, in this experiment, the wild-type ActRIIB-Fc protein did not cause a statistically significant increase in red blood cells, suggesting that longer or higher dosing would be needed to reveal this effect.

| Hematology Results after three weeks of dosing | | | |
|---|---|---|---|
| | RBC ($10^{12}$/ml) | HCT % | HGB g/dL |
| TBS | 11.06 ± 0.46 | 46.78 ± 1.9 | 15.7 ± 0.7 |
| ActRIIB-mFc | 11.64 ± 0.09 | 49.03 ± 0.3 | 16.5 ± 1.5 |
| GDF Trap | 13.19 ± 0.2** | 53.04 ± 0.8** | 18.4 ± 0.3** |

**= $p < 0.01$

Example 10

Generation of a GDF Trap with Truncated ActRIIB Extracellular Domain

As described in Example 1, a GDF Trap referred to as ActRIIB(L79D 20-134)-hFc was generated by N-terminal fusion of TPA leader to the ActRIIB extracellular domain (residues 20-134 in SEQ ID NO: 1) containing a leucine-to-aspartate substitution (at residue 79 in SEQ ID NO: 1) and C-terminal fusion of human Fc domain with minimal linker (three glycine residues) (FIG. 3). A nucleotide sequence corresponding to this fusion protein is shown in FIG. 4.

A GDF Trap with truncated ActRIIB extracellular domain, referred to as ActRIIB(L79D 25-131)-hFc, was generated by N-terminal fusion of TPA leader to truncated extracellular domain (residues 25-131 in SEQ ID NO: 1) containing a leucine-to-aspartate substitution (at residue 79 in SEQ ID NO: 1) and C-terminal fusion of human Fc domain with minimal linker (three glycine residues) (FIG. 5). A nucleotide sequence corresponding to this fusion protein is shown in FIG. 6.

Example 11

Selective Ligand Binding by GDF Trap with Double-Truncated ActRIIB Extracelluar Domain The affinity of GDF Traps and other ActRIIB-hFc proteins for several ligands was evaluated in vitro with a Biacore™ instrument. Results are summarized in the table below. Kd values were obtained by steady-state affinity fit due to the very rapid association and dissociation of the complex, which prevented accurate determination of $k_{on}$ and $k_{off}$.

Ligand Selectivity of ActRIIB-hFc Variants:

| Fusion Construct | Activin A (Kd e-11) | Activin B (Kd e-11) | GDF11 (Kd e-11) |
|---|---|---|---|
| ActRIIB(L79 20-134)-hFc | 1.6 | 1.2 | 3.6 |
| ActRIIB(L79D 20-134)-hFc | 1350.0 | 78.8 | 12.3 |
| ActRIIB(L79 25-131)-hFc | 1.8 | 1.2 | 3.1 |
| ActRIIB(L79D 25-131)-hFc | 2290.0 | 62.1 | 7.4 |

The GDF Trap with a truncated extracellular domain, ActRIIB(L79D 25-131)-hFc, equaled or surpassed the ligand selectivity displayed by the longer variant, ActRIIB(L79D 20-134)-hFc, with pronounced loss of activin A and activin B binding and nearly full retention of GDF11 binding compared to ActRIIB-hFc counterparts lacking the L79D substitution. Note that truncation alone (without L79D substitution) did not alter selectivity among the ligands displayed here [compare ActRIIB(L79 25-131)-hFc with ActRIIB(L79 20-134)-hFc].

Example 12

Generation of ActRIIB(L79D 25-131)-hFc with Alternative Nucleotide Sequences To generate ActRIIB(L79D 25-131)-hFc, the human ActRIIB extracellular domain with an aspartate substitution at native position 79 (SEQ ID NO: 1) and with N-terminal and C-terminal truncations (residues 25-131 in SEQ ID NO: 1) was fused N-terminally with a TPA leader sequence instead of the native ActRIIB leader and C-terminally with a human Fc domain via a minimal linker (three glycine residues) (FIG. 5). One nucleotide sequence encoding this fusion protein is shown in FIG. 6 (SEQ ID NO: 27), and an alternative nucleotide sequence encoding exactly the same fusion protein is shown in FIG. 9 (SEQ ID NO: 30). This protein was expressed and purified using the methodology described in Example 1.

Example 13

GDF Trap with a Truncated ActRIIB Extracellular Domain Increases Proliferation of Erythroid Progenitors in Mice ActRIIB(L79D 25-131)-hFc was evaluated to determine its effect on proliferation of erythroid progenitors. Male C57BL/6 mice (8 weeks old) were treated with ActRIIB (L79D 25-131)-hFc (10 mg/kg, s.c.; n=6) or vehicle (TBS; n=6) on Days 1 and 4, then euthanized on Day 8 for collection of spleens, tibias, femurs, and blood. Cells of the spleen and bone marrow were isolated, diluted in Iscove's modified Dulbecco's medium containing 5% fetal bovine serum, suspended in specialized methylcellulose-based medium, and cultured for either 2 or 12 days to assess levels of clonogenic progenitors at the colony-forming unit-erythroid (CFU-E) and burst forming unit-erythroid (BFU-E) stages, respectively. Methylcellulose-based medium for BFU-E determination (MethoCult M3434, Stem Cell Technologies) included recombinant murine stem cell factor, interleukin-3, and interleukin-6, which were not present in methylcellulose medium for CFU-E determination (MethoCult M3334, Stem Cell Technologies), while both media contained erythropoietin, among other constituents. For both BFU-E and CFU-E, the number of colonies were determined in duplicate culture plates derived from each tissue sample, and statistical analysis of the results was based on the number of mice per treatment group.

Spleen-derived cultures from mice treated with ActRIIB (L79D 25-131)-hFc had twice the number of CFU-E colonies as did corresponding cultures from control mice (P<0.05), whereas the number of BFU-E colonies did not differ significantly with treatment in vivo. The number of CFU-E or BFU-E colonies from bone marrow cultures also did not differ significantly with treatment. As expected, increased numbers of CFU-E colonies in spleen-derived cultures were accompanied by highly significant (P<0.001) changes in red blood cell level (11.6% increase), hemoglobin concentration (12% increase), and hematocrit level (11.6% increase) at euthanasia in mice treated with ActRIIB(L79D 25-131)-hFc compared to controls. These results indicate that in vivo administration of a GDF Trap with truncated ActRIIB extracellular domain can stimulate proliferation of erythroid progenitors as part of its overall effect to increase red blood cell levels.

Example 14

Figure 11:
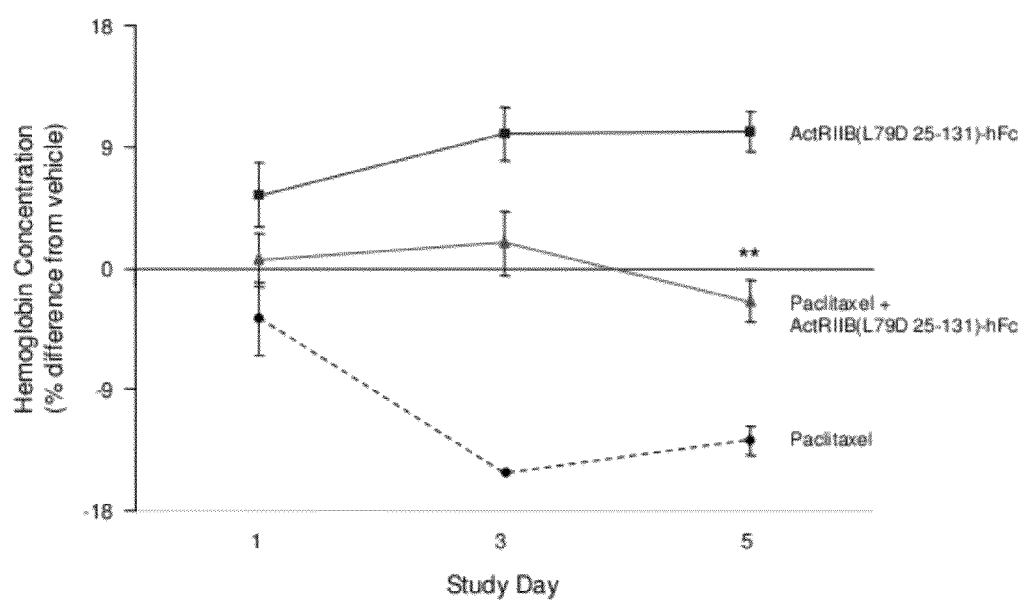
FIG. 11 shows the effect of ActRIIB(L79D 25-131)-hFc on hemoglobin concentration in a mouse model of chemotherapy-induced anemia. Data are means±SEM. **, P<0.01 vs. paclitaxel at the same time point. This GDF Trap offset the anemia induced by paclitaxel treatment.

GDF Trap with a Truncated ActRIIB Extracellular Domain Offsets Chemotherapy-Induced Anemia in Mice Applicants investigated the effect of ActRIIB(L79D 25-131)-hFc on erythropoietic parameters in a mouse model of chemotherapy-induced anemia based on paclitaxel, which inhibits cell division by blocking microtubule polymerization. Male C57BL/6 mice (8 weeks old) were assigned to one of four treatments:
 1) paclitaxel (25 mg/kg, i.p.)
 2) ActRIIB(L79D 25-131)-hFc (10 mg/kg, i.p.)
 3) paclitaxel+ActRIIB(L79D 25-131)-hFc
 4) vehicle (TBS).
Paclitaxel was administered on Day 0, while ActRIIB(L79D 25-131)-hFc or vehicle were administered on Days 0 and 3. Blood samples were collected for CBC analysis from separate cohorts on Days 1, 3, and 5, and results for treatment groups 1-3 (above) were expressed as percent difference from vehicle at a given time point. Attrition due to paclitaxel toxicity was an issue in the paclitaxel-only cohort on Day 3 (where n=1); otherwise, n=3-5 per treatment per time point. Compared to vehicle, paclitaxel alone decreased hemoglobin concentration by nearly 13% at Day 5, whereas addition of ActRIIB(L79D 25-131)-hFc prevented this paclitaxel-induced decline (FIG. 11). Similar effects were observed for hematocrit and RBC levels. In the absence of paclitaxel, ActRIIB(L79D 25-131)-hFc increased hemoglobin concentration by 10% compared to vehicle on Days 3 and 5 (FIG. 11). Thus, a GDF Trap with truncated ActRIIB extracellular domain can increase levels of red blood cells sufficiently to offset chemotherapy-induced anemia.

Example 15

Figure 12:
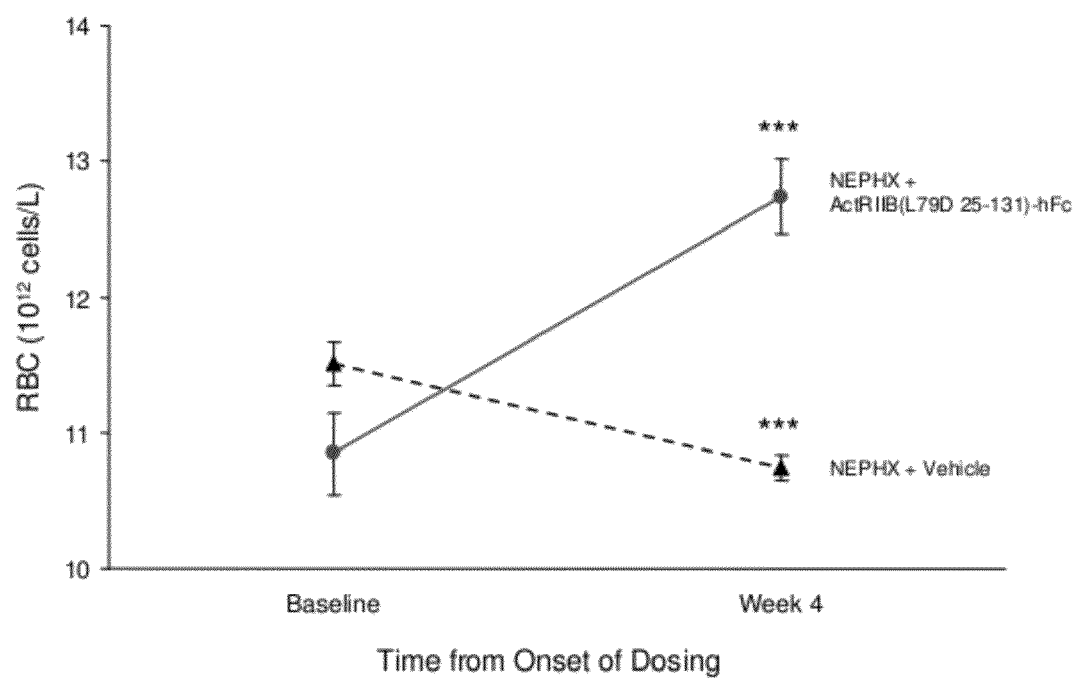
FIG. 12 shows the effect of ActRIIB(L79D 25-131)-hFc on red blood cell (RBC) levels in a unilaterally nephrectomized (NEPHX) mouse model of chronic kidney disease. Data are means±SEM. ***, P<0.001 vs. baseline. This GDF Trap reversed the nephrectomy-induced anemia observed in control mice.
Figure 13:
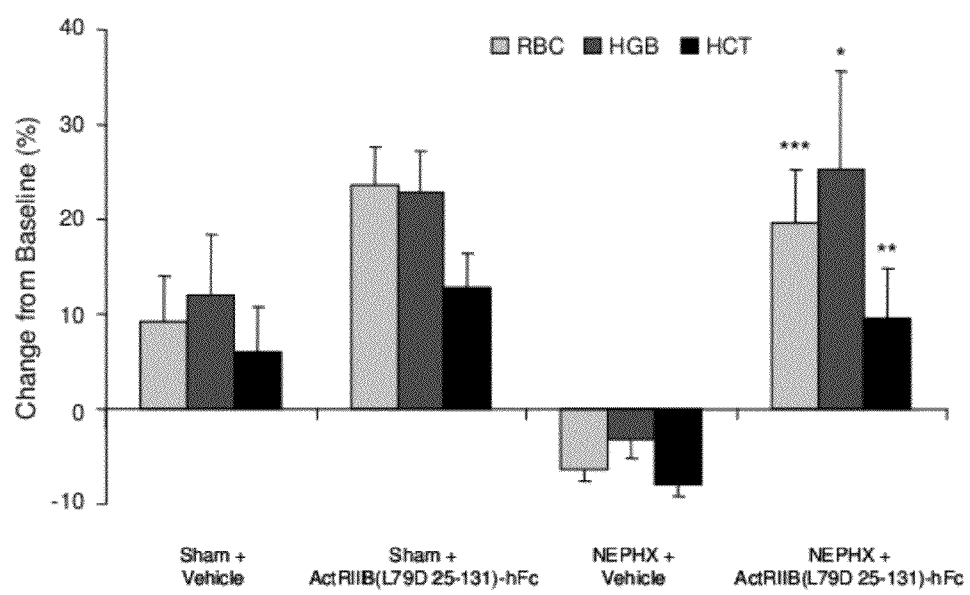
FIG. 13 shows the effect of ActRIIB(L79D 25-131)-hFc on red blood cell (RBC), hemoglobin (HGB), and hematocrit (HCT) levels in a unilaterally nephrectomized (NEPHX) mouse model of chronic kidney disease. Data are mean changes from baseline over 4 weeks (±SEM). *, P<0.05; , P<0.01; *, P<0.001 vs. NEPHX controls. This GDF Trap prevented the nephrectomy-associated decline in these erythrocytic parameters, increasing each by a magnitude similar to that in kidney-intact (sham) mice.

GDF Trap with a Truncated ActRIIB Extracellular Domain Reverses Nephrectomy-Induced Anemia in Mice Applicants investigated the effect of ActRIIB(L79D 25-131)-hFc on anemia in a nephrectomized mouse model of chronic kidney disease. Male C57BL/6 mice (11 weeks old) underwent either a sham operation or a unilateral nephrectomy to reduce the capacity for erythropoietin production. Mice were allowed a week for postsurgical recovery and then treated twice-weekly with ActRIIB(L79D 25-131)-hFc (10 mg/kg, i.p.; n=15 per condition) or vehicle (TBS; n=15 per condition) for a total of 4 weeks. Blood samples were collected before the onset of dosing and after 4 weeks of treatment. Whereas vehicle-treated nephrectomized mice displayed a significant decline in red blood cell number over the 4-week treatment period, treatment with ActRIIB(L79D 25-131)-hFc not only prevented the decline but increased red blood cell levels 17% (P<0.001) above baseline (FIG. 12), despite reduced renal capacity for erythropoietin production. In nephrectomized mice, ActRIIB(L79D 25-131)-hFc also generated significant increases from baseline in hemoglobin concentration and hematocrit level and, notably, stimulated each of these erythropoietic parameters to approximately the same extent under nephrectomized conditions as under sham-operated conditions (FIG. 13). Thus, a GDF Trap with truncated ActRIIB extracellular domain can increase red blood cell levels sufficiently to reverse anemia in a model of chronic kidney disease.

Example 16

GDF Trap with a Truncated ActRIIB Extracellular Domain Improves Recovery from Anemia Induced by Blood Loss in Rats Applicants investigated the effect of ActRIIB(L79D 25-131)-hFc on erythropoietic parameters in a rat model of anemia induced by acute blood loss (acute post-hemorrhagic anemia). Male Sprague-Dawley rats (approximately 300 g) received a chronic jugular catheter at the vendor (Harlan). On Day–1, 20% of total blood volume was withdrawn from each rat over a 5-minute period via the catheter under isoflurane anesthesia. The volume of blood removed was based on a value for total blood volume calculated according to the following relationship derived by Lee and co-workers (J Nucl Med 25:72-76, 1985) for rats with body weight greater than 120 g:

Total blood volume (ml)=0.062×body weight (g)+ 0.0012

An equal volume of phosphate-buffered saline was replaced via the catheter at the time of blood removal. Rats were treated with ActRIIB(L79D 25-131)-hFc (10 mg/kg, s.c.; n=5) or vehicle (TBS; n=5) on Days 0 and 3. Blood samples for CBC analysis were removed via the catheter on Days–1 (baseline), 0, 2, 4, and 6.

Figure 14:
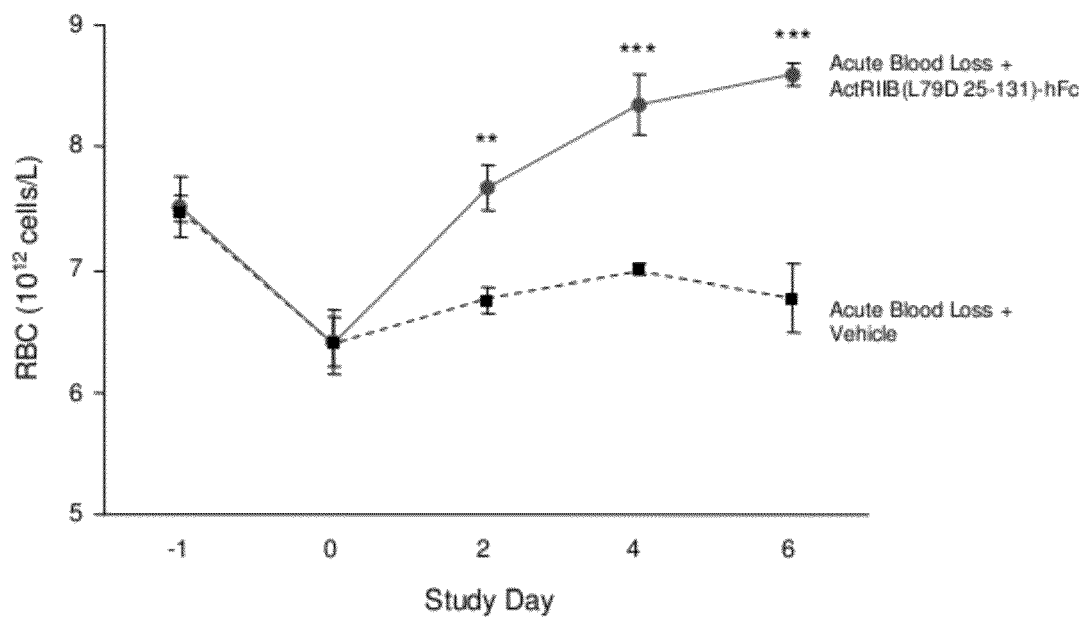
FIG. 14 shows the effect of ActRIIB(L79D 25-131)-hFc on red blood cell (RBC) levels in a rat model of anemia induced by acute blood loss. Blood removal occurred on Day−1, with dosing on Days 0 and 3. Data are means±SEM. , P<0.01; *, P<0.001 vs. vehicle at same time point. This GDF Trap improved the rate and extent of recovery from blood-loss-induced anemia.

Control rats responded to 20% blood loss with a drop of nearly 15% in red-blood-cell levels by Day 0. These levels remained significantly lower than baseline on Days 2 and 4, and had not recovered fully by Day 6 (FIG. 14). Although rats treated with ActRIIB(L79D 25-131)-hFc showed a nearly identical drop in red-blood-cell levels after 20% blood loss, these rats then displayed a complete recovery in such levels by Day 2, followed by further elevation on Days 4 and 6, which represents a highly significant improvement over control levels at the corresponding time points (FIG. 14). Similar results were obtained for hemoglobin concentration. These findings demonstrate that a GDF Trap with truncated ActRIIB extracellular domain can produce a faster recovery of red blood cell levels from anemia caused by acute hemorrhage.

Example 17

Figure 15:
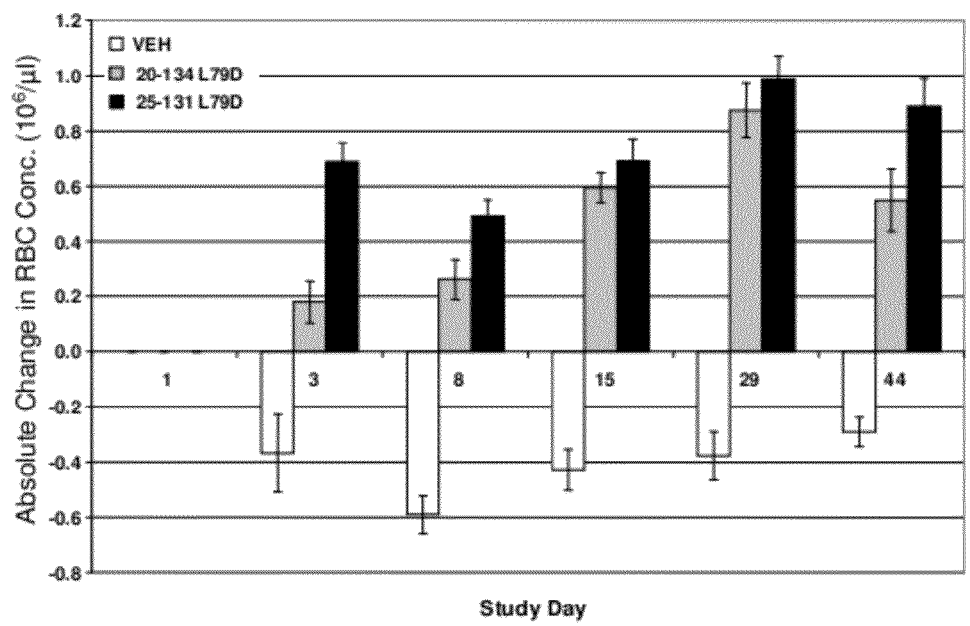
FIG. 15 shows the effect of treatment with ActRIIB(L79D 20-134)-hFc (gray) or ActRIIB(L79D 25-131)-hFc (black) on the absolute change in red blood cell concentration from baseline in cynomolgus monkey. VEH=vehicle. Data are means±SEM. n=4-8 per group.
Figure 16:
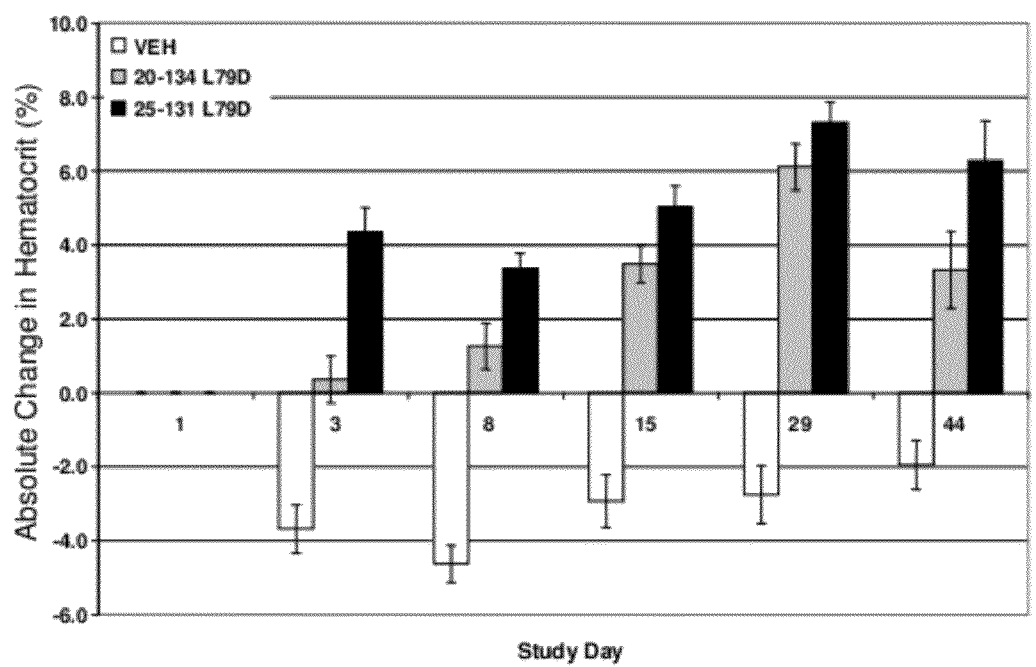
FIG. 16 shows the effect of treatment with ActRIIB(L79D 20-134)-hFc (gray) or ActRIIB(L79D 25-131)-hFc (black) on the absolute change in hematocrit from baseline in cynomolgus monkey. VEH=vehicle. Data are means±SEM. n=4-8 per group.
Figure 17:
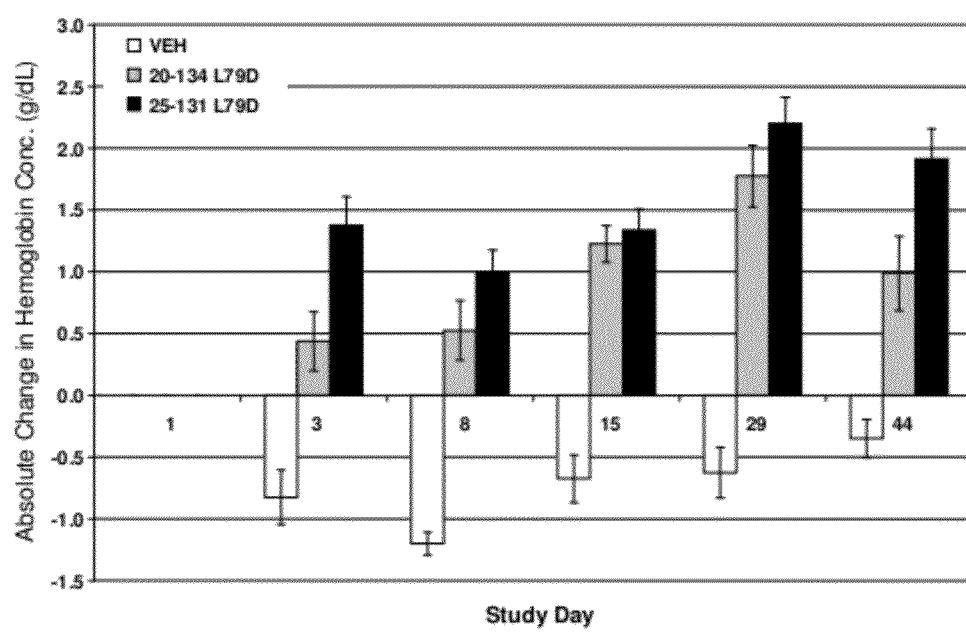
FIG. 17 shows the effect of treatment with ActRIIB(L79D 20-134)-hFc (gray) or ActRIIB(L79D 25-131)-hFc (black) on the absolute change in hemoglobin concentration from baseline in cynomolgus monkey. VEH=vehicle. Data are means±SEM. n=4-8 per group.
Figure 18:
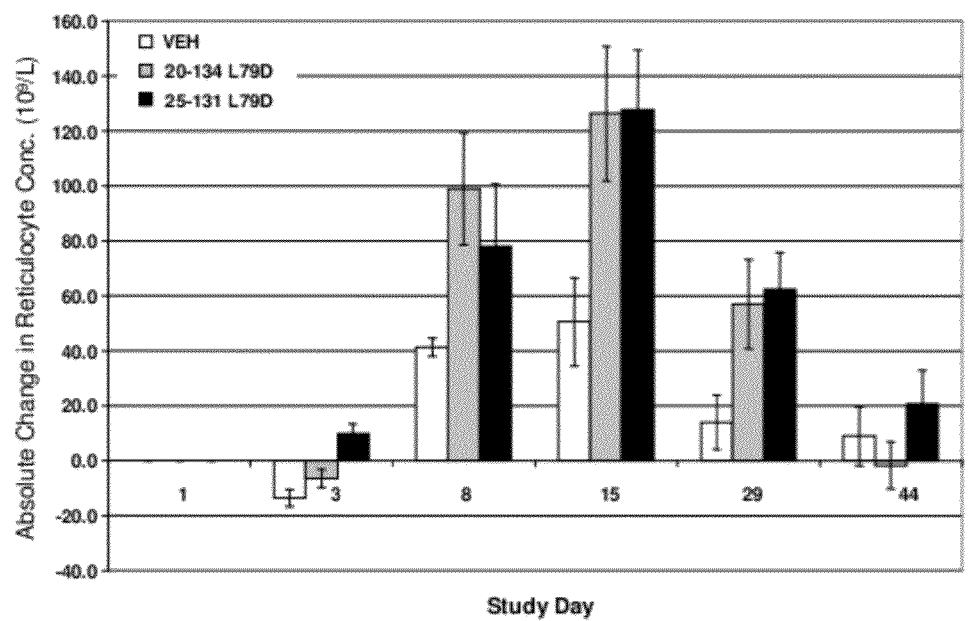
FIG. 18 shows the effect of treatment with ActRIIB(L79D 20-134)-hFc (gray) or ActRIIB(L79D 25-131)-hFc (black) on the absolute change in circulating reticulocyte concentration from baseline in cynomolgus monkey. VEH=vehicle. Data are means±SEM. n=4-8 per group.

GDF Trap with Truncated ActRIIB Extracelluar Domain Increases Levels of Red Blood Cells in Non-Human Primates Two GDF Traps, ActRIIB(L79D 20-134)-hFc and ActRIIB (L79D 25-131)-hFc, were evaluated for their ability to stimulate red blood cell production in cynomolgus monkey. Monkeys were treated subcutaneously with GDF Trap (10 mg/kg; n=4 males/4 females), or vehicle (n=2 males/2 females) on Days 1 and 8. Blood samples were collected on Days 1 (pretreatment baseline), 3, 8, 15, 29, and 44, and were analyzed for red blood cell levels (FIG. 15), hematocrit (FIG. 16), hemoglobin levels (FIG. 17), and reticulocyte levels (FIG. 18). Vehicle-treated monkeys exhibited decreased levels of red blood cells, hematocrit, and hemoglobin at all post-treatment time points, an expected effect of repeated blood sampling. In contrast, treatment with ActRIIB(L79D 20-134)-hFc or ActRIIB(L79D 25-131)-hFc increased these parameters by the first post-treatment time point (Day 3) and maintained them at substantially elevated levels for the duration of the study (FIGS. 15-17). Importantly, reticulocyte levels in monkeys treated with ActRIIB(L79D 20-134)-hFc or ActRIIB(L79D 25-131)-hFc were substantially increased at Days 8, 15, and 29 compared to vehicle (FIG. 18). This result demonstrates that GDF Trap treatment increased production of red blood cell precursors, resulting in elevated red blood cell levels.

Taken together, these data demonstrate that truncated GDF Traps, as well as a full-length variants, can be used as selective antagonists of GDF11 and potentially related ligands to increase red blood cell formation in vivo.

Example 18

GDF Trap Derived from ActRIIB5

Others have reported an alternate, soluble form of ActRIIB (designated ActRIIB5), in which exon 4, including the ActRIIB transmembrane domain, has been replaced by a different C-terminal sequence (WO2007/053775).

The sequence of native human ActRIIB5 without its leader is as follows:

```
                                            (SEQ ID NO: 36)
GRGEAETRECIYYNANWELERTNQSGLERCEGEQDKRLHCYASWRNS

SGTIELVKKGCWLDDFNCYDRQECVATEENPQVYFCCCEGNFCNERF

THLPEAGGPEGPWASTTIPSGGPEATAAAGDQGSGALWLCLEGPAHE
```

An leucine-to-aspartate substitution, or other acidic substitutions, may be performed at native position 79 (underlined and highlighted) as described to construct the variant ActRIIB5(L79D), which has the following sequence:

```
                                            (SEQ ID NO: 37)
GRGEAETRECIYYNANWELERTNQSGLERCEGEQDKRLHCYASWRNS

SGTIELVKKGCWDDDFNCYDRQECVATEENPQVYFCCCEGNFCNERF

THLPEAGGPEGPWASTTIPSGGPEATAAAGDQGSGALWLCLEGPAHE
```

This variant may be connected to human Fc with a TGGG linker to generate a human ActRIIB5(L79D)-hFc fusion protein with the following sequence:

```
                                            (SEQ ID NO: 38)
GRGEAETRECIYYNANWELERTNQSGLERCEGEQDKRLHCYASWRNS

SGTIELVKKGCWDDDFNCYDRQECVATEENPQVYFCCCEGNFCNERF

THLPEAGGPEGPWASTTIPSGGPEATAAAGDQGSGALWLCLEGPAHE

TGGGTHTCPPCPAPELLGGPSVFLFPPKPKDTLMISRTPEVTCVVV

DVSHEDPEVKFNWYVDGVEVHNAKTKPREEQYNSTYRVVSVLTVLHQ

DWLNGKEYKCKVSNKALPAPIEKTISKAKGQPREPQVYTLPPSREEM

TKNQVSLTCLVKGFYPSDIAVEWESNGQPENNYKTTPPVLDSDGSFF

LYSKLTVDKSRWQQGNVFSCSVMHEALHNHYTQKSLSLSPGK
```

This construct may be expressed in CHO cells.

Example 19

Effects in Mice of Combined Treatment with EPO and a GDF Trap with a Truncated ActRIIB Extracellular Domain EPO induces formation of red blood cells by increasing the proliferation of erythroid precursors, whereas GDF Traps could potentially affect formation of red blood cells in ways that complement or enhance EPO's effects. Therefore, Applicants investigated the effect of combined treatment with EPO and ActRIIB(L79D 25-131)-hFc on erythropoietic parameters. Male C57BL/6 mice (9 weeks old) were given a single i.p. injection of recombinant human EPO alone (epoetin alfa, 1800 units/kg), ActRIIB(L79D 25-131)-hFc alone (10 mg/kg), both EPO and ActRIIB(L79D 25-131)-hFc, or vehicle (Tris-buffered saline). Mice were euthanized 72 h after dosing for collection of blood, spleens, and femurs.

Spleens and femurs were processed to obtain erythroid precursor cells for flow cytometric analysis. After removal, the spleen was minced in Iscove's modified Dulbecco's medium containing 5% fetal bovine serum and mechanically dissociated by pushing through a 70-μm cell strainer with the plunger from a sterile 1-mL syringe. Femurs were cleaned of any residual muscle or connective tissue and ends were trimmed to permit collection of marrow by flushing the remaining shaft with Iscove's modified Dulbecco's medium containing 5% fetal bovine serum through a 21-gauge needle connected to a 3-mL syringe. Cell suspensions were centrifuged (2000 rpm for 10 min) and the cell pellets resuspended in PBS containing 5% fetal bovine serum. Cells ($10^6$) from each tissue were incubated with anti-mouse IgG to block nonspecific binding, then incubated with fluorescently labeled antibodies against mouse cell-surface markers CD71 (transferrin receptor) and Ter119 (an antigen associated with cell-surface glycophorin A), washed, and analyzed by flow cytometry. Dead cells in the samples were excluded from analysis by counterstaining with propidium iodide. Erythroid differentiation in spleen or bone marrow was assessed by the degree of CD71 labeling, which decreases over the course of differentiation, and Ter119 labeling, which is increased during terminal erythroid differentiation beginning with the proerythroblast stage (Socolovsky et al., 2001, Blood 98:3261-3273; Ying et al., 2006, Blood 108:123-133). Thus, flow cytometry was used to determine the number of proerythroblasts ($CD71^{high}Ter119^{low}$), basophilic erythroblasts ($CD71^{high}Ter119^{high}$), polychromatophilic+orthochromatophilic erythroblasts ($CD71^{med}Ter119^{high}$), and late orthochromatophilic erythroblasts+reticulocytes (CD71$^{low}$Ter119$^{high}$), as described.

Figure 19:
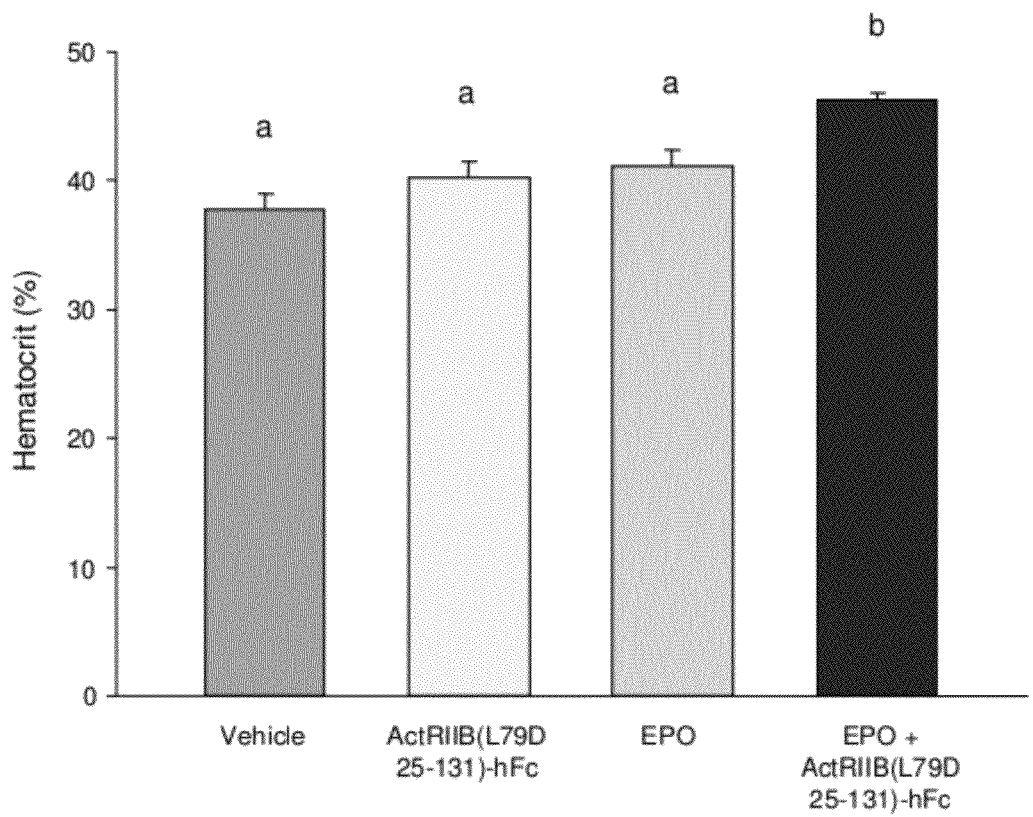
FIG. 19 shows the effect of combined treatment with erythropoietin (EPO) and ActRIIB(L79D 25-131)-hFc for 72 hours on hematocrit in mice. Data are means±SEM (n=4 per group), and means that are significantly different from each other (p<0.05, unpaired t-test) are designated by different letters. Combined treatment increased hematocrit by 23% compared to vehicle, a synergistic increase greater than the sum of the separate effects of EPO and ActRIIB(L79D 25-131)-hFc.

Combined treatment with EPO and ActRIIB(L79D 25-131)-hFc led to a surprisingly vigorous increase in red blood cells. In the 72-h time frame of this experiment, neither EPO nor ActRIIB(L79D 25-131)-hFc alone increased hematocrit significantly compared to vehicle, whereas combined treatment with the two agents led to a nearly 25% increase in hematocrit that was unexpectedly synergistic, i.e., greater than the sum of their separate effects (FIG. 19). Synergy of this type is generally considered evidence that individual agents are acting through different cellular mechanisms. Similar results were also observed for hemoglobin concentrations (FIG. 20) and red blood cell concentrations (FIG. 21), each of which was also increased synergistically by combined treatment.

Analysis of erythroid precursor levels revealed a more complex pattern. In the mouse, the spleen is considered the primary organ responsible for inducible ("stress") erythropoiesis. Flow cytometric analysis of splenic tissue at 72 h revealed that EPO markedly altered the erythropoietic precursor profile compared to vehicle, increasing the number of basophilic erythroblasts by more than 170% at the expense of late precursors (late orthochromatophilic erythroblasts+reticulocytes), which decreased by more than one third (FIG. 22). Importantly, combined treatment increased basophilic erythroblasts significantly compared to vehicle, but to a lesser extent than EPO alone, while supporting undiminished maturation of late-stage precursors (FIG. 22). Thus, combined treatment with EPO and ActRIIB(L79D 25-131)-hFc increased erythropoiesis through a balanced enhancement of precursor proliferation and maturation. In contrast to spleen, the precursor cell profile in bone marrow after combined treatment did not differ appreciably from that after EPO alone. Applicants predict from the splenic precursor profile that combined treatment would lead to increased reticulocyte levels and would be accompanied by sustained elevation of mature red blood cell levels, if the experiment were extended beyond 72 h.

Taken together, these findings demonstrate that a GDF Trap with a truncated ActRIIB extracellular domain can be administered in combination with EPO to synergistically increase red blood cell formation in vivo. Acting through a complementary but undefined mechanism, a GDF trap can moderate the strong proliferative effect of an EPO receptor activator alone and still permit target levels of red blood cells to be attained with lower doses of an EPO receptor activator, thereby avoiding potential adverse effects or other problems associated with higher levels of EPO receptor activation.

Example 20

GDF Trap with a Truncated ActRIIB Extracellular Domain Increases RBC Levels in a Mouse Model of Myelodysplastic Syndrome Myelodysplastic syndromes (MDS) are diverse disorders of bone marrow failure characterized clinically by peripheral cytopenia, refractory anemia, and risk of progression to acute myeloid leukemia. Transfusion of RBCs is a key maintenance therapy in MDS to alleviate fatigue, improve quality of life, and prolong survival; however, regular transfusions typically result in iron overload in these patients, with adverse effects on morbidity and mortality which can lead to use of remedies such as iron chelation therapy (Dreyfus, 2008, Blood Rev 22 Suppl 2:S29-34; Jabbour et al., 2009, Oncologist 14:489-496). Although recombinant erythropoietin (EPO) and its derivatives are an alternative therapeutic approach in a small percentage of MDS patients (Estey, 2003, Curr Opin Hematol 10:60-67), recent studies suggest that this class of agents is associated with an increased risk of morbidity and mortality at some doses due to thromboembolic events and tumor growth (Krapf et al., 2009, Clin J Am Soc Nephrol 4:470-480; Glaspy, 2009, Annu Rev Med 60:181-192). Thus, there is the need for an alternative MDS therapy that would increase RBC levels without the iron overload that accompanies chronic transfusions or the risks inherent in exogenous EPO and its derivatives.

Therefore, Applicants investigated the effect of ActRIIB (L79D 25-131)-hFc on RBC levels in a transgenic mouse model that recapitulates the key features of MDS, including transformation to acute leukemia (Lin et al., 2005, Blood 106:287-295; Beachy et al., 2010, Hematol Oncol Clin North Am 24:361-375). Beginning at three months of age, male and female NUP98-HOXD13 mice were treated twice-weekly with ActRIIB(L79D 25-131)-hFc (10 mg/kg, s.c.) or vehicle (TBS). Wildtype littermates were dosed with ActRIIB(L79D 25-131)-hFc or vehicle and served as controls. Blood samples were collected before the onset of dosing and at monthly intervals thereafter to perform CBC measurements.

Several differences were noted at baseline between NUP98-HOXD13 mice and wildtype controls. Specifically, male NUP98-HOXD13 mice displayed significantly decreased RBC concentrations (−8.8%, p<0.05) and hematocrit (−8.4%, p<0.05) compared to wildtype mice, and female NUP98-HOXD13 mice showed similar trends. Results after three months of dosing (mean±SD) are shown in the following table.

| NUP98-HOXD13 Mice | | RBC Conc. ($10^{12}$ cells/L) | Hemoglobin Conc. (g/dL) | Hematocrit (%) |
|---|---|---|---|---|
| Male | Vehicle (n = 6) | 6.56 ± 0.51 | 10.68 ± 0.68 | 31.83 ± 2.13 |
| | ActRIIB(L79D 25-131)-hFc (n = 8) | 8.65 ± 0.54*** | 13.54 ± 0.91*** | 39.20 ± 2.82*** |
| Female | Vehicle (n = 5) | 6.38 ± 1.61 | 10.30 ± 2.58 | 31.96 ± 8.73 |
| | ActRIIB(L79D 25-131)-hFc (n = 6) | 8.52 ± 0.70* | 13.52 ± 0.56* | 42.23 ± 2.53† |

***p < 0.001 vs. male + vehicle
*p < 0.05 vs. female + vehicle
†p = 0.056 vs. female + vehicle Compared to vehicle, treatment with ActRIIB(L79D 25-131)-hFc for three months increased RBC concentrations and hemoglobin concentrations significantly (by approximately 30%) in both male and female NUP98-HOXD13 mice. Hematocrit also increased significantly in these male mice and increased with a trend toward significance in the female mice. Thus, a GDF Trap with truncated ActRIIB extracellular domain can increase RBC levels significantly in a murine model of MDS. Whereas transfusions are inherently a source of exogenous iron, a GDF Trap raises RBC levels by promoting use of endogenous iron stores via erythropoiesis, thereby avoiding iron overloading and its negative consequences. In addition, as noted in Example 19, a GDF Trap acts through a different (albeit complementary) cellular mechanism than that used by EPO receptor activators to stimulate erythropoiesis, and thereby circumvents potential adverse effects associated with EPO receptor activation.

INCORPORATION BY REFERENCE

All publications and patents mentioned herein are hereby incorporated by reference in their entirety as if each individual publication or patent was specifically and individually indicated to be incorporated by reference.

While specific embodiments of the subject matter have been discussed, the above specification is illustrative and not restrictive. Many variations will become apparent to those skilled in the art upon review of this specification and the claims below. The full scope of the invention should be determined by reference to the claims, along with their full scope of equivalents, and the specification, along with such variations.

We claim:

1. A method for increasing red blood cell levels or treating anemia in a patient, the method comprising administering to a patient in need thereof:
   (a) an erythropoietin receptor activator, wherein the activator is an agent that i) increases proliferation of immature erythroblasts, ii) increases differentiation of immature erythroblasts, and/or iii) decreases apoptosis in erythroid progenitor cells; and
   (b) a polypeptide comprising an amino acid sequence that is at least 95% identical to the sequence of amino acids 29-109 of SEQ ID NO: 1, and wherein the polypeptide comprises an acidic amino acid at the position corresponding to position 79 of SEQ ID NO: 1, wherein the polypeptide binds to GDF11; and
   wherein the erythropoietin receptor activator and the polypeptide are administered in an effective amount.

2. The method of claim 1, wherein the administered amount of erythropoietin receptor activator is by itself ineffective in increasing red blood cell levels in the patient even though combined treatment is effective.

3. The method of claim 1, wherein the administered amount of polypeptide is by itself ineffective in increasing red blood cell levels in the patient even though combined treatment is effective.

4. The method of claim 1, wherein the erythropoietin receptor activator is an erythropoiesis-stimulating agent.

5. The method of claim 4, wherein the erythropoiesis-stimulating agent is an EPO-based derivative selected from a group consisting of:
   a. epoetin alfa
   b. epoetin beta (NeoRecormon)
   c. epoetin delta (Dynepo)
   d. epoetin omega
   e. darbepoetin alfa (Aranesp)
   f. methoxy-polyethylene-glycol epoetin beta (Micera), and
   g. synthetic erythropoiesis protein (SEP).

6. The method of claim 1, wherein the erythropoietin receptor activator is an erythropoietin receptor agonist chosen from a group consisting of:
   a. a peptidic erythropoietin mimetic
   b. an erythropoietin receptor extended-duration limited agonist
   c. a fusion protein comprising an erythropoietin mimetic domain and an Fc domain
   d. an agonistic antibody targeting the erythropoietin receptor and
   e. a multimeric peptidic erythropoietin mimetic.

7. The method of claim 1, wherein the patient has anemia associated with a kidney disorder.

8. The method of claim 7, wherein the patient has anemia associated with chronic kidney disease.

9. The method of claim 1, wherein the patient has anemia associated with a chemotherapy treatment.

10. The method of claim 9, wherein the chemotherapy treatment is a taxane.

11. The method of claim 1, wherein the patient has anemia as a consequence of blood loss.

12. The method of claim 1, wherein the polypeptide comprises an amino acid sequence corresponding to amino acids 29-109 of SEQ ID NO:1.

13. A method for increasing red blood cell levels or treating myelodysplastic syndrome (MDS) in a patient, the method comprising administering to a patient in need thereof:
    (a) a therapeutic agent for treating MDS; and
    (b) a polypeptide comprising an amino acid sequence that is at least 95% identical to the sequence of amino acids 29-109 of SEQ ID NO: 1, and wherein the polypeptide comprises an acidic amino acid at the position corresponding to position 79 of SEQ ID NO: 1, wherein the polypeptide binds to GDF11;
    wherein the therapeutic agent for treating MDS and the polypeptide are administered in an effective amount.

14. The method of claim 13, wherein the therapeutic agent for treating MDS is selected from the group consisting of: thalidomide, lenalidomide, azacitadine, decitabine, an erythropoietin receptor activator, erythropoietins, deferoxamine, antithymocyte globulin, filgrastrim (G-CSF) and an erythropoietin signaling pathway agonist.

15. The method of claim 14, wherein the therapeutic agent for treating MDS is an erythropoietin receptor activator that i) increases proliferation of immature erythroblasts, ii) increases differentiation of immature erythroblasts, and/or iii) decreases apoptosis in erythroid progenitor cells.

16. The method of claim 15, wherein the administered amount of erythropoietin receptor activator is by itself ineffective in increasing red blood cell levels even thought combined treatment is effective.

17. The method of claim 13, wherein the administered amount of polypeptide is by itself ineffective in increasing red blood cell levels in the patient even though combined treatment is effective.

18. The method of claim 15, wherein the erythropoietin receptor activator is an erythropoiesis-stimulating agent and wherein the erythropoiesis-stimulating agent is selected from a group consisting of:
    a. epoetin alfa
    b. epoetin beta (NeoRecormon)
    c. epoetin delta (Dynepo)
    d. epoetin omega
    e. darbepoetin alfa (Aranesp)
    f. methoxy-polyethylene-glycol epoetin beta (Micera), and
    g. synthetic erythropoiesis protein (SEP).

19. The method of claim 15, wherein the erythropoietin receptor activator is an erythropoietin receptor agonist, wherein the erythropoietin receptor agonist is chosen from a group consisting of:
    a. a peptidic erythropoietin mimetic
    b. an erythropoietin receptor extended-duration limited agonist
    c. a fusion protein comprising an erythropoietin mimetic domain and an Fc domain
    d. an agonistic antibody targeting the erythropoietin receptor, and
    e. a multimeric peptidic erythropoietin mimetic.

20. The method of claim 13, wherein the polypeptide comprises an amino acid sequence corresponding to amino acids 29-109 of SEQ ID NO:1.

* * * * *

```
SEQUENCE LISTING

<160> NUMBER OF SEQ ID NOS: 44

<210> SEQ ID NO 1
<211> LENGTH: 512
<212> TYPE: PRT
<213> ORGANISM: Homo sapiens

<400> SEQUENCE: 1

Met Thr Ala Pro Trp Val Ala Leu Ala Leu Leu Trp Gly Ser Leu Trp
1               5                   10                  15

Pro Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Arg
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Val Thr Tyr Glu Pro
        115                 120                 125

Pro Pro Thr Ala Pro Thr Leu Leu Thr Val Leu Ala Tyr Ser Leu Leu
    130                 135                 140

Pro Ile Gly Gly Leu Ser Leu Ile Val Leu Leu Ala Phe Trp Met Tyr
145                 150                 155                 160

Arg His Arg Lys Pro Pro Tyr Gly His Val Asp Ile His Glu Asp Pro
                165                 170                 175

Gly Pro Pro Pro Ser Pro Leu Val Gly Leu Lys Pro Leu Gln Leu
            180                 185                 190

Leu Glu Ile Lys Ala Arg Gly Arg Phe Gly Cys Val Trp Lys Ala Gln
        195                 200                 205

Leu Met Asn Asp Phe Val Ala Val Lys Ile Phe Pro Leu Gln Asp Lys
    210                 215                 220

Gln Ser Trp Gln Ser Glu Arg Glu Ile Phe Ser Thr Pro Gly Met Lys
225                 230                 235                 240

His Glu Asn Leu Leu Gln Phe Ile Ala Ala Glu Lys Arg Gly Ser Asn
                245                 250                 255
```

Leu Glu Val Glu Leu Trp Leu Ile Thr Ala Phe His Asp Lys Gly Ser
            260                 265                 270

Leu Thr Asp Tyr Leu Lys Gly Asn Ile Ile Thr Trp Asn Glu Leu Cys
            275                 280                 285

His Val Ala Glu Thr Met Ser Arg Gly Leu Ser Tyr Leu His Glu Asp
            290                 295                 300

Val Pro Trp Cys Arg Gly Glu Gly His Lys Pro Ser Ile Ala His Arg
305                 310                 315                 320

Asp Phe Lys Ser Lys Asn Val Leu Leu Lys Ser Asp Leu Thr Ala Val
            325                 330                 335

Leu Ala Asp Phe Gly Leu Ala Val Arg Phe Glu Pro Gly Lys Pro Pro
            340                 345                 350

Gly Asp Thr His Gly Gln Val Gly Thr Arg Arg Tyr Met Ala Pro Glu
            355                 360                 365

Val Leu Glu Gly Ala Ile Asn Phe Gln Arg Asp Ala Phe Leu Arg Ile
            370                 375                 380

Asp Met Tyr Ala Met Gly Leu Val Leu Trp Glu Leu Val Ser Arg Cys
385                 390                 395                 400

Lys Ala Ala Asp Gly Pro Val Asp Glu Tyr Met Leu Pro Phe Glu Glu
            405                 410                 415

Glu Ile Gly Gln His Pro Ser Leu Glu Glu Leu Gln Glu Val Val Val
            420                 425                 430

His Lys Lys Met Arg Pro Thr Ile Lys Asp His Trp Leu Lys His Pro
            435                 440                 445

Gly Leu Ala Gln Leu Cys Val Thr Ile Glu Glu Cys Trp Asp His Asp
            450                 455                 460

Ala Glu Ala Arg Leu Ser Ala Gly Cys Val Glu Glu Arg Val Ser Leu
465                 470                 475                 480

Ile Arg Arg Ser Val Asn Gly Thr Thr Ser Asp Cys Leu Val Ser Leu
            485                 490                 495

Val Thr Ser Val Thr Asn Val Asp Leu Pro Pro Lys Glu Ser Ser Ile
            500                 505                 510

<210> SEQ ID NO 2
<211> LENGTH: 115
<212> TYPE: PRT
<213> ORGANISM: Homo sapiens

<400> SEQUENCE: 2

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
            35                  40                  45

Gly Thr Ile Glu Leu Val Lys Lys Gly Cys Trp Leu Asp Asp Phe Asn
            50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
            85                  90                  95

Leu Pro Glu Ala Gly Gly Pro Glu Val Thr Tyr Glu Pro Pro Pro Thr
            100                 105                 110

Ala Pro Thr
            115

<210> SEQ ID NO 3
<211> LENGTH: 100
<212> TYPE: PRT
<213> ORGANISM: Homo sapiens

<400> SEQUENCE: 3

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Leu Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala
            100

<210> SEQ ID NO 4
<211> LENGTH: 1539
<212> TYPE: DNA
<213> ORGANISM: Homo sapiens

<400> SEQUENCE: 4
atgacggcgc cctgggtggc cctcgccctc ctctggggat cgctgtgtgcc cggctctggg      60 cgtggggagg ctgagacacg ggagtgcatc tactacaacg ccaactggga gctggagcgc     120
accaaccaga gcggcctgga gcgctgcgaa ggcgagcagg acaagcggct gcactgctac     180
gcctcctggg ccaacagctc tggcaccatc gagctcgtga agaagggctg ctggctagat     240
gacttcaact gctacgatag gcaggagtgt gtggccactg aggagaaccc ccaggtgtac     300
ttctgctgct gtgaaggcaa cttctgcaac gagcgcttca ctcatttgcc agaggctggg     360
ggcccggaag tcacgtacga gccacccccg acagccccca ccctgctcac ggtgctggcc     420
tactcactgc tgcccatcgg gggccttttcc ctcatcgtcc tgctggcctt ttggatgtac     480
cggcatcgca agccccccta cggtcatgtg acatccatg aggaccctgg gcctccacca     540
ccatcccctc tggtgggcct gaagccactg cagctgctgg agatcaaggc tcggggcgc     600 tttggctgtg tctggaaggc ccagctcatg aatgactttg tagctgtcaa gatcttccca     660
ctccaggaca agcagtcgtg gcagagtgaa cgggagatct tcagcacacc tggcatgaag     720
cacgagaacc tgctacagtt cattgctgcc gagaagcgag gctccaacct cgaagtagag     780
ctgtggctca tcacgccctt ccatgacaag ggctccctca cggattacct caagggggaac     840 atcatcacat ggaacgaact gtgtcatgta gcagagacga tgtcacgagg cctctcatac     900
ctgcatgagg atgtgccctg gtgccgtggc gagggccaca gccgtctat tgcccacagg     960 gactttaaaa gtaagaatgt attgctgaag agcgacctca cagccgtgct ggctgacttt    1020
ggcttggctc ttcgatttga gcagggaaa cctccagggg acacccacgg acaggtaggc    1080
acgagacggt acatggctcc tgaggtgctc gagggagcca tcaacttcca gagagatgcc    1140
ttcctgcgca ttgacatgta tgccatgggg ttggtgctgt gggagcttgt gtctcgctgc    1200
aaggctgcag acggacccgt ggatgagtac atgctgccct ttgaggaaga gattggccag    1260

-continued

```
cacccttcgt tggaggagct gcaggaggtg gtggtgcaca agaagatgag gcccaccatt    1320
aaagatcact ggttgaaaca cccgggcctg cccagcttt gtgtgaccat cgaggagtgc     1380
tgggaccatg atgcagaggc tcgcttgtcc gcgggctgtg tggaggagcg ggtgtccctg    1440
attcggaggt cggtcaacgg cactacctcg gactgtctcg tttccctggt gacctctgtc    1500
accaatgtgg acctgccccc taaagagtca agcatctaa                           1539
```

<210> SEQ ID NO 5
<211> LENGTH: 345
<212> TYPE: DNA
<213> ORGANISM: Homo sapiens

<400> SEQUENCE: 5

```
gggcgtgggg aggctgagac acgggagtgc atctactaca acgccaactg ggagctggag      60
cgcaccaacc agagcggcct ggagcgctgc gaaggcgagc aggacaagcg gctgcactgc    120
tacgcctcct gggccaacag ctctggcacc atcgagctcg tgaagaaggg ctgctggcta    180
gatgacttca actgctacga taggcaggag tgtgtggcca ctgaggagaa ccccccaggtg    240 tacttctgct gctgtgaagg caacttctgc aacgagcgct tcactcattt gccagaggct    300
gggggcccgg aagtcacgta cgagccaccc ccgacagccc ccacc                    345
```

<210> SEQ ID NO 6
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (43)..(43)
<223> OTHER INFORMATION: Asp or Ala
<220> FEATURE:
<221> NAME/KEY: MOD_RES
<222> LOCATION: (100)..(100)
<223> OTHER INFORMATION: Lys or Ala
<220> FEATURE:
<221> NAME/KEY: MOD_RES
<222> LOCATION: (212)..(212)
<223> OTHER INFORMATION: Asn or Ala

<400> SEQUENCE: 6

```
Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Xaa Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Xaa Val Ser Asn Lys Ala Leu Pro Val Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Glu Glu Met Thr Lys Asn Gln Val Ser Leu Thr
    130                 135                 140
```

```
Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Pro Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Xaa His Tyr Thr Gln Lys Ser Leu Ser Leu Ser Pro Gly
    210                 215                 220

Lys
225

<210> SEQ ID NO 7
<211> LENGTH: 343
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Asp Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110

Ala Pro Thr Gly Gly Gly Thr His Thr Cys Pro Pro Cys Pro Ala Pro
        115                 120                 125

Glu Leu Leu Gly Gly Pro Ser Val Phe Leu Phe Pro Pro Lys Pro Lys
    130                 135                 140

Asp Thr Leu Met Ile Ser Arg Thr Pro Glu Val Thr Cys Val Val Val
145                 150                 155                 160

Asp Val Ser His Glu Asp Pro Glu Val Lys Phe Asn Trp Tyr Val Asp
                165                 170                 175

Gly Val Glu Val His Asn Ala Lys Thr Lys Pro Arg Glu Glu Gln Tyr
            180                 185                 190

Asn Ser Thr Tyr Arg Val Val Ser Val Leu Thr Val Leu His Gln Asp
        195                 200                 205

Trp Leu Asn Gly Lys Glu Tyr Lys Cys Lys Val Ser Asn Lys Ala Leu
    210                 215                 220

Pro Val Pro Ile Glu Lys Thr Ile Ser Lys Ala Lys Gly Gln Pro Arg
225                 230                 235                 240

Glu Pro Gln Val Tyr Thr Leu Pro Pro Ser Arg Glu Glu Met Thr Lys
                245                 250                 255

Asn Gln Val Ser Leu Thr Cys Leu Val Lys Gly Phe Tyr Pro Ser Asp
            260                 265                 270
```

```
Ile Ala Val Glu Trp Glu Ser Asn Gly Gln Pro Glu Asn Asn Tyr Lys
        275                 280                 285

Thr Thr Pro Pro Val Leu Asp Ser Asp Gly Ser Phe Phe Leu Tyr Ser
        290                 295                 300

Lys Leu Thr Val Asp Lys Ser Arg Trp Gln Gln Gly Asn Val Phe Ser
305                 310                 315                 320

Cys Ser Val Met His Glu Ala Leu His Asn His Tyr Thr Gln Lys Ser
                325                 330                 335

Leu Ser Leu Ser Pro Gly Lys
            340

<210> SEQ ID NO 8
<211> LENGTH: 21
<212> TYPE: PRT
<213> ORGANISM: Apis mellifera

<400> SEQUENCE: 8

Met Lys Phe Leu Val Asn Val Ala Leu Val Phe Met Val Val Tyr Ile
1               5                   10                  15

Ser Tyr Ile Tyr Ala
            20

<210> SEQ ID NO 9
<211> LENGTH: 22
<212> TYPE: PRT
<213> ORGANISM: Unknown
<220> FEATURE:
<223> OTHER INFORMATION: Description of Unknown: Tissue Plasminogen
      Activator

<400> SEQUENCE: 9

Met Asp Ala Met Lys Arg Gly Leu Cys Cys Val Leu Leu Leu Cys Gly
1               5                   10                  15

Ala Val Phe Val Ser Pro
            20

<210> SEQ ID NO 10
<211> LENGTH: 19
<212> TYPE: PRT
<213> ORGANISM: Unknown
<220> FEATURE:
<223> OTHER INFORMATION: Description of Unknown: Native peptide

<400> SEQUENCE: 10

Met Thr Ala Pro Trp Val Ala Leu Ala Leu Leu Trp Gly Ser Leu Cys
1               5                   10                  15

Ala Gly Ser

<210> SEQ ID NO 11
<211> LENGTH: 368
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met Asp Ala Met Lys Arg Gly Leu Cys Cys Val Leu Leu Leu Cys Gly
1               5                   10                  15

Ala Val Phe Val Ser Pro Gly Ala Ser Gly Arg Gly Glu Ala Glu Thr
            20                  25                  30

Arg Glu Cys Ile Tyr Tyr Asn Ala Asn Trp Glu Leu Glu Arg Thr Asn
        35                  40                  45
```

Gln Ser Gly Leu Glu Arg Cys Glu Gly Glu Gln Asp Lys Arg Leu His
    50                  55                  60

Cys Tyr Ala Ser Trp Arg Asn Ser Ser Gly Thr Ile Glu Leu Val Lys
 65                  70                  75                  80

Lys Gly Cys Trp Asp Asp Phe Asn Cys Tyr Asp Arg Gln Glu Cys
                85                  90                  95

Val Ala Thr Glu Glu Asn Pro Gln Val Tyr Phe Cys Cys Glu Gly
            100                 105                 110

Asn Phe Cys Asn Glu Arg Phe Thr His Leu Pro Glu Ala Gly Gly Pro
            115                 120                 125

Glu Val Thr Tyr Glu Pro Pro Thr Ala Pro Thr Gly Gly Gly Thr
            130                 135                 140

His Thr Cys Pro Pro Cys Pro Ala Pro Glu Leu Leu Gly Gly Pro Ser
145                 150                 155                 160

Val Phe Leu Phe Pro Pro Lys Pro Lys Asp Thr Leu Met Ile Ser Arg
                165                 170                 175

Thr Pro Glu Val Thr Cys Val Val Asp Val Ser His Glu Asp Pro
            180                 185                 190

Glu Val Lys Phe Asn Trp Tyr Val Asp Gly Val Glu Val His Asn Ala
            195                 200                 205

Lys Thr Lys Pro Arg Glu Glu Gln Tyr Asn Ser Thr Tyr Arg Val Val
210                 215                 220

Ser Val Leu Thr Val Leu His Gln Asp Trp Leu Asn Gly Lys Glu Tyr
225                 230                 235                 240

Lys Cys Lys Val Ser Asn Lys Ala Leu Pro Val Pro Ile Glu Lys Thr
                245                 250                 255

Ile Ser Lys Ala Lys Gly Gln Pro Arg Glu Pro Gln Val Tyr Thr Leu
            260                 265                 270

Pro Pro Ser Arg Glu Glu Met Thr Lys Asn Gln Val Ser Leu Thr Cys
            275                 280                 285

Leu Val Lys Gly Phe Tyr Pro Ser Asp Ile Ala Val Glu Trp Glu Ser
290                 295                 300

Asn Gly Gln Pro Glu Asn Asn Tyr Lys Thr Thr Pro Pro Val Leu Asp
305                 310                 315                 320

Ser Asp Gly Ser Phe Phe Leu Tyr Ser Lys Leu Thr Val Asp Lys Ser
                325                 330                 335

Arg Trp Gln Gln Gly Asn Val Phe Ser Cys Ser Val Met His Glu Ala
            340                 345                 350

Leu His Asn His Tyr Thr Gln Lys Ser Leu Ser Leu Ser Pro Gly Lys
            355                 360                 365

<210> SEQ ID NO 12
<211> LENGTH: 1107
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
atggatgcaa tgaagagagg gctctgctgt gtgctgctgc tgtgtggagc agtcttcgtt    60
tcgcccggcg cctctgggcg tggggaggct gagacacggg agtgcatcta ctacaacgcc   120
aactgggagc tggagcgcac caaccagagc ggcctggagc gctgcgaagg cgagcaggac   180
aagcggctga ctgctacgc ctcctggcgc aacagctctg gcaccatcga gctcgtgaag   240

```
aagggctgct gggacgatga cttcaactgc tacgataggc aggagtgtgt ggccactgag    300
gagaaccccc aggtgtactt ctgctgctgt gaaggcaact tctgcaacga gcgcttcact    360
catttgccag aggctggggg cccggaagtc acgtacgagc accccccgac agcccccacc    420
ggtggtggaa ctcacacatg cccaccgtgc ccagcacctg aactcctggg gggaccgtca    480
gtcttcctct tccccccaaa acccaaggac accctcatga tctcccggac ccctgaggtc    540
acatgcgtgg tggtggacgt gagccacgaa gaccctgagg tcaagttcaa ctggtacgtg    600
gacggcgtgg aggtgcataa tgccaagaca aagccgcggg aggagcagta caacagcacg    660
taccgtgtgg tcagcgtcct caccgtcctg caccaggact ggctgaatgg caaggagtac    720
aagtgcaagg tctccaacaa agccctccca gtccccatcg agaaaaccat ctccaaagcc    780
aaagggcagc cccgagaacc acaggtgtac accctgcccc catcccggga ggagatgacc    840
aagaaccagg tcagcctgac ctgcctggtc aaaggcttct atcccagcga catcgccgtg    900
gagtgggaga gcaatgggca gccggagaac aactacaaga ccacgcctcc cgtgctggac    960
tccgacggct ccttcttcct ctatagcaag ctcaccgtgg acaagagcag gtggcagcag   1020
gggaacgtct tctcatgctc cgtgatgcat gaggctctgc acaaccacta cacgcagaag   1080
agcctctccc tgtctccggg taaatga                                       1107
```

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Thr Gly Gly Gly Gly
1               5

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ser Gly Gly Gly Gly
1               5

<210> SEQ ID NO 15
<211> LENGTH: 116
<212> TYPE: PRT
<213> ORGANISM: Homo sapiens

<400> SEQUENCE: 15

Ile Leu Gly Arg Ser Glu Thr Gln Glu Cys Leu Phe Phe Asn Ala Asn
1               5                   10                  15

Trp Glu Lys Asp Arg Thr Asn Gln Thr Gly Val Glu Pro Cys Tyr Gly
            20                  25                  30

Asp Lys Asp Lys Arg Arg His Cys Phe Ala Thr Trp Lys Asn Ile Ser
        35                  40                  45

Gly Ser Ile Glu Ile Val Lys Gln Gly Cys Trp Leu Asp Asp Ile Asn
    50                  55                  60

Cys Tyr Asp Arg Thr Asp Cys Val Glu Lys Lys Asp Ser Pro Glu Val
65                  70                  75                  80

Tyr Phe Cys Cys Cys Glu Gly Asn Met Cys Asn Glu Lys Phe Ser Tyr
                85                  90                  95

Phe Pro Glu Met Glu Val Thr Gln Pro Thr Ser Asn Pro Val Thr Pro
            100                 105                 110

Lys Pro Pro Thr
        115

<210> SEQ ID NO 16
<211> LENGTH: 150
<212> TYPE: PRT
<213> ORGANISM: Rattus sp.

<400> SEQUENCE: 16

Met Thr Ala Pro Trp Ala Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Pro
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Pro Gly Gly Pro Glu Val Thr Tyr Glu Pro
            115                 120                 125

Pro Pro Thr Ala Pro Thr Leu Leu Thr Val Leu Ala Tyr Ser Leu Leu
        130                 135                 140

Pro Ile Gly Gly Leu Ser
145                 150

<210> SEQ ID NO 17
<211> LENGTH: 150
<212> TYPE: PRT
<213> ORGANISM: Sus sp.

<400> SEQUENCE: 17

Met Thr Ala Pro Trp Ala Ala Leu Ala Leu Leu Trp Gly Ser Leu Cys
1               5                   10                  15

Val Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Arg
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Val Thr Tyr Glu Pro
            115                 120                 125

Pro Pro Thr Ala Pro Thr Leu Leu Thr Val Leu Ala Tyr Ser Leu Leu
130                 135                 140

Pro Ile Gly Gly Leu Ser
145                 150

<210> SEQ ID NO 18
<211> LENGTH: 150
<212> TYPE: PRT
<213> ORGANISM: Mus sp.

<400> SEQUENCE: 18

Met Thr Ala Pro Trp Ala Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
                20                  25                  30

Asn Ala Asn Trp Glu Leu Glu Arg Thr Asn Gln Ser Gly Leu Glu Arg
            35                  40                  45

Cys Glu Gly Glu Gln Asp Lys Arg Leu His Cys Tyr Ala Ser Trp Arg
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Pro Gly Gly Pro Glu Val Thr Tyr Glu Pro
        115                 120                 125

Pro Pro Thr Ala Pro Thr Leu Leu Thr Val Leu Ala Tyr Ser Leu Leu
130                 135                 140

Pro Ile Gly Gly Leu Ser
145                 150

<210> SEQ ID NO 19
<211> LENGTH: 150
<212> TYPE: PRT
<213> ORGANISM: Homo sapiens

<400> SEQUENCE: 19

Met Thr Ala Pro Trp Val Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
                20                  25                  30

Asn Ala Asn Trp Glu Leu Glu Arg Thr Asn Gln Ser Gly Leu Glu Arg
            35                  40                  45

Cys Glu Gly Glu Gln Asp Lys Arg Leu His Cys Tyr Ala Ser Trp Arg
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Val Thr Tyr Glu Pro
        115                 120                 125

Pro Pro Thr Ala Pro Thr Leu Leu Thr Val Leu Ala Tyr Ser Leu Leu
130                 135                 140

Pro Ile Gly Gly Leu Ser

<210> SEQ ID NO 20
<211> LENGTH: 150
<212> TYPE: PRT
<213> ORGANISM: Bos sp.

<400> SEQUENCE: 20

Met Thr Ala Pro Trp Ala Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Arg Asp Lys Arg Leu His Cys Tyr Ala Ser Trp Arg
50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Pro Glu Val Thr Tyr Glu Pro
        115                 120                 125

Pro Pro Thr Ala Pro Thr Leu Leu Thr Val Leu Ala Tyr Ser Leu Leu
    130                 135                 140

Pro Val Gly Gly Leu Ser
145                 150

<210> SEQ ID NO 21
<211> LENGTH: 150
<212> TYPE: PRT
<213> ORGANISM: Xenopus sp.

<400> SEQUENCE: 21

Met Gly Ala Ser Val Ala Leu Thr Phe Leu Leu Leu Ala Thr Phe
1               5                   10                  15

Arg Ala Gly Ser Gly His Asp Glu Val Glu Thr Arg Glu Cys Ile Tyr
            20                  25                  30

Tyr Asn Ala Asn Trp Glu Leu Glu Lys Thr Asn Gln Ser Gly Val Glu
        35                  40                  45

Arg Leu Val Glu Gly Lys Lys Asp Lys Arg Leu His Cys Tyr Ala Ser
50                  55                  60

Trp Arg Asn Asn Ser Gly Phe Ile Glu Leu Val Lys Lys Gly Cys Trp
65                  70                  75                  80

Leu Asp Asp Phe Asn Cys Tyr Asp Arg Gln Glu Cys Ile Ala Lys Glu
                85                  90                  95

Glu Asn Pro Gln Val Phe Phe Cys Cys Cys Glu Gly Asn Tyr Cys Asn
            100                 105                 110

Lys Lys Phe Thr His Leu Pro Glu Val Glu Thr Phe Asp Pro Lys Pro
        115                 120                 125

Gln Pro Ser Ala Ser Val Leu Asn Ile Leu Ile Tyr Ser Leu Leu Pro
    130                 135                 140

Ile Val Gly Leu Ser Met
145                 150

<210> SEQ ID NO 22

```
<211> LENGTH: 150
<212> TYPE: PRT
<213> ORGANISM: Homo sapiens

<400> SEQUENCE: 22

Met Gly Ala Ala Lys Leu Ala Phe Ala Val Phe Leu Ile Ser Cys
1               5                   10                  15

Ser Ser Gly Ala Ile Leu Gly Arg Ser Glu Thr Gln Glu Cys Leu Phe
            20                  25                  30

Phe Asn Ala Asn Trp Glu Lys Asp Arg Thr Asn Gln Thr Gly Val Glu
                35                  40                  45

Pro Cys Tyr Gly Asp Lys Asp Lys Arg Arg His Cys Phe Ala Thr Trp
    50                  55                  60

Lys Asn Ile Ser Gly Ser Ile Glu Ile Val Lys Gln Gly Cys Trp Leu
65                  70                  75                  80

Asp Asp Ile Asn Cys Tyr Asp Arg Thr Asp Cys Val Glu Lys Lys Asp
                85                  90                  95

Ser Pro Glu Val Tyr Phe Cys Cys Cys Glu Gly Asn Met Cys Asn Glu
            100                 105                 110

Lys Phe Ser Tyr Phe Pro Glu Met Glu Val Thr Gln Pro Thr Ser Asn
        115                 120                 125

Pro Val Thr Pro Lys Pro Pro Tyr Tyr Asn Ile Leu Leu Tyr Ser Leu
    130                 135                 140

Val Pro Leu Met Leu Ile
145                 150

<210> SEQ ID NO 23
<211> LENGTH: 154
<212> TYPE: PRT
<213> ORGANISM: Artificial Sequence
<220> FEATURE:
<223> OTHER INFORMATION: Description of Artificial Sequence: Synthetic
      consensus polypeptide
<220> FEATURE:
<221> NAME/KEY: MOD_RES
<222> LOCATION: (8)..(8)
<223> OTHER INFORMATION: Thr or Ala
<220> FEATURE:
<221> NAME/KEY: MOD_RES
<222> LOCATION: (121)..(121)
<223> OTHER INFORMATION: Pro, Ala, Val or Met

<400> SEQUENCE: 23

Met Thr Ala Pro Trp Ala Ala Xaa Leu Ala Leu Leu Trp Gly Ser Leu
1               5                   10                  15

Cys Ala Gly Ser Gly Arg Gly Glu Ala Glu Thr Arg Glu Cys Ile Tyr
            20                  25                  30

Tyr Asn Ala Asn Trp Glu Leu Glu Arg Thr Asn Gln Ser Gly Leu Glu
                35                  40                  45

Arg Leu Cys Glu Gly Gly Gln Asp Lys Arg Leu His Cys Tyr Ala Ser
    50                  55                  60

Trp Arg Asn Ser Ser Gly Thr Leu Glu Leu Val Lys Lys Gly Cys Trp
65                  70                  75                  80

Leu Asp Asp Phe Asn Cys Tyr Asp Arg Gln Glu Cys Val Ala Thr Glu
                85                  90                  95

Glu Asn Pro Gln Val Tyr Phe Cys Cys Cys Gly Asn Phe Cys Asn
            100                 105                 110

Glu Arg Phe Thr His Leu Pro Glu Xaa Gly Gly Pro Glu Val Thr Tyr
        115                 120                 125

Glu Pro Lys Pro Pro Thr Ala Pro Thr Leu Leu Thr Val Leu Ala Tyr
```

```
                130                 135                 140
Ser Leu Leu Pro Ile Gly Gly Leu Ser Met
145                 150
```

```
<210> SEQ ID NO 24
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 24

His His His His His His
1               5
```

```
<210> SEQ ID NO 25
<211> LENGTH: 1107
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
atggatgcaa tgaagagagg gctctgctgt gtgctgctgc tgtgtggagc agtcttcgtt      60
tcgcccggcg cctctgggcg tggggaggct gagacacggg agtgcatcta ctacaacgcc     120
aactgggagc tggagcgcac caaccagagc ggcctggagc gctgcgaagg cgagcaggac     180
aagcggctgc actgctacgc ctcctggcgc aacagctctg gcaccatcga gctcgtgaag     240
aagggctgct gggatgatga cttcaactgc tacgataggc aggagtgtgt ggccactgag     300
gagaaccccc aggtgtactt ctgctgctgt gaaggcaact tctgcaacga gcgcttcact     360
catttgccag aggctggggg cccggaagtc acgtacgagc acccccgac agccccacc      420 ggtggtggaa ctcacacatg cccaccgtgc ccagcacctg aactcctggg gggaccgtca     480
gtcttcctct tccccccaaa acccaaggac accctcatga tctcccggac ccctgaggtc     540
acatgcgtgt ggtggacgt gagccacgaa gaccctgagg tcaagttcaa ctggtacgtg      600
gacggcgtgg aggtgcataa tgccaagaca aagccgcggg aggagcagta caacagcacg     660
taccgtgtgg tcagcgtcct caccgtcctg caccaggact ggctgaatgg caaggagtac     720
aagtgcaagg tctccaacaa agccctccca gcccccatcg agaaaaccat ctccaaagcc     780
aaagggcagc cccgagaacc acaggtgtac accctgcccc catcccggga ggagatgacc     840
aagaaccagg tcagcctgac ctgcctggtc aaaggcttct atcccagcga catcgccgtg     900
gagtgggaga gcaatgggca gccggagaac aactacaaga ccacgcctcc cgtgctggac     960
tccgacggct ccttcttcct ctatagcaag ctcaccgtgg acaagagcag gtggcagcag    1020
gggaacgtct tctcatgctc cgtgatgcat gaggctctgc acaaccacta cacgcagaag    1080
agcctctccc tgtccccggg taaatga                                       1107
```

```
<210> SEQ ID NO 26
<211> LENGTH: 360
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Met Asp Ala Met Lys Arg Gly Leu Cys Cys Val Leu Leu Leu Cys Gly
```

```
                1               5                   10                  15
Ala Val Phe Val Ser Pro Gly Ala Ala Glu Thr Arg Glu Cys Ile Tyr
                        20                  25                  30

Tyr Asn Ala Asn Trp Glu Leu Glu Arg Thr Asn Gln Ser Gly Leu Glu
                    35                  40                  45

Arg Cys Glu Gly Glu Gln Asp Lys Arg Leu His Cys Tyr Ala Ser Trp
        50                  55                  60

Arg Asn Ser Ser Gly Thr Ile Glu Leu Val Lys Lys Gly Cys Trp Asp
65                      70                  75                      80

Asp Asp Phe Asn Cys Tyr Asp Arg Gln Glu Cys Val Ala Thr Glu Glu
                        85                  90                  95

Asn Pro Gln Val Tyr Phe Cys Cys Cys Glu Gly Asn Phe Cys Asn Glu
                    100                 105                 110

Arg Phe Thr His Leu Pro Glu Ala Gly Gly Pro Glu Val Thr Tyr Glu
                115                 120                 125

Pro Pro Pro Thr Gly Gly Gly Thr His Thr Cys Pro Pro Cys Pro Ala
            130                 135                 140

Pro Glu Leu Leu Gly Gly Pro Ser Val Phe Leu Phe Pro Pro Lys Pro
145                 150                 155                 160

Lys Asp Thr Leu Met Ile Ser Arg Thr Pro Glu Val Thr Cys Val Val
                    165                 170                 175

Val Asp Val Ser His Glu Asp Pro Glu Val Lys Phe Asn Trp Tyr Val
                180                 185                 190

Asp Gly Val Glu Val His Asn Ala Lys Thr Lys Pro Arg Glu Glu Gln
            195                 200                 205

Tyr Asn Ser Thr Tyr Arg Val Val Ser Val Leu Thr Val Leu His Gln
        210                 215                 220

Asp Trp Leu Asn Gly Lys Glu Tyr Lys Cys Lys Val Ser Asn Lys Ala
225                 230                 235                 240

Leu Pro Ala Pro Ile Glu Lys Thr Ile Ser Lys Ala Lys Gly Gln Pro
                    245                 250                 255

Arg Glu Pro Gln Val Tyr Thr Leu Pro Pro Ser Arg Glu Glu Met Thr
                260                 265                 270

Lys Asn Gln Val Ser Leu Thr Cys Leu Val Lys Gly Phe Tyr Pro Ser
            275                 280                 285

Asp Ile Ala Val Glu Trp Glu Ser Asn Gly Gln Pro Glu Asn Asn Tyr
        290                 295                 300

Lys Thr Thr Pro Pro Val Leu Asp Ser Asp Gly Ser Phe Phe Leu Tyr
305                 310                 315                 320

Ser Lys Leu Thr Val Asp Lys Ser Arg Trp Gln Gln Gly Asn Val Phe
                    325                 330                 335

Ser Cys Ser Val Met His Glu Ala Leu His Asn His Tyr Thr Gln Lys
                340                 345                 350

Ser Leu Ser Leu Ser Pro Gly Lys
            355                 360

<210> SEQ ID NO 27
<211> LENGTH: 1083
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (76)..(396)
```

-continued

```
<400> SEQUENCE: 27
atggatgcaa tgaagagagg gctctgctgt gtgctgctgc tgtgtggagc agtcttcgtt        60
tcgcccggcg ccgct gag aca cgg gag tgc atc tac tac aac gcc aac tgg       111
              Glu Thr Arg Glu Cys Ile Tyr Tyr Asn Ala Asn Trp
                1               5                   10 gag ctg gag cgc acc aac cag agc ggc ctg gag cgc tgc gaa ggc gag        159
Glu Leu Glu Arg Thr Asn Gln Ser Gly Leu Glu Arg Cys Glu Gly Glu
         15                  20                  25 cag gac aag cgg ctg cac tgc tac gcc tcc tgg cgc aac agc tct ggc        207
Gln Asp Lys Arg Leu His Cys Tyr Ala Ser Trp Arg Asn Ser Ser Gly
     30                  35                  40 acc atc gag ctc gtg aag aag ggc tgc tgg gac gat gac ttc aac tgc        255
Thr Ile Glu Leu Val Lys Lys Gly Cys Trp Asp Asp Asp Phe Asn Cys
45                  50                  55                  60 tac gat agg cag gag tgt gtg gcc act gag gag aac ccc cag gtg tac        303
Tyr Asp Arg Gln Glu Cys Val Ala Thr Glu Glu Asn Pro Gln Val Tyr
                 65                  70                  75 ttc tgc tgc tgt gaa ggc aac ttc tgc aac gag cgc ttc act cat ttg        351
Phe Cys Cys Cys Glu Gly Asn Phe Cys Asn Glu Arg Phe Thr His Leu
             80                  85                  90 cca gag gct ggg ggc ccg gaa gtc acg tac gag cca ccc ccg aca            396
Pro Glu Ala Gly Gly Pro Glu Val Thr Tyr Glu Pro Pro Pro Thr
         95                 100                 105 ggtggtggaa ctcacacatg cccaccgtgc ccagcacctg aactcctggg gggaccgtca      456
gtcttcctct tccccccaaa acccaaggac accctcatga tctcccggac ccctgaggtc      516
acatgcgtgg tggtggacgt gagccacgaa gaccctgagg tcaagttcaa ctggtacgtg      576
gacggcgtgg aggtgcataa tgccaagaca aagccgcggg aggagcagta caacagcacg      636
taccgtgtgg tcagcgtcct caccgtcctg caccaggact ggctgaatgg caaggagtac      696
aagtgcaagg tctccaacaa agccctccca gcccccatcg agaaaaccat ctccaaagcc      756
aaagggcagc cccgagaacc acaggtgtac accctgcccc catcccggga ggagatgacc      816
aagaaccagg tcagcctgac ctgcctggtc aaaggcttct atcccagcga catcgccgtg      876
gagtgggaga gcaatgggca gccggagaac aactacaaga ccacgcctcc cgtgctggac      936
tccgacggct ccttcttcct ctatagcaag ctcaccgtgg acaagagcag gtggcagcag      996
gggaacgtct tctcatgctc cgtgatgcat gaggctctgc acaaccacta cacgcagaag     1056
agcctctccc tgtccccggg taaatga                                         1083

<210> SEQ ID NO 28
<211> LENGTH: 335
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
            20                  25                  30

Leu His Cys Tyr Ala Ser Trp Arg Asn Ser Ser Gly Thr Ile Glu Leu
        35                  40                  45

Val Lys Lys Gly Cys Trp Asp Asp Asp Phe Asn Cys Tyr Asp Arg Gln
    50                  55                  60

Glu Cys Val Ala Thr Glu Glu Asn Pro Gln Val Tyr Phe Cys Cys Cys
```

```
            65                  70                  75                  80
Glu Gly Asn Phe Cys Asn Glu Arg Phe Thr His Leu Pro Glu Ala Gly
                    85                  90                  95

Gly Pro Glu Val Thr Tyr Glu Pro Pro Thr Gly Gly Thr His
                100                 105                 110

Thr Cys Pro Pro Cys Pro Ala Pro Glu Leu Leu Gly Gly Pro Ser Val
                115                 120                 125

Phe Leu Phe Pro Pro Lys Pro Lys Asp Thr Leu Met Ile Ser Arg Thr
            130                 135                 140

Pro Glu Val Thr Cys Val Val Val Asp Val Ser His Glu Asp Pro Glu
145                 150                 155                 160

Val Lys Phe Asn Trp Tyr Val Asp Gly Val Glu Val His Asn Ala Lys
                165                 170                 175

Thr Lys Pro Arg Glu Glu Gln Tyr Asn Ser Thr Tyr Arg Val Val Ser
                180                 185                 190

Val Leu Thr Val Leu His Gln Asp Trp Leu Asn Gly Lys Glu Tyr Lys
                195                 200                 205

Cys Lys Val Ser Asn Lys Ala Leu Pro Ala Pro Ile Glu Lys Thr Ile
        210                 215                 220

Ser Lys Ala Lys Gly Gln Pro Arg Glu Pro Gln Val Tyr Thr Leu Pro
225                 230                 235                 240

Pro Ser Arg Glu Glu Met Thr Lys Asn Gln Val Ser Leu Thr Cys Leu
                245                 250                 255

Val Lys Gly Phe Tyr Pro Ser Asp Ile Ala Val Glu Trp Glu Ser Asn
                260                 265                 270

Gly Gln Pro Glu Asn Asn Tyr Lys Thr Thr Pro Pro Val Leu Asp Ser
            275                 280                 285

Asp Gly Ser Phe Phe Leu Tyr Ser Lys Leu Thr Val Asp Lys Ser Arg
        290                 295                 300

Trp Gln Gln Gly Asn Val Phe Ser Cys Ser Val Met His Glu Ala Leu
305                 310                 315                 320

His Asn His Tyr Thr Gln Lys Ser Leu Ser Leu Ser Pro Gly Lys
                325                 330                 335

<210> SEQ ID NO 29
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
            20                  25                  30

Leu His Cys Tyr Ala Ser Trp Arg Asn Ser Ser Gly Thr Ile Glu Leu
        35                  40                  45

Val Lys Lys Gly Cys Trp Asp Asp Asp Phe Asn Cys Tyr Asp Arg Gln
    50                  55                  60

Glu Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Thr
                100                 105
```

<210> SEQ ID NO 30
<211> LENGTH: 1083
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (76)..(396)

<400> SEQUENCE: 30

```
atggatgcaa tgaagagagg gctctgctgt gtgctgctgc tgtgtggagc agtcttcgtt      60
tcgcccggcg ccgcc gaa acc cgc gaa tgt att tat tac aat gct aat tgg     111
                Glu Thr Arg Glu Cys Ile Tyr Tyr Asn Ala Asn Trp
                  1               5                  10 gaa ctc gaa cgg acg aac caa tcc ggg ctc gaa cgg tgt gag ggg gaa     159
Glu Leu Glu Arg Thr Asn Gln Ser Gly Leu Glu Arg Cys Glu Gly Glu
         15                  20                  25 cag gat aaa cgc ctc cat tgc tat gcg tcg tgg agg aac tcc tcc ggg     207
Gln Asp Lys Arg Leu His Cys Tyr Ala Ser Trp Arg Asn Ser Ser Gly
 30                  35                  40 acg att gaa ctg gtc aag aaa ggg tgc tgg gac gac gat ttc aat tgt     255
Thr Ile Glu Leu Val Lys Lys Gly Cys Trp Asp Asp Asp Phe Asn Cys
 45                  50                  55                  60 tat gac cgc cag gaa tgt gtc gcg acc gaa gag aat ccg cag gtc tat     303
Tyr Asp Arg Gln Glu Cys Val Ala Thr Glu Glu Asn Pro Gln Val Tyr
                 65                  70                  75 ttc tgt tgt tgc gag ggg aat ttc tgt aat gaa cgg ttt acc cac ctc     351
Phe Cys Cys Cys Glu Gly Asn Phe Cys Asn Glu Arg Phe Thr His Leu
             80                  85                  90 ccc gaa gcc ggc ggg ccc gag gtg acc tat gaa ccc ccg ccc acc         396
Pro Glu Ala Gly Gly Pro Glu Val Thr Tyr Glu Pro Pro Pro Thr
         95                 100                 105 ggtggtggaa ctcacacatg cccaccgtgc ccagcacctg aactcctggg gggaccgtca    456
gtcttcctct tccccccaaa acccaaggac accctcatga tctcccggac ccctgaggtc    516
acatgcgtgg tggtggacgt gagccacgaa gaccctgagg tcaagttcaa ctggtacgtg    576
gacggcgtgg aggtgcataa tgccaagaca agccgcggg aggagcagta caacagcacg    636
taccgtgtgg tcagcgtcct caccgtcctg caccaggact ggctgaatgg caaggagtac    696
aagtgcaagg tctccaacaa agccctccca gcccccatcg agaaaaccat ctccaaagcc    756
aaagggcagc cccgagaacc acaggtgtac accctgcccc catcccggga ggagatgacc    816
aagaaccagg tcagcctgac ctgcctggtc aaaggcttct atcccagcga catcgccgtg    876
gagtgggaga gcaatgggca gccggagaac aactacaaga ccacgcctcc cgtgctggac    936
tccgacggct ccttcttcct ctatagcaag ctcaccgtgg acaagagcag gtggcagcag    996
gggaacgtct tctcatgctc cgtgatgcat gaggctctgc acaaccacta cacgcagaag   1056
agcctctccc tgtccccggg taaatga                                       1083
```

<210> SEQ ID NO 31
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 31

```
gaaacccgcg aatgtattta ttacaatgct aattgggaac tcgaacggac gaaccaatcc      60
gggctcgaac ggtgtgaggg ggaacaggat aaacgcctcc attgctatgc gtcgtggagg     120
aactcctccg ggacgattga actggtcaag aaagggtgct gggacgacga tttcaattgt     180
tatgaccgcc aggaatgtgt cgcgaccgaa gagaatccgc aggtctattt ctgttgttgc     240 gagggaatt tctgtaatga acggtttacc cacctccccg aagccggcgg gcccgaggtg      300
acctatgaac ccccgcccac c                                                321
```

<210> SEQ ID NO 32
<211> LENGTH: 115
<212> TYPE: PRT
<213> ORGANISM: Homo sapiens

<400> SEQUENCE: 32

```
Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Asp Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110

Ala Pro Thr
        115
```

<210> SEQ ID NO 33
<211> LENGTH: 1107
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33

```
tacctacgtt acttctctcc cgagacgaca cacgacgacg acacacctcg tcagaagcaa     60
agcgggccgc ggagacccgc acccctccga ctctgtgccc tcacgtagat gatgttgcgg    120 ttgacccctcg acctcgcgtg gttggtctcg ccggacctcg cgacgcttcc gctcgtcctg    180
ttcgccgacg tgacgatgcg gaggaccgcg ttgtcgagac cgtggtagct cgagcacttc    240
ttcccgacga ccctactact gaagttgacg atgctatccg tcctcacaca ccggtgactc    300
ctcttggggg tccacatgaa gacgacgaca cttccgttga agacgttgct cgcgaagtga    360
gtaaacggtc tccgaccccc gggccttcag tgcatgctcg gtgggggctg tcggggtgg    420 ccaccacctt gagtgtgtac gggtggcacg ggtcgtggac ttgaggaccc cctggcagt    480 cagaaggaga agggggggttt tgggttcctg tgggagtact agagggcctg gggactccag    540
tgtacgcacc accacctgca ctcggtgctt ctgggactcc agttcaagtt gaccatgcac    600
ctgccgcacc tccacgtatt acggttctgt tccggcgccc tcctcgtcat gttgtcgtgc    660
atggcacacc agtcgcagga gtggcaggac gtggtcctga ccgacttacc gttcctcatg    720
```

| | |
|---|---:|
| ttcacgttcc agaggttgtt tcgggagggt cggggtagc tcttttggta gaggtttcgg | 780 |
| tttcccgtcg gggctcttgg tgtccacatg tgggacgggg gtagggccct cctctactgg | 840 |
| ttcttggtcc agtcggactg gacggaccag tttccgaaga tagggtcgct gtagcggcac | 900 |
| ctcaccctct cgttacccgt cggcctcttg ttgatgttct ggtgcggagg gcacgacctg | 960 |
| aggctgccga ggaagaagga gatatcgttc gagtggcacc tgttctcgtc caccgtcgtc | 1020 |
| cccttgcaga agagtacgag gcactacgta ctccgagacg tgttggtgat gtgcgtcttc | 1080 |
| tcggagaggg acaggggccc atttact | 1107 |

<210> SEQ ID NO 34
<211> LENGTH: 1083
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34

| | |
|---|---:|
| tacctacgtt acttctctcc cgagacgaca cacgacgacg acacacctcg tcagaagcaa | 60 |
| agcgggccgc ggcgactctg tgccctcacg tagatgatgt tgcggttgac cctcgacctc | 120 |
| gcgtggttgg tctcgccgga cctcgcgacg cttccgctcg tcctgttcgc cgacgtgacg | 180 |
| atgcggagga ccgcgttgtc gagaccgtgg tagctcgagc acttcttccc gacgaccctg | 240 |
| ctactgaagt tgacgatgct atccgtcctc acacaccggt gactcctctt ggggtccac | 300 |
| atgaagacga cgacacttcc gttgaagacg ttgctcgcga agtgagtaaa cggtctccga | 360 |
| cccccgggcc ttcagtgcat gctcggtggg ggctgtccac caccttgagt gtgtacgggt | 420 |
| ggcacgggtc gtggacttga ggaccccct ggcagtcaga aggagaaggg gggttttggg | 480 |
| ttcctgtggg agtactagag ggcctgggga ctccagtgta cgcaccacca cctgcactcg | 540 |
| gtgcttctgg gactccagtt caagttgacc atgcacctgc cgcacctcca cgtattacgg | 600 |
| ttctgtttcg gcgccctcct cgtcatgttg tcgtgcatgg cacaccagtc gcaggagtgg | 660 |
| caggacgtgg tcctgaccga cttaccgttc ctcatgttca cgttccagag gttgtttcgg | 720 |
| gagggtcggg ggtagctctt ttggtagagg tttcggtttc ccgtcggggc tcttggtgtc | 780 |
| cacatgtggg acggggtag ggccctcctc tactggttct tggtccagtc ggactggacg | 840 |
| gaccagtttc gaagatagg gtcgctgtag cggcacctca ccctctcgtt acccgtcggc | 900 |
| ctcttgttga tgttctggtg cggagggcac gacctgaggc tgccgaggaa gaaggagata | 960 |
| tcgttcgagt ggcacctgtt ctcgtccacc gtcgtcccct gcagaagag tacgaggcac | 1020 |
| tacgtactcc gagacgtgtt ggtgatgtgc gtcttctcgg agagggacag ggcccattt | 1080 |
| act | 1083 |

<210> SEQ ID NO 35
<211> LENGTH: 1083
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35

| | |
|---|---:|
| tacctacgtt acttctctcc cgagacgaca cacgacgacg acacacctcg tcagaagcaa | 60 |
| agcgggccgc ggcggctttg ggcgcttaca taaataatgt tacgattaac ccttgagctt | 120 |
| gcctgcttgg ttaggcccga gcttgccaca ctccccttg tcctatttgc ggaggtaacg | 180 |

```
atacgcagca cctccttgag gaggccctgc taacttgacc agttctttcc cacgaccctg      240
ctgctaaagt taacaatact ggcggtcctt acacagcgct ggcttctctt aggcgtccag      300
ataaagacaa caacgctccc cttaaagaca ttacttgcca aatgggtgga ggggcttcgg      360
ccgcccgggc tccactggat acttgggggc gggtggccac caccttgagt gtgtacgggt      420
ggcacgggtc gtggacttga gaccccccct ggcagtcaga aggagaaggg gggttttggg      480
ttcctgtggg agtactagag ggcctgggga ctccagtgta cgcaccacca cctgcactcg      540
gtgcttctgg gactccagtt caagttgacc atgcacctgc cgcacctcca cgtattacgg      600
ttctgtttcg gcgccctcct cgtcatgttg tcgtgcatgg cacaccagtc gcaggagtgg      660
caggacgtgg tcctgaccga cttaccgttc ctcatgttca cgttccagag gttgtttcgg      720
gagggtcggg ggtagctctt ttggtagagg tttcggtttc ccgtcgggc tcttggtgtc       780 cacatgtggg acggggtag ggccctcctc tactggttct tggtccagtc ggactggacg       840
gaccagtttc cgaagatagg gtcgctgtag cggcacctca ccctctcgtt acccgtcggc      900
ctcttgttga tgttctggtg cggagggcac gacctgaggc tgccgaggaa gaaggagata     960
tcgttcgagt ggcacctgtt ctcgtccacc gtcgtcccct tgcagaagag tacgaggcac    1020
tacgtactcc gagacgtgtt ggtgatgtgc gtcttctcgg agagggacag gggcccattt    1080
act                                                                    1083
```

<210> SEQ ID NO 36  
<211> LENGTH: 141  
<212> TYPE: PRT  
<213> ORGANISM: Homo sapiens

<400> SEQUENCE: 36

```
Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Leu Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Gly Pro Trp Ala Ser Thr Thr Ile
            100                 105                 110

Pro Ser Gly Gly Pro Glu Ala Thr Ala Ala Gly Asp Gln Gly Ser
        115                 120                 125

Gly Ala Leu Trp Leu Cys Leu Glu Gly Pro Ala His Glu
    130                 135                 140
```

<210> SEQ ID NO 37  
<211> LENGTH: 141  
<212> TYPE: PRT  
<213> ORGANISM: Artificial Sequence  
<220> FEATURE:  
<223> OTHER INFORMATION: Description of Artificial Sequence: Synthetic polypeptide

<400> SEQUENCE: 37

```
Gly Arg Gly Glu Ala Glu Thr Arg Glu Cys Ile Tyr Tyr Asn Ala Asn
1               5                   10                  15
```

```
Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Asp Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Gly Pro Trp Ala Ser Thr Thr Ile
            100                 105                 110

Pro Ser Gly Gly Pro Glu Ala Thr Ala Ala Gly Asp Gln Gly Ser
            115                 120                 125

Gly Ala Leu Trp Leu Cys Leu Glu Gly Pro Ala His Glu
        130                 135                 140

<210> SEQ ID NO 38
<211> LENGTH: 370
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Asp Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Gly Pro Trp Ala Ser Thr Thr Ile
            100                 105                 110

Pro Ser Gly Gly Pro Glu Ala Thr Ala Ala Gly Asp Gln Gly Ser
            115                 120                 125

Gly Ala Leu Trp Leu Cys Leu Glu Gly Pro Ala His Glu Thr Gly Gly
        130                 135                 140

Gly Thr His Thr Cys Pro Pro Cys Pro Ala Pro Glu Leu Leu Gly Gly
145                 150                 155                 160

Pro Ser Val Phe Leu Phe Pro Pro Lys Pro Lys Asp Thr Leu Met Ile
            165                 170                 175

Ser Arg Thr Pro Glu Val Thr Cys Val Val Val Asp Val Ser His Glu
        180                 185                 190

Asp Pro Glu Val Lys Phe Asn Trp Tyr Val Asp Gly Val Glu Val His
        195                 200                 205

Asn Ala Lys Thr Lys Pro Arg Glu Glu Gln Tyr Asn Ser Thr Tyr Arg
    210                 215                 220

Val Val Ser Val Leu Thr Val Leu His Gln Asp Trp Leu Asn Gly Lys
225                 230                 235                 240
```

-continued

```
Glu Tyr Lys Cys Lys Val Ser Asn Lys Ala Leu Pro Ala Pro Ile Glu
                245                 250                 255

Lys Thr Ile Ser Lys Ala Lys Gly Gln Pro Arg Glu Pro Gln Val Tyr
            260                 265                 270

Thr Leu Pro Pro Ser Arg Glu Glu Met Thr Lys Asn Gln Val Ser Leu
        275                 280                 285

Thr Cys Leu Val Lys Gly Phe Tyr Pro Ser Asp Ile Ala Val Glu Trp
    290                 295                 300

Glu Ser Asn Gly Gln Pro Glu Asn Asn Tyr Lys Thr Thr Pro Pro Val
305                 310                 315                 320

Leu Asp Ser Asp Gly Ser Phe Phe Leu Tyr Ser Lys Leu Thr Val Asp
                325                 330                 335

Lys Ser Arg Trp Gln Gln Gly Asn Val Phe Ser Cys Ser Val Met His
            340                 345                 350

Glu Ala Leu His Asn His Tyr Thr Gln Lys Ser Leu Ser Leu Ser Pro
        355                 360                 365

Gly Lys
    370

<210> SEQ ID NO 39
<211> LENGTH: 512
<212> TYPE: PRT
<213> ORGANISM: Homo sapiens

<400> SEQUENCE: 39

Met Thr Ala Pro Trp Val Ala Leu Ala Leu Leu Trp Gly Ser Leu Trp
1               5                   10                  15

Pro Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Ala
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Val Thr Tyr Glu Pro
        115                 120                 125

Pro Pro Thr Ala Pro Thr Leu Leu Thr Val Leu Ala Tyr Ser Leu Leu
    130                 135                 140

Pro Ile Gly Gly Leu Ser Leu Ile Val Leu Leu Ala Phe Trp Met Tyr
145                 150                 155                 160

Arg His Arg Lys Pro Pro Tyr Gly His Val Asp Ile His Glu Asp Pro
                165                 170                 175

Gly Pro Pro Pro Pro Ser Pro Leu Val Gly Leu Lys Pro Leu Gln Leu
            180                 185                 190

Leu Glu Ile Lys Ala Arg Gly Arg Phe Gly Cys Val Trp Lys Ala Gln
        195                 200                 205

Leu Met Asn Asp Phe Val Ala Val Lys Ile Phe Pro Leu Gln Asp Lys
    210                 215                 220

Gln Ser Trp Gln Ser Glu Arg Glu Ile Phe Ser Thr Pro Gly Met Lys
225                 230                 235                 240
```

```
His Glu Asn Leu Leu Gln Phe Ile Ala Ala Glu Lys Arg Gly Ser Asn
                245                 250                 255

Leu Glu Val Glu Leu Trp Leu Ile Thr Ala Phe His Asp Lys Gly Ser
            260                 265                 270

Leu Thr Asp Tyr Leu Lys Gly Asn Ile Ile Thr Trp Asn Glu Leu Cys
            275                 280                 285

His Val Ala Glu Thr Met Ser Arg Gly Leu Ser Tyr Leu His Glu Asp
            290                 295                 300

Val Pro Trp Cys Arg Gly Glu Gly His Lys Pro Ser Ile Ala His Arg
305                 310                 315                 320

Asp Phe Lys Ser Lys Asn Val Leu Leu Lys Ser Asp Leu Thr Ala Val
                325                 330                 335

Leu Ala Asp Phe Gly Leu Ala Val Arg Phe Glu Pro Gly Lys Pro Pro
            340                 345                 350

Gly Asp Thr His Gly Gln Val Gly Thr Arg Arg Tyr Met Ala Pro Glu
            355                 360                 365

Val Leu Glu Gly Ala Ile Asn Phe Gln Arg Asp Ala Phe Leu Arg Ile
370                 375                 380

Asp Met Tyr Ala Met Gly Leu Val Leu Trp Glu Leu Val Ser Arg Cys
385                 390                 395                 400

Lys Ala Ala Asp Gly Pro Val Asp Glu Tyr Met Leu Pro Phe Glu Glu
                405                 410                 415

Glu Ile Gly Gln His Pro Ser Leu Glu Glu Leu Gln Glu Val Val Val
            420                 425                 430

His Lys Lys Met Arg Pro Thr Ile Lys Asp His Trp Leu Lys His Pro
            435                 440                 445

Gly Leu Ala Gln Leu Cys Val Thr Ile Glu Glu Cys Trp Asp His Asp
            450                 455                 460

Ala Glu Ala Arg Leu Ser Ala Gly Cys Val Glu Glu Arg Val Ser Leu
465                 470                 475                 480

Ile Arg Arg Ser Val Asn Gly Thr Thr Ser Asp Cys Leu Val Ser Leu
                485                 490                 495

Val Thr Ser Val Thr Asn Val Asp Leu Pro Pro Lys Glu Ser Ser Ile
            500                 505                 510

<210> SEQ ID NO 40
<211> LENGTH: 115
<212> TYPE: PRT
<213> ORGANISM: Homo sapiens

<400> SEQUENCE: 40

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
                20                  25                  30

Glu Gln Asp Lys Arg Leu His Cys Tyr Ala Ser Trp Ala Asn Ser Ser
            35                  40                  45

Gly Thr Ile Glu Leu Val Lys Lys Gly Cys Trp Leu Asp Asp Phe Asn
        50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110
```

Ala Pro Thr
        115

<210> SEQ ID NO 41
<211> LENGTH: 100
<212> TYPE: PRT
<213> ORGANISM: Homo sapiens

<400> SEQUENCE: 41

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Ala Asn Ser Ser
        35                  40                  45

Gly Thr Ile Glu Leu Val Lys Lys Gly Cys Trp Leu Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala
        100

<210> SEQ ID NO 42
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Thr Gly Gly Gly
1

<210> SEQ ID NO 43
<211> LENGTH: 368
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Met Asp Ala Met Lys Arg Gly Leu Cys Cys Val Leu Leu Leu Cys Gly
1               5                   10                  15

Ala Val Phe Val Ser Pro Gly Ala Ser Gly Arg Gly Glu Ala Glu Thr
            20                  25                  30

Arg Glu Cys Ile Tyr Tyr Asn Ala Asn Trp Glu Leu Glu Arg Thr Asn
        35                  40                  45

Gln Ser Gly Leu Glu Arg Cys Glu Gly Glu Gln Asp Lys Arg Leu His
    50                  55                  60

Cys Tyr Ala Ser Trp Arg Asn Ser Ser Gly Thr Ile Glu Leu Val Lys
65                  70                  75                  80

Lys Gly Cys Trp Asp Asp Asp Phe Asn Cys Tyr Asp Arg Gln Glu Cys
                85                  90                  95

Val Ala Thr Glu Glu Asn Pro Gln Val Tyr Phe Cys Cys Cys Glu Gly
            100                 105                 110

Asn Phe Cys Asn Glu Arg Phe Thr His Leu Pro Glu Ala Gly Gly Pro

```
                    115                 120                 125
Glu Val Thr Tyr Glu Pro Pro Thr Ala Pro Thr Gly Gly Gly Thr
    130                 135                 140

His Thr Cys Pro Pro Cys Pro Ala Pro Glu Leu Leu Gly Gly Pro Ser
145                 150                 155                 160

Val Phe Leu Phe Pro Pro Lys Pro Lys Asp Thr Leu Met Ile Ser Arg
                165                 170                 175

Thr Pro Glu Val Thr Cys Val Val Val Asp Val Ser His Glu Asp Pro
            180                 185                 190

Glu Val Lys Phe Asn Trp Tyr Val Asp Gly Val Glu Val His Asn Ala
        195                 200                 205

Lys Thr Lys Pro Arg Glu Glu Gln Tyr Asn Ser Thr Tyr Arg Val Val
    210                 215                 220

Ser Val Leu Thr Val Leu His Gln Asp Trp Leu Asn Gly Lys Glu Tyr
225                 230                 235                 240

Lys Cys Lys Val Ser Asn Lys Ala Leu Pro Ala Pro Ile Glu Lys Thr
                245                 250                 255

Ile Ser Lys Ala Lys Gly Gln Pro Arg Glu Pro Gln Val Tyr Thr Leu
            260                 265                 270

Pro Pro Ser Arg Glu Glu Met Thr Lys Asn Gln Val Ser Leu Thr Cys
        275                 280                 285

Leu Val Lys Gly Phe Tyr Pro Ser Asp Ile Ala Val Glu Trp Glu Ser
    290                 295                 300

Asn Gly Gln Pro Glu Asn Asn Tyr Lys Thr Thr Pro Pro Val Leu Asp
305                 310                 315                 320

Ser Asp Gly Ser Phe Phe Leu Tyr Ser Lys Leu Thr Val Asp Lys Ser
                325                 330                 335

Arg Trp Gln Gln Gly Asn Val Phe Ser Cys Ser Val Met His Glu Ala
            340                 345                 350

Leu His Asn His Tyr Thr Gln Lys Ser Leu Ser Leu Ser Pro Gly Lys
        355                 360                 365

<210> SEQ ID NO 44
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
            20                  25                  30

Leu His Cys Tyr Ala Ser Trp Arg Asn Ser Ser Gly Thr Ile Glu Leu
        35                  40                  45

Val Lys Lys Gly Cys Trp Asp Asp Asp Phe Asn Cys Tyr Asp Arg Gln
    50                  55                  60

Glu Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Thr
            100                 105
```